US007569688B2

(12) United States Patent
Hirano et al.

(10) Patent No.: US 7,569,688 B2
(45) Date of Patent: *Aug. 4, 2009

(54) PROPANE-1, 3-DIONE DERIVATIVE

(75) Inventors: Masaaki Hirano, Tsukuba (JP); Eiji Kawaminami, Tsukuba (JP); Akira Toyoshima, Tsukuba (JP); Hiroyuki Moritomo, Tsukuba (JP); Norio Seki, Tsukuba (JP); Ryutaro Wakayama, Tsukuba (JP); Minoru Okada, Tsukuba (JP); Toshiyuki Kusayama, Tsukuba (JP)

(73) Assignee: Astellas Pharma Inc., Tokyo (JP)

( * ) Notice: Subject to any disclaimer, the term of this patent is extended or adjusted under 35 U.S.C. 154(b) by 563 days.

This patent is subject to a terminal disclaimer.

(21) Appl. No.: 11/155,595

(22) Filed: Jun. 20, 2005

(65) Prior Publication Data

US 2005/0267110 A1 Dec. 1, 2005

Related U.S. Application Data

(62) Division of application No. 10/311,688, filed as application No. PCT/JP01/05813 on Jul. 4, 2001, now Pat. No. 6,960,591.

(30) Foreign Application Priority Data

Jul. 5, 2000 (JP) ............................ 2000-204425
May 23, 2001 (JP) ............................ 2001-153372

(51) Int. Cl.
*C07D 235/06* (2006.01)
*C07D 401/06* (2006.01)

(52) U.S. Cl. ................. 544/242; 544/333; 544/336; 544/405; 546/118; 546/174; 546/199; 546/256; 546/273.4; 548/180; 548/181; 548/304.4; 548/304.7; 548/305.4; 548/306.1; 548/310.4; 514/255.05; 514/256; 514/303; 514/314; 514/322; 514/333; 514/338; 514/365; 514/367; 514/394

(58) Field of Classification Search ............... 548/180, 548/181, 304.4, 304.7, 305.4, 306.1, 310.4; 546/118, 174, 199, 256, 273.4; 544/242, 544/333, 336, 405; 514/255.05, 256, 303, 514/314, 322, 333, 338, 365, 367, 394
See application file for complete search history.

(56) References Cited

U.S. PATENT DOCUMENTS 4,062,686 A  12/1977 Van Allan et al.
4,119,466 A  10/1978 Van Allan et al.
5,202,221 A  4/1993 Imai et al.
5,616,537 A  4/1997 Yokota et al.
5,770,544 A  6/1998 Yokota et al.
5,817,819 A  10/1998 Furuya et al.
6,960,591 B2 * 11/2005 Hirano et al. .......... 514/255.05

FOREIGN PATENT DOCUMENTS

| EP | 0 135 348 A2 | 3/1985 |
| EP | 0 332 044 A1 | 9/1989 |
| EP | 0 368 327 A2 | 5/1990 |
| EP | 368327 A2 | 5/1990 |
| EP | 0 631 177 A1 | 12/1994 |
| JP | 2000-95767 A | 4/2000 |
| WO | WO 94/01415 A1 | 1/1994 |
| WO | WO 95/28405 A1 | 10/1995 |
| WO | WO 99/52888 A1 | 10/1999 |
| WO | WO 02/102401 A1 | 12/2002 |

OTHER PUBLICATIONS

Jaro Komenda et al., Electrochemical Behavior and ESR Spectra of Nitro Substituted Mono- and Debenzoylmethylenebenzthiazolines and Selenazolies, Collect. Czech. Chem. Commun. (1979), vol. 44(5), pp. 1540-1551.
Miroslav Holik et al., H-NMR Study of Transfer of Substituent Effects in 2-Dibenzoylmethylene-3-Ethylbenzothiazolines and -Selenazolines, Collect. Czech. Chem. Commun. (1978), vol. 43(3), pp. 739-745.
A. Mistr et al., Organische Lichtempfindliche Stoffe V. Acylmethylenderivate Heterocyclischer Stickstoffhaltiger Basen ALS Sensibilisatoren Lichtempfindlicher Polymerer, Collect. Czech. Chem. Commun. (1973), vol. 38(12), pp. 3616-3622.
A. Mistr et al., Organische Lichtempfindliche Stoffee II. Benzoylmethylenderivate Heterocyclischer Stickstoffhaltiger Basen ALS Sensibilisatoren Fur Lichtempfindliche Polymere, Collect. Czech. Commun. (1971), vol. 36(1), pp. 150-163.
G.L. Gaeva and K.S. Liadikov, Zh. Nauch. Prikl. Fotogr. Kinematogr. (1971), vol. 16(4), pp. 282-288.
I.B. Dzvinchuk et al., "Formation of Unsymmetrical 2-(Diacylmethylene)-2,3-Dihydro-1H-Benzimidazoles During Acidolysis of 1-Benzoyl2-(β-Benzoyloxy-β-Phenylvinyl)-1H-Benzimidazole", vol. 37, Chemistry of Heterocyclic Compounds, No. 5 (2001), pp. 554-559.
European Search Report dated Feb. 13, 2004.
Junko Ishida et al., "Antitumor Agents. Part 214: †Synthesis and Evaluation of Curcumin Analogues as Cytotoxic Agents" Bioorganic & Medicinal Chemistry 10 (2002) 3481-3487.
Huirne et al., PubMed Abstract (Lancet 358 (9295): 1793-803), Nov. 2001.
Simone, Oncology: Introduction, Cecil Textbook of Medicine, 20th Edition, vol. 1, pp. 1004-1010, 1996.

* cited by examiner

*Primary Examiner*—Deepak Rao
(74) *Attorney, Agent, or Firm*—Sughrue Mion, PLLC

(57) ABSTRACT

Provided is a pharmaceutical composition containing a propane-1,3-dione derivative as the active ingredient, particularly a GnRH receptor antagonist. Also, provided is a propane-1,3-dione derivative having a GnRH antagonistic effect.

3 Claims, No Drawings

SEQUENCE LISTING

<160> NUMBER OF SEQ ID NOS: 4

<210> SEQ ID NO 1
<211> LENGTH: 987
<212> TYPE: DNA
<213> ORGANISM: Homo sapiens

<400> SEQUENCE: 1

| | | | | | | |
|---|---|---|---|---|---|---|
| atggcaaaca | gtgcctctcc | tgaacagaat | caaaatcact | gttcagccat | caacaacagc | 60 |
| atcccactga | tgcagggcaa | cctccccact | ctgaccttgt | ctggaaagat | ccgagtgacg | 120 |
| gttactttct | tccttttttct | gctctctgcg | acctttaatg | cttctttctt | gttgaaactt | 180 |
| cagaagtgga | cacagaagaa | agagaaaggg | aaaaagctct | caagaatgaa | gctgctctta | 240 |
| aaacatctga | ccttagccaa | cctgttggag | actctgattg | tcatgccact | ggatgggatg | 300 |
| tggaacatta | cagtccaatg | gtatgctgga | gagttactct | gcaaagttct | cagttatcta | 360 |
| aagcttttct | ccatgtatgc | cccagccttc | atgatggtgg | tgatcagcct | ggaccgctcc | 420 |
| ctggctatca | cgaggcccct | agctttgaaa | agcaacagca | agtcggaca | gtccatggtt | 480 |
| ggcctggcct | ggatcctcag | tagtgtcttt | gcaggaccac | agttatacat | cttcaggatg | 540 |
| attcatctag | cagacagctc | tggacagaca | aaagttttct | ctcaatgtgt | aacacactgc | 600 |
| agttttttcac | aatggtggca | tcaagcattt | tataactttt | tcaccttcag | ctgcctcttc | 660 |
| atcatccctc | ttttcatcat | gctgatctgc | aatgcaaaaa | tcatcttcac | cctgacacgg | 720 |
| gtccttcatc | aggaccccca | cgaactacaa | ctgaatcagt | ccaagaacaa | ataccaaga | 780 |
| gcacggctga | agactctaaa | aatgacggtt | gcatttgcca | cttcatttac | tgtctgctgg | 840 |
| actccctact | atgtcctagg | aatttggtat | tggtttgatc | ctgaaatgtt | aaacaggttg | 900 |
| tcagacccag | taaatcactt | cttctttctc | tttgcctttt | taaacccatg | ctttgatcca | 960 |
| cttatctatg | gatatttttc | tctgtga | | | | 987 |

<210> SEQ ID NO 2
<211> LENGTH: 328
<212> TYPE: PRT
<213> ORGANISM: Homo sapiens

<400> SEQUENCE: 2

Met Ala Asn Ser Ala Ser Pro Glu Gln Asn Gln Asn His Cys Ser Ala
1               5                   10                  15

Ile Asn Asn Ser Ile Pro Leu Met Gln Gly Asn Leu Pro Thr Leu Thr
            20                  25                  30

Leu Ser Gly Lys Ile Arg Val Thr Val Thr Phe Phe Leu Phe Leu Leu
        35                  40                  45

Ser Ala Thr Phe Asn Ala Ser Phe Leu Leu Lys Leu Gln Lys Trp Thr
    50                  55                  60

Gln Lys Lys Glu Lys Gly Lys Lys Leu Ser Arg Met Lys Leu Leu Leu
65                  70                  75                  80

Lys His Leu Thr Leu Ala Asn Leu Leu Glu Thr Leu Ile Val Met Pro
                85                  90                  95

Leu Asp Gly Met Trp Asn Ile Thr Val Gln Trp Tyr Ala Gly Glu Leu
            100                 105                 110

Leu Cys Lys Val Leu Ser Tyr Leu Lys Leu Phe Ser Met Tyr Ala Pro
        115                 120                 125

Ala Phe Met Met Val Val Ile Ser Leu Asp Arg Ser Leu Ala Ile Thr

|     |     |     |     | 130 |     |     |     | 135 |     |     |     | 140 |     |     |
| --- | --- | --- | --- | --- | --- | --- | --- | --- | --- | --- | --- | --- | --- | --- |

Arg Pro Leu Ala Leu Lys Ser Asn Ser Lys Val Gly Gln Ser Met Val
145                 150                 155                 160

Gly Leu Ala Trp Ile Leu Ser Ser Val Phe Ala Gly Pro Gln Leu Tyr
                165                 170                 175

Ile Phe Arg Met Ile His Leu Ala Asp Ser Ser Gly Gln Thr Lys Val
            180                 185                 190

Phe Ser Gln Cys Val Thr His Cys Ser Phe Ser Gln Trp Trp His Gln
        195                 200                 205

Ala Phe Tyr Asn Phe Phe Thr Phe Ser Cys Leu Phe Ile Ile Pro Leu
    210                 215                 220

Phe Ile Met Leu Ile Cys Asn Ala Lys Ile Ile Phe Thr Leu Thr Arg
225                 230                 235                 240

Val Leu His Gln Asp Pro His Glu Leu Gln Leu Asn Gln Ser Lys Asn
                245                 250                 255

Asn Ile Pro Arg Ala Arg Leu Lys Thr Leu Lys Met Thr Val Ala Phe
                260                 265                 270

Ala Thr Ser Phe Thr Val Cys Trp Thr Pro Tyr Tyr Val Leu Gly Ile
            275                 280                 285

Trp Tyr Trp Phe Asp Pro Glu Met Leu Asn Arg Leu Ser Asp Pro Val
    290                 295                 300

Asn His Phe Phe Phe Leu Phe Ala Phe Leu Asn Pro Cys Phe Asp Pro
305                 310                 315                 320

Leu Ile Tyr Gly Tyr Phe Ser Leu
                325

<210> SEQ ID NO 3
<211> LENGTH: 10
<212> TYPE: PRT
<213> ORGANISM: Artificial Sequence
<220> FEATURE:
<223> OTHER INFORMATION: Labeled Tyr with 125I and substituted with D
      form of Trp

<400> SEQUENCE: 3

Glu His Trp Ser Tyr Trp Leu Arg Pro Gly
1               5                   10

<210> SEQ ID NO 4
<211> LENGTH: 10
<212> TYPE: PRT
<213> ORGANISM: Homo sapiens

<400> SEQUENCE: 4

Glu His Trp Ser Tyr Gly Leu Arg Pro Gly
1               5                   10

PROPANE-1, 3-DIONE DERIVATIVE

This is a divisional of application Ser. No. 10/311,688 filed Dec. 19, 2002 now U.S. Pat. No. 6,960,591, which is a 371 National Stage Application of PCT/JP01/05813 filed Jul. 4, 2001, both of which are hereby incorporated by reference.

TECHNICAL FIELD

The present invention relates to a pharmaceutical composition containing a propane-1,3-dione derivative or a pharmaceutically acceptable salt thereof as the active ingredient and a novel propane-1,3-dione derivative.

BACKGROUND OF THE INVENTION

It is known that hypothalamic hormone or pituitary hormone takes part in a control system of secretion of peripheral hormones. In general, the secretion of anterior pituitary hormone is regulated by a secretion stimulating hormone or a secretion suppressing hormone secreted from an upper center, hypothalamus, a peripheral hormone secreted from the target organs them.

Gonadotropin releasing hormone (hereinafter, abbreviated as GnRH; also, GnRH is called as luteinizing hormone releasing hormone; LHRH) is known as a hormone which controls the secretion of sex hormones at the highest position, and regulates the secretion of luteinizing hormone (hereinafter, abbreviated as LH), follicle stimulating hormone (hereinafter, abbreviated as FSH), and sex hormones in the gonads through the intermediary of the receptor (hereinafter, abbreviated as GnRH receptor) which is considered to be present in anterior pituitary (Horumon to Rinsyo (Hormones and Clinical), 46, 46-57 (1998)). A specific and selective antagonist against the GnRH receptor is expected to be a drug for preventing and treating sex hormone-dependent diseases since it regulates the action of GnRH and controls the secretion of lower LH, FSH and sex hormones (Horumon to Rinsyo (Hormones and Clinical)(1998), ibid.).

As compounds having a GnRH receptor antagonistic property, peptide compounds such as linear peptides, cyclic hexapeptide derivatives and bicyclic peptide derivatives which are derivatives of GnRH have been known. Also, as non-peptide compounds having the property, the following aminobenzimidazole derivatives (Japanese Patent Laid-Open No. 95767/2000), thienopyrimidine derivatives (WO 95/28405), or the like has been reported.

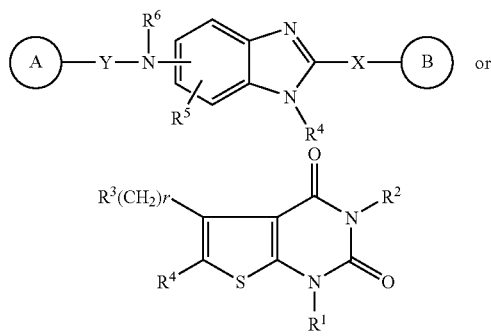

(refer to the above publications for the symbols in the formulae)

On the other hand, the known propane-1,3-dione derivatives having a benzimidazole, benzothiazole, or benzoxazole skeleton described in the following Table 1 have been reported as reagents for use as photosensitizer or the like (EP-A-135348, EP-A-631177, EP-A-368327, EP-A-332044, WO 94/01415, U.S. Pat. No. 4,062,686, U.S. Pat. No. 4,119,466, Collect. Czech. Chem. Commun. (1971), 36(1), 150-63, Zh. Nauch. Prikl. Fotogr. Kinematogr. (1971), 16(4), 282-8, Collect. Czech. Chem. Commun. (1978), 43(3), 739-45, Collect. Czech. Chem. Commun. (1979), 44(5), 1540-51, and Collect. Czech. Chem. Commun. (1973), 38(12), 3616-22), but pharmaceutical actions, particularly a GnRH receptor antagonistic action have not been disclosed.

DISCLOSURE OF THE INVENTION

As a result of the intensive studies on non-peptide compounds having an excellent GnRH receptor antagonistic action, the present inventors have found that 2-(1,3-dihydro-2H-benzimidazol-2-ylidene)-1,3-diphenylpropane-1,3-dione derivatives are useful. Furthermore, the inventors have developed various compounds based on the findings and have found that propane-1,3-dione derivatives represented by the following general formula (I) have an excellent GnRH receptor antagonistic action. Accordingly, they have accomplished the invention. Among the compounds of the invention, there are confirmed some compounds having a GnRH receptor-binding inhibitory activity equal to that of a peptide antagonist Cetrorelix which is commercialized at present. Thus, the invention relates to extremely useful compounds as non-peptide compounds.

Namely, the invention relates to the following:

That is, a pharmaceutical composition comprising a propane-1,3-dione derivative represented by the general formula (I):

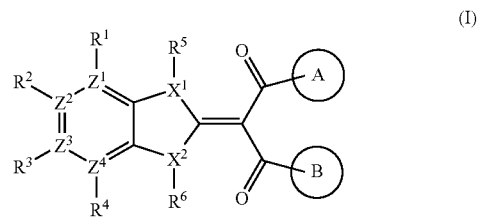

($R^1$, $R^2$, $R^3$ and $R^4$: the same or different, H, $NO_2$, CN, Halo, a hydrocarbon group which may be substituted, a heterocycle which may be substituted, a hydroxy which may be substituted, a carboxy which may be substituted, an acyl-O— which may be substituted, an acyl which may be substituted, a substituent —$S(O)n_{101}$— ($n_{101}$: an integer of 0 to 2, the same shall apply hereinafter), H—$S(O)n_{101}$—, a carbamoyl which may be substituted, a sulfamoyl which may be substituted, or an amino which may be substituted, and two adjacent groups selected from the group of $R^1$, $R^2$, $R^3$ and $R^4$ may be combined to form an aryl or a cycloalkenyl;

$R^5$ and $R^6$: the same or different, H, Halo, a hydrocarbon group which may be substituted or an amino which may be substituted;

$X^1$ and $X^2$: the same or different, N, S or O atom;

A and B: the same or different, an aryl which may be substituted or a heterocycle which may be substituted;

$Z^1$, $Z^2$, $Z^3$ and $Z^4$: C or N;

provided that 1) when $X^1$ and $X^2$ each is S or O, one or both of the corresponding $R^5$ and $R^6$ are absent; 2) when one to four of $Z^1$, $Z^2$, $Z^3$ and/or $Z^4$ are N, the corresponding $R^1$, $R^2$, $R^3$ and/or $R^4$ are absent)

or a pharmaceutically acceptable salt thereof as the active ingredient, preferably, the pharmaceutical composition which is a gonadotropin releasing hormone receptor antagonist, more preferably, the pharmaceutical composition comprising a propane-1,3-dione derivative wherein at least any one of $X^1$ and $X^2$ in the general formula (I) is N or the propane-1,3-dione derivative wherein $X^1$ and $X^2$ are N at the same time, or a pharmaceutically acceptable salt thereof as the active ingredient.

As another embodiment, the invention relates to a propane-1,3-dione derivative in the general formula (I) or a pharmaceutically acceptable salt thereof, provided that the compounds 1 to 39 shown in the following Table 1 are excluded, wherein the symbol Ph means phenyl, Me means methyl, Et means ethyl, or tBu means tert-butyl.

TABLE 1

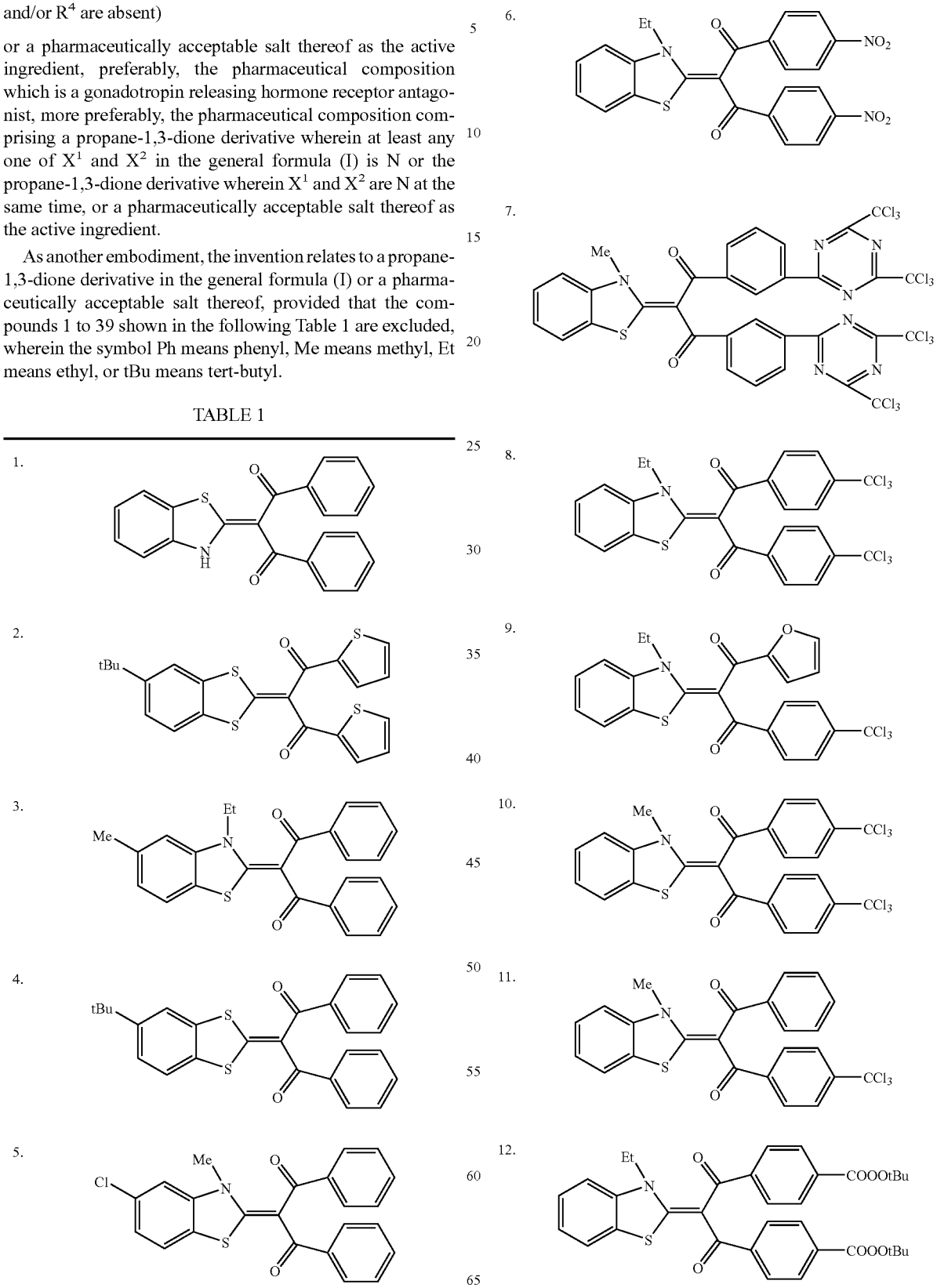

TABLE 1-continued
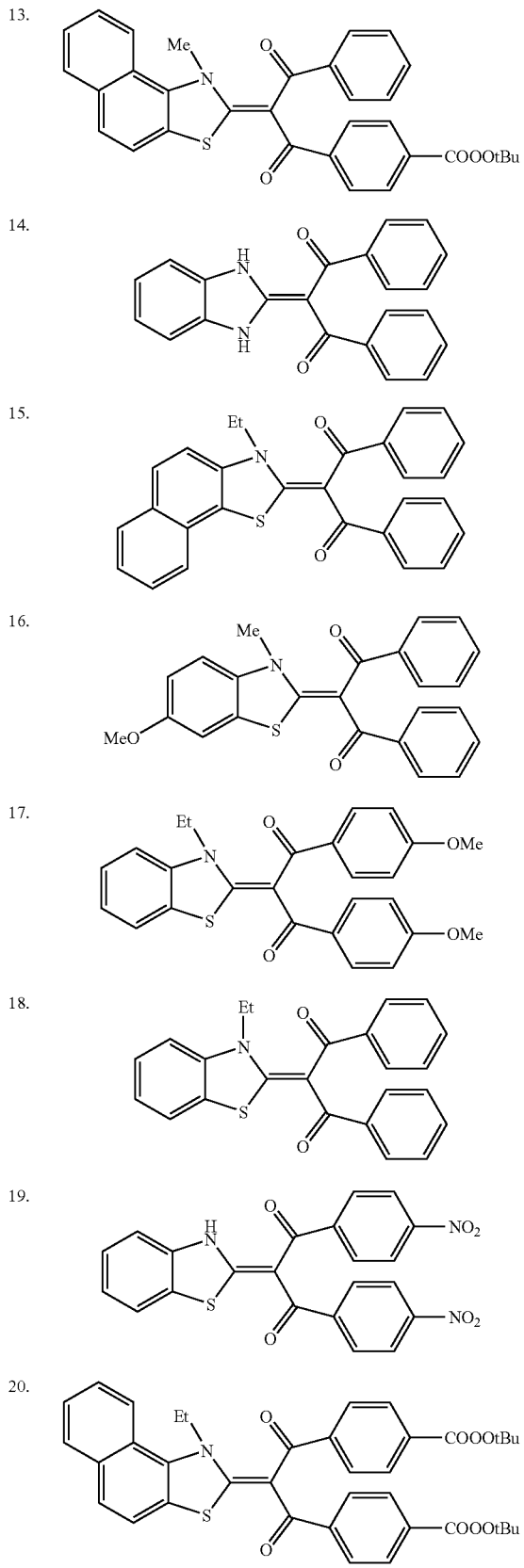
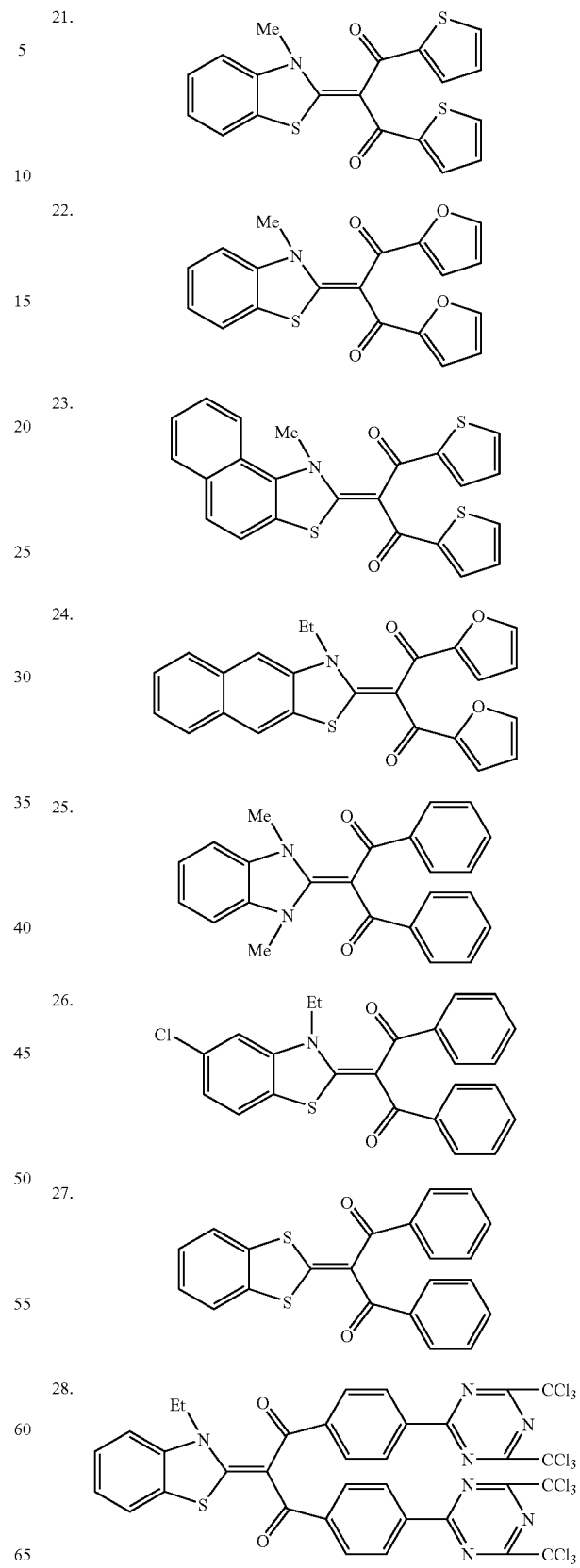

TABLE 1-continued

29. 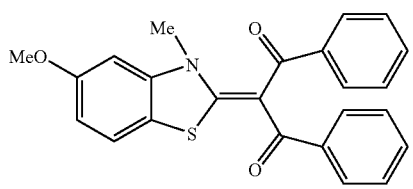

30. 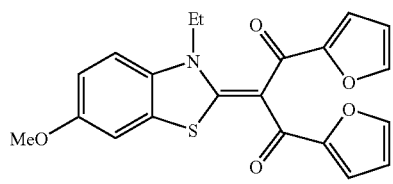

31. 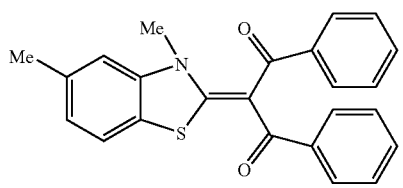

32. 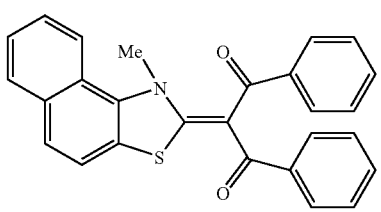

33. 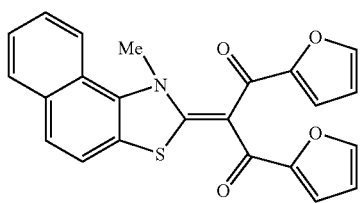

34. 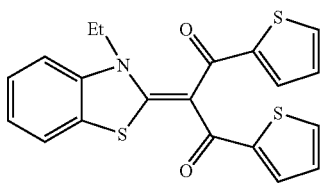

35. 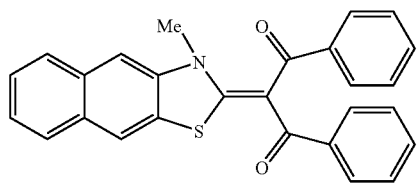

36. 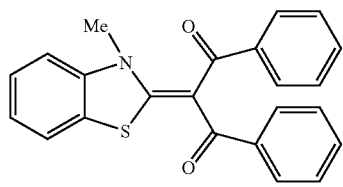

TABLE 1-continued

37. 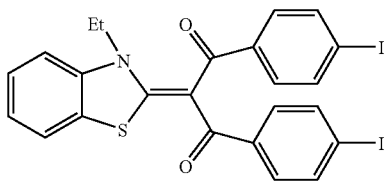

38. 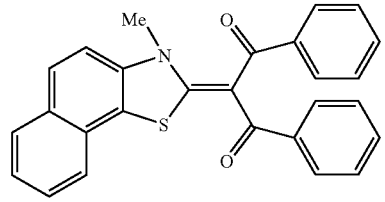

39. 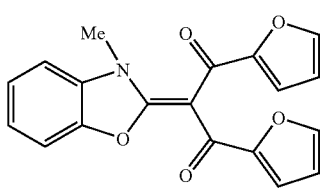

Preferably, it is the propane-1,3-dione derivative wherein at least any one of $X^1$ and $X^2$ in the general formula (I) is N or the propane-1,3-dione derivative wherein $X^1$ and $X^2$ in the general formula (I) are N at the same time or a pharmaceutically acceptable salt thereof. In addition, as the other embodiment, it is the propane-1,3-dione derivative wherein $R^1$, $R^2$, $R^3$ or $R^4$ is H, an amino which may be substituted or a hydroxy which may be substituted, or a pharmaceutically acceptable salt thereof.

BEST MODE FOR CARRYING OUT THE INVENTION

The invention is further described in detail.

As the "Halo", fluorine, chlorine, bromine, or iodine atoms can be mentioned

The "hydrocarbon group" means a group composed of $C_{1-15}$ carbons and hydrogens and is any form of linear or branched, monocyclic or fused polycyclic, and/or saturated or unsaturated ones, and preferably means an alkyl, alkenyl, alkynyl, cycloalkyl, cycloalkenyl, aryl, or aryl-alkyl.

The "alkyl" means a linear or branched saturated hydrocarbon group, and is preferably a $C_{1-10}$ alkyl, more preferably a $C_{1-6}$ alkyl. Specifically, it is methyl, ethyl, isopropyl, decyl, or the like. The "alkenyl" means a linear or branched hydrocarbon group having at least one or more double bonds, and is preferably a $C_{2-10}$ alkenyl. Specifically, it is vinyl, propenyl, allyl, isopropenyl, hexenyl, or the like. The "alkynyl" means a linear or branched hydrocarbon group having at least one or more triple bonds, and is preferably a $C_{2-10}$ alkynyl. Specifically, it is ethynyl, propynyl, butynyl, or the like. The "cycloalkyl" means a monocyclic saturated hydrocarbon ring, and is preferably a "$C_{3-8}$ cycloalkyl". Specifically, it is cyclopropyl, cyclopentyl, cyclohexyl, or the like. The "cycloalkenyl" means a monocyclic unsaturated hydrocarbon ring, and is preferably a "$C_{3-8}$ cycloalkenyl". Specifically, it is cyclopentenyl, cyclohexenyl, or the like. The "aryl" means an aromatic hydrocarbon ring, and is preferably $C_{6-14}$ aryl. Specifically, it is phenyl, naphthyl, 5,6,7,8-tetrahydronaphthyl, indenyl, anthryl, fluorenyl, or the like.

The "heterocyclic group" means a five- or six-membered, monocyclic or bicyclic, saturated or unsaturated ring containing from 1 to 4 heteroatoms selected from N, S and O. The unsaturated ring includes aromatic rings (heteroaryls) and non-aromatic rings. As the monocyclic groups, there may be mentioned pyrrolidinyl, pyrazolidinyl, dioxanyl, piperadinyl, piperidinyl, morpholino, trithianyl, dioxolanyl, furyl, thienyl, pyrrolyl, imidazolyl, pyrazolyl, thiazolyl, oxazolyl, pyridyl, pyrazinyl, pyrimidyl, triazolyl, thiadiazolyl, pyridazinyl, triazinyl, oxadiazolyl, or the like. As the bicyclic groups, there may be mentioned indolinyl, 3,4-methylenedioxyphenyl, 3,4-ethylenedioxyphenyl, benzofuranyl, benzothienyl, benzothiadiazolyl, benzothiazolyl, benzimidazolyl, indolyl, quinolyl, isoquinolyl, quinoxalinyl, or the like. It is preferably a five- or six-membered monocyclic heteroaryl, more preferably furyl, thienyl, imidazolyl, thiazolyl, or pyridyl.

The "acyl" includes HCO—, a $C_{1-15}$ hydrocarbon group-CO—, a heterocyclic group-CO—, a heterocyclic group-alkyl-CO—, a heterocyclic group-alkenyl-CO—, a heterocyclic group-alkynyl-CO—, a $C_{1-15}$ hydrocarbon group-CS—, a heterocyclic group-CS—, a heterocyclic group-alkyl-CS—, a heterocyclic group-alkenyl-CS—, or a heterocyclic group-alkynyl-CS—. It is preferably a $C_{1-15}$ hydrocarbon group-CO— or a heterocyclic group-CO—, specifically HCO—, acetyl, propionyl, 2-methylbut-2-en-2-oyl, benzoyl, nicotinoyl, thenoyl, pyrrolidinylcarbonyl, piperidinylcarbonyl, or the like.

The "Halo hydrocarbon group" includes, for example, a Halo $C_{1-10}$ alkyl and a Halo $C_{6-14}$ aryl and specifically, chloromethyl, trifluoromethyl, fluorophenyl, difluorophenyl, trifluorophenyl, or the like.

The "heterocycle-ylidene" is a group wherein two bonding hands are present from the identical carbon atom in a heterocycle, and examples thereof include 3-methyl-4-oxo-2-thioxothiazolydin-5-ylidene and the like.

The "heterocyclic group-$C_{1-10}$ alkylidene" includes pyridylmethylidene and the like.

The substituents in the hydrocarbon group which may be substituted include specifically the substituents in the following a group.

The substituents in the heterocycle which may be substituted, the hydroxy which may be substituted, the carboxy which may be substituted, the acyl-O— which may be substituted, the acyl which may be substituted, the substituent —S(O)$n_{101}$—, the carbamoyl which may be substituted, and the sulfamoyl which may be substituted include specifically the substituents in the following b group.

The substituents in the amino which may be substituted include specifically the substituents in the following c group.

Moreover, the substituents in the aryl or heterocyclic group which may be substituted in A ring and B ring include the substituents in the following d group.

a group: OH, $NO_2$, COOH, Halo, $C_{6-14}$ aryl, heterocyclic group, $R^{101}{}_3SiO$— and/or $R^{101}$—$T^{101}$—

$R^{101}$: (1) H, (2) $C_{3-8}$ cycloalkyl, (3) heterocyclic group,
(4) $C_{1-10}$ alkyl which may be substituted by [OH, $NO_2$, COOH, Halo, heterocyclic group, $C_{1-10}$ alkyl-CO—, $C_{1-10}$ alkyl-O—, $C_{1-10}$ alkyl-O—CO—, and/or $(R^{102})n_{102}C_{6-14}$ aryl], $R^{102}$: H, Halo, $NO_2$, OH, COOH, $C_{1-10}$ alkyl-O— or $C_{1-10}$ alkyl-O—CO—, $n_{102}$: an integer of 1 to 5, (5) $C_{6-14}$ aryl which may be substituted by OH, CN, $NO_2$, Halo, and/or $C_{1-10}$ alkyl-CONR$^{103}$—, $R^{103}$: the same as or different from $R^{101}$, (a) H, (b) $C_{3-8}$ cycloalkyl, (c) heterocyclic group,
(d) $C_{1-10}$ alkyl which may be substituted by COOH, $C_{1-10}$ alkyl-O—CO—, $(R^{104})n_{102}$—$C_{6-14}$ aryl or $(R^{104})n_{102}$— heterocyclic group, $R^{104}$: H, OH, Halo or $C_{1-10}$ alkyl-O—, or (e) CE-14 aryl which may be substituted by OH, CN, $NO_2$, Halo or $C_1$-$C_{10}$ alkyl-CONR$^{105}$—, $R^{105}$: (a) H, (b) $C_{3-8}$ cycloalkyl, (c) heterocyclic group,
(d) $C_{1-10}$ alkyl which may be substituted by COOH, $C_{1-10}$ alkyl-O—CO—, $C_{6-14}$ aryl or heterocyclic group, or (e) $C_{6-14}$ aryl which may be substituted by OH, CN, $NO_2$ or Halo, $T^{101}$: —O—, —CO—, —CO—O—, —O—CO—, —NR$^{103}$—CO— or —NR$^{103}$—, the same shall apply hereinafter, b group: (1) H, (2) $C_{3-8}$ cycloalkyl, (3) $C_{6-14}$ aryl which may be substituted by $C_{1-10}$ alkyl-O—, (4) heterocyclic group, (5) $C_{1-10}$ alkyl which may be substituted by (OH, $NO_2$, Halo, heterocyclic group, $R^{101}R^{103}N$, $C_{1-10}$ alkyl-O—, acyl or $(R^{106})n_{102}$—$C_{6-14}$ aryl), $R^{106}$: H, COOH, $NO_2$, $R^{101}R^{103}N$, acyl-NR$^{101}$— or $C_{1-10}$ alkyl-O—CO—, the same shall apply hereinafter, c group: (1) heterocyclic group which may be substituted by $C_{1-10}$ alkyl, Halo $C_{1-10}$ alkyl or $C_{6-14}$ aryl-$C_{1-10}$ alkyl, (2) $C_{6-14}$ aryl which may be substituted by cycloalkyl or $R^{101}R^{103}N$, (3) $C_{1-10}$ alkyl which may be substituted by $R^{107}$, $R^{107}$: (a) $C_{3-8}$ cycloalkyl, (b) $C_{3-8}$ cycloalkenyl, (c) $R^{108}$—O—, $R^{108}$: (i) $C_{1-10}$ alkyl which may be substituted by $C_{6-14}$ aryl, heterocyclic group or $R^{101}R^{103}N$, or (ii) aryl which may be substituted by $C_{6-14}$ aryl or $R^{101}R^{103}N$, (d) acyl which may be substituted by $NO_2$, (e) $(R^{109})n_{102}$—$C_{6-14}$ aryl $R^{109}$: (i) H, (ii) OH, (iii) CN, (iv) $NO_2$, (v) COOH, (vi) Halo, (vii) oxo (=O), (viii) $R^{101}R^{103}N$, (ix) $C_{1-10}$ alkyl which may be substituted by $R^{110}$, $R^{110}$: H, OH, COOH, Halo, $C_{6-14}$ aryl, heterocycle-ylidene which may be substituted by ($C_{1-10}$ alkyl, oxo or thioxo (=S)), $C_{1-10}$ alkyl-O—, $C_{1-10}$ alkyl-O—CO— or acyl-O—, (x) acyl-O—, (xi) $C_{6-14}$ aryl which may be substituted by Halo, (xii) heterocyclic group which may be substituted by Halo, $C_{1-10}$ alkyl or Halo $C_{1-10}$ alkyl, and/or (xiii) $R^{111}$—$T^{102}$—

$R^{111}$: (i) H, (ii) $C_{3-8}$ cycloalkyl, (iii) $R^{101}R^{103}N$, (iv) $C_{6-14}$ aryl which may be substituted by Halo, $C_{1-10}$ alkyl, Halo $C_{1-10}$ alkyl or $C_{6-14}$ aryl which may be $C_{6-14}$ aryl, or (v) $C_{3-10}$ alkyl which may be substituted by Halo, COOH, $C_{1-10}$ alkyl-O—, $R^{101}R^{103}N$, $C_{6-14}$ aryl, heterocyclic group, heterocycle-ylidene, $C_{1-10}$ alkyl-O—CO— or acyl-O—

$T^{102}$: —O—, —CO—, —NR$^{101}$—, —O—CO—, —CONR$^{101}$—, —NR$^{101}$NR$^{101}$CO—, —O—CONR$^{111}$—, —S(O)$n_{101}$— or —S(O)$n_{101}$NR$^{101}$— and/or $R^{111b}$NC(NR$^{111b}$)NR$^{101}$—, $R^{111b}$: H or $C_{1-10}$ alkyl-O—CO—

(f) $(R^{112})n_{102}$-heterocyclic group, $R^{112}$: oxo, oxide or a group the same as $R^{109}$ (g) $C_{1-10}$ alkyl-O—CO—

(4) heterocyclic group-$C_{1-10}$ alkylidene which may be substituted by Halo, oxide, $C_{1-10}$ alkyl, $C_{1-10}$ alkyl-O— or $C_{1-10}$ alkyl-O—CO—$NR^{101}$—, (5) acyl which may be substituted by $R^{113}$ $R^{113}$: OH, COOH, CN, $NO_2$, Halo, $C_{6-14}$ aryl, heterocyclic group, $R^{101}R^{103}N$, $C_{1-10}$ alkyl, Halo $C_{1-10}$ alkyl, $C_{1-10}$ alkyl-O—, $C_{1-10}$ alkyl-O—CO—, $C_{1-10}$ alkyl-O—$C_{6-14}$ aryl, acyl, $C_{1-10}$ alkyl-O—CO—, $C_{1-10}$ alkyl-$C_{6-14}$ aryl, acyl-$NR^{101}$—, acyl-$NR^{101}$—$C_{6-14}$ aryl or $C_{1-10}$ alkyl-$C_{6-14}$ aryl-$SO_2$—$N^{101}$—, (6) $R^{101}R^{103}NCO$ (7) $R^{114}$—$S(O)n_{101}$—

$R^{114}$: (a) H, (b) $C_{1-10}$ alkyl which may be substituted by OH, $NO_2$, Halo, $R^{101}R^{103}N$, $C_{1-10}$ alkyl-O—, acyl-$NR^{101}$— or $C_{6-14}$ aryl, (c) $C_{6-14}$ aryl which may be substituted by OH, $NO_2$, Halo, $R^{101}R^{103}N$, $C_{1-10}$ alkyl, Halo $C_{3-10}$ alkyl, $C_{1-10}$ alkyl-O—, acyl-$NR^{101}$— or $C_{6-14}$ aryl, (d) heterocyclic group which may be substituted by OH, $NO_2$, Halo, $R^{101}R^{103}N$, $C_{1-10}$ alkyl, Halo $C_{1-10}$ alkyl, $C_{1-10}$ alkyl-O—, acyl-$NR^{101}$— or $C_{6-14}$ aryl, or (e) $R^{101}R^{103}N$, and/or (8) $R^{115}$—$T^{103}$ $R^{115}$: (a) $C_{1-10}$ alkyl which may be substituted by heterocyclic group, (b) $C_{6-14}$ aryl which may be substituted by heterocyclic group or $R^{101}R^{103}N$ or (c) heterocyclic group, $T^{103}$: —CO—$NR^{101}$—, —$NR^{101}$—CO—, —$NR^{101}$—CS—, —O—CO—O—, —O—CO— or —CO—CO—, the same shall apply hereinafter;

d group: (1) CN, (2) $NO_2$, (3) Halo, (4) OH, (5) COOH, (6) $C_{1-10}$ alkyl-$T^{104}$— which may be substituted by (OH, Halo, heterocyclic group, $C_{6-14}$ aryl which may be substituted by Halo, $R^{101}R^{103}N$, $R^{101}$—CO—, $R^{101}$—$T^{101}$—CO— or $R^{101}$—$T^{101}$—)

$T^{104}$: a bond, —O—, —CO—O—, —O—CO—, (7) acyl which may be substituted by $R^{113}$, (8) acyl-O— which may be substituted by $R^{113}$, (9) $R^{116}R^{117}N$ $R^{116}$, $R^{117}$: the same or different, H or a substituent of c group, and/or (10) $R^{116}R^{117}NCO$, the same shall apply hereinafter.)

In the active ingredients of the invention or the compounds of the invention, geometrical isomers and tautomers may exist, for example, as shown below.

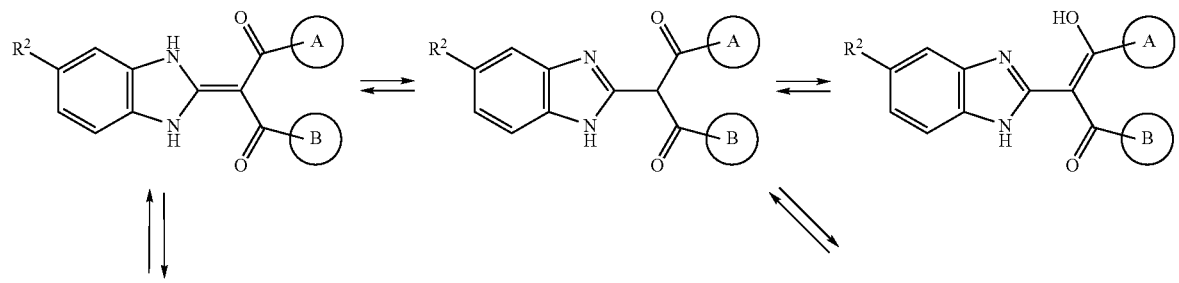

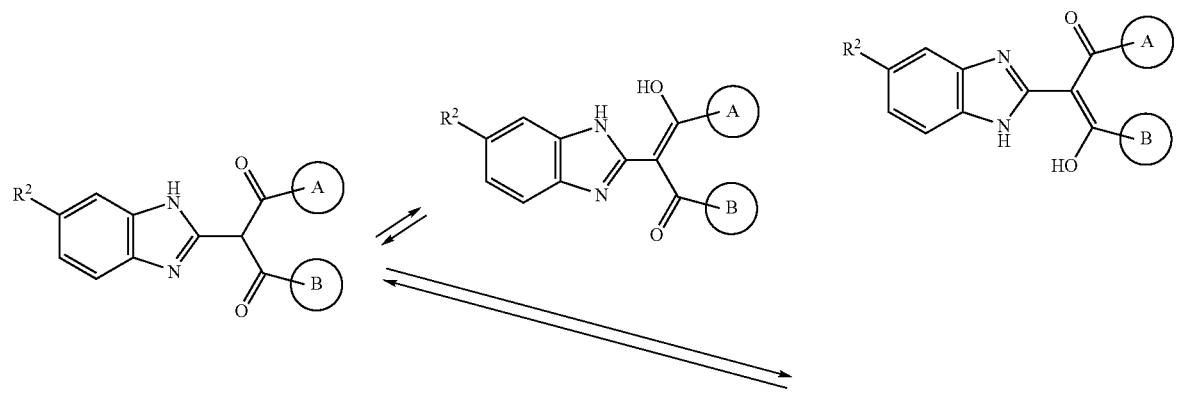

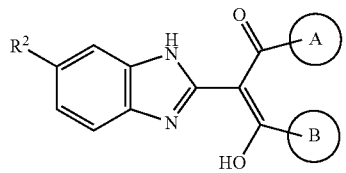

The invention includes separated or mixed forms of these isomers. In addition, depending on the kind of substituents, certain compounds of the invention may contain asymmetric atom(s) or axial asymmetry, and hence isomers based on the asymmetric carbon atom(s) or the like can exist. The invention includes mixed or separated forms of these optical isomers. Moreover, the invention also includes compounds labeled with a radioactive isotope.

In addition, among the compounds of the invention, there exist compounds wherein geometrical isomerism with regard to the double bond at 2-position of the propane can be mutually transformable as shown below through tautomerism as shown in the above.

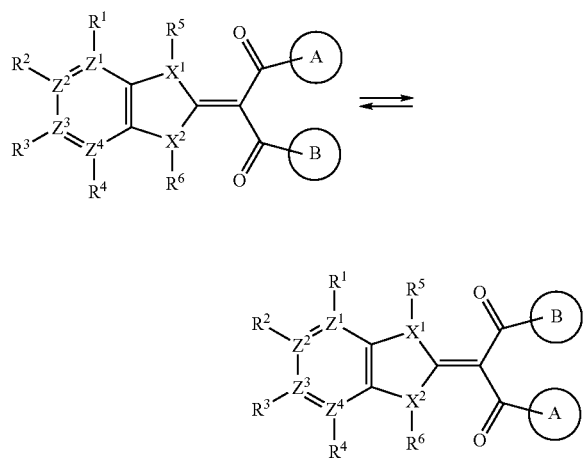

Furthermore, the active ingredients of the invention or the compounds of the invention also forms acid addition salts or salts with a base in some cases depending on the kinds of substituents, and such salts are also included in the invention so far as they are pharmaceutically acceptable salts. Specifically, there are mentioned acid addition salts with an inorganic acid such as hydrochloric acid, hydrobromic acid, hydroiodic acid, sulfuric acid, nitric acid or phosphoric acid or with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid or glutamic acid, salts with an inorganic base such as sodium, potassium, magnesium, calcium or aluminum or with an organic base such as methylamine, ethylamine, ethanolamine, lysine or ornithine, ammonium salts, and the like. Various hydrates and solvates of the active ingredients of the invention or the compounds of the invention are also included in the invention. In addition, polymorphic substances thereof are also included.

Moreover, the active ingredients of the invention or the compounds of the invention also include all the compounds which are metabolized and converted in the living body, so-called prodrugs. The groups forming the prodrugs of the invention include groups described in Prog. Med., 5, 2157-2161 (1985) and "Iyakuhin no Kaihatsu (Development of Pharmaceuticals)", Vol. 7 (Hirokawa Shoten, 1990), Bunshi Sekkei (Molecular Design), pp. 163-198 or the like.

(Production Methods)

The compounds of the invention and the pharmaceutically acceptable salts thereof can be produced by utilizing characteristics based on the fundamental skeleton or kind of substituents and applying various known synthetic methods.

At that time, depending on the kind of functional group, it may sometimes be effective from the viewpoint of production techniques to replace the functional group with an appropriate protective group (a group which can be easily converted into the functional group) at the stage of starting materials or synthetic intermediates. Examples of such functional groups include an amino group, a hydroxyl group, a carboxyl group and the like and examples of their protective groups include the protective groups which are described in "Protective Groups in Organic Synthesis (3rd edition)", written by Greene and Wuts, which may be optionally selected and used depending on the reaction conditions. In these methods, the reaction is carried out after introducing a protective group and then, if necessary, the protective group is removed to obtain the desired compound.

Moreover, when the active ingredients of the invention are known compounds, they can be easily available in accordance with the above literatures (Collect. Czech. Chem. Commun. (1971), 36(1), 150-163 and so forth).

The following will describe representative synthetic methods of the compounds of the invention or intermediates thereof.

The symbols in the following sentences are as follows. DMF: N,N-dimethylformamide; DMSO: dimethyl sulfoxide; THF: tetrahydrofuran; Tol: toluene; EtOAc: ethyl acetate; DCE: 1,2-dichloroethane; TEA: triethylamine; Diglyme: diethylene glycol dimethyl ether First Production Method (Acylation Reaction)

The present production method is a usual acylation, which is specifically carried out by reacting an alkyl compound with an equivalent amount of acyl compound in a solvent inert to the reaction at a room temperature to an elevated temperature.

The solvent inert to the reaction includes aromatic hydrocarbon solvents such as benzene or toluene, ether solvents such as Diglyme, THF, 1,4-dioxane or 1,2-dimethoxyethane, Halo hydrocarbon solvents such as dichloromethane, chloroform or DCE, basic solvents such as TEA, pyridine, collidine, morpholine or 2,6-lutidine, and the like. These solvents are used solely or as a mixture of two or more of them. Optionally, an inorganic base such as sodium hydride may be added.

As an representative example, the compound of the invention is produced by reacting a methylimidazole compound (II) with an acyl compound (III) in a solvent inert to the reaction at a room temperature to an elevated temperature (Step i) to obtain an intermediate (IV) or the like and by adding an equivalent amount of a carboxylic acid (V) to the compound (IV) and heating them (Step ii).

In the production method, the reaction can be also effected by adding an equivalent amount of a carboxylic acid (V) or an equivalent amount of water after the first step without isolating the intermediate (IV) or the like and heating them as above. Moreover, an acid anhydride of the acyl compound (III) may be used instead of the compound.

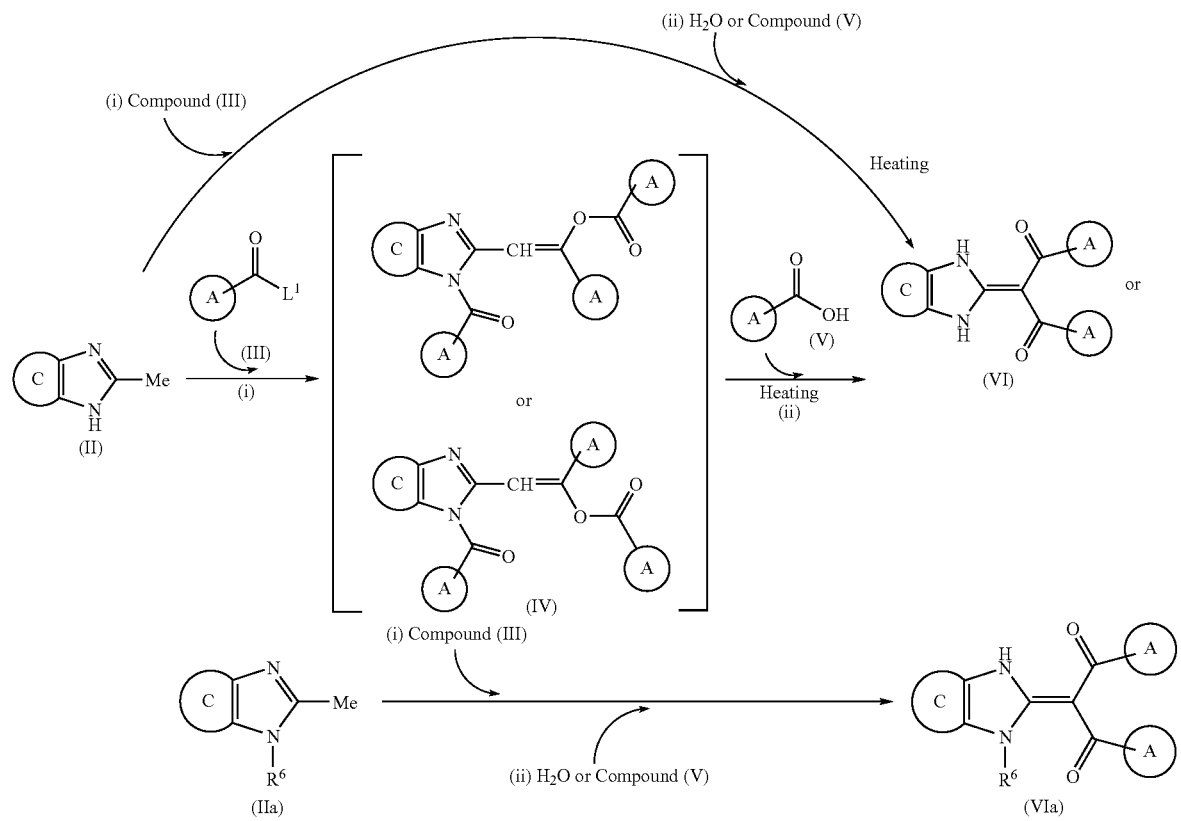

(wherein the symbol $L^1$ in the formula represents a leaving group, the above

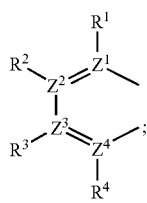

represents $$R^2\underset{Z^2}{\overset{Z^1}{\diagdown}}\underset{Z^3}{\overset{R^1}{\diagup}}\underset{Z^4}{\overset{}{\diagdown}}R^3\underset{R^4}{\overset{}{\diagup}};$$

the same shall apply hereinafter)

The leaving group $L^1$ includes Halo, or an organic sulfonic acid residue such as methanesulfonyloxy or p-toluenesulfonyloxy.

Second Production Method

The production method is carried out by reacting an ester compound (VII) with an acyl compound (VIII) to obtain a diketone compound (IX), by reacting the compound (IX) with carbon disulfide and adding an alkyl halide to obtain a dithioacetal compound (X), and finally by reacting the compound (X) with an amine compound (XI).

The compound of the invention (XII) is obtained by reacting the ester compound (VII) with an equivalent amount of the acyl compound (VIII) in the presence of a base such as sodium hydride in a solvent inert to the reaction, such as THF, at a room temperature to an elevated temperature (Step i), reacting the resulting compound (IX) with carbon disulfide in the presence of an inorganic base such as KF/$Al_2O_3$ or potassium carbonate or an organic base such as TEA at a temperature of cooled temperature to room temperature, preferably 0° C. to room temperature, then adding an alkylating agent such as methyl iodide or 1,3-dibromopropane to effect alkylation reaction (Step ii), and finally reacting the resulting dithioacetal compound (X) with an equivalent amount of the amine compound (XI) in a solvent inert to the reaction, such as ethanol or DMSO, at a room temperature to under heating with refluxing (Step iii).

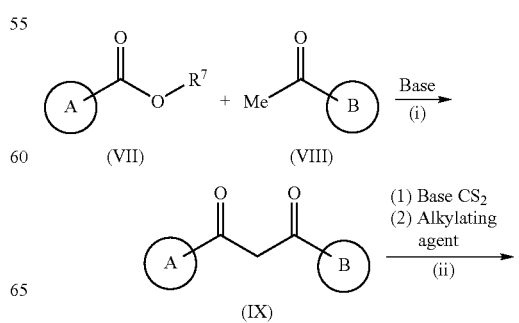

-continued

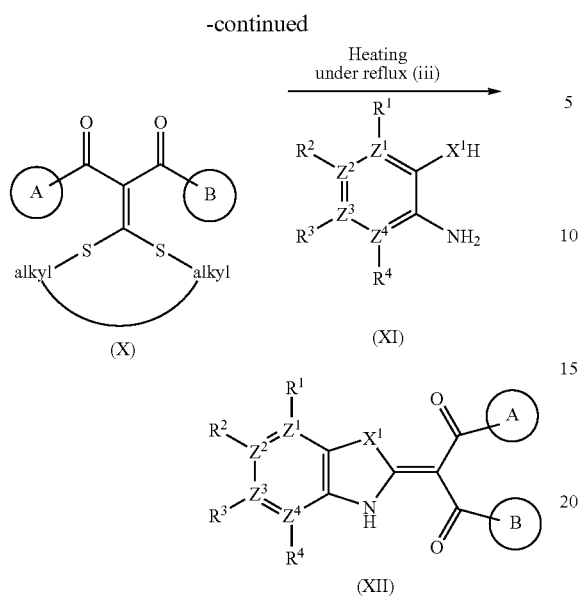

(wherein $R^7$ represents a $C_{1-6}$ alkyl and $X^1$ represents NH, O or S, and a dotted line represents possible formation of a ring through combination of the two alkyl groups)

Third Production Method

The production method is carried out by reacting the 2-methylimidazole compound (II) with the acyl compound (III) (Step i), obtaining an imidazole compound (XIV) in the presence of an organic base such as morpholine in a solvent inert to the reaction at a room temperature to an elevated temperature (Step ii), and acylating the compound (XIV) with an acyl compound (XV) (Step iii). Step i and Step iii are carried out in accordance with the acylation in the above First production method. The intervening intermediate (XIII) or the like may be isolated or may not be isolated.

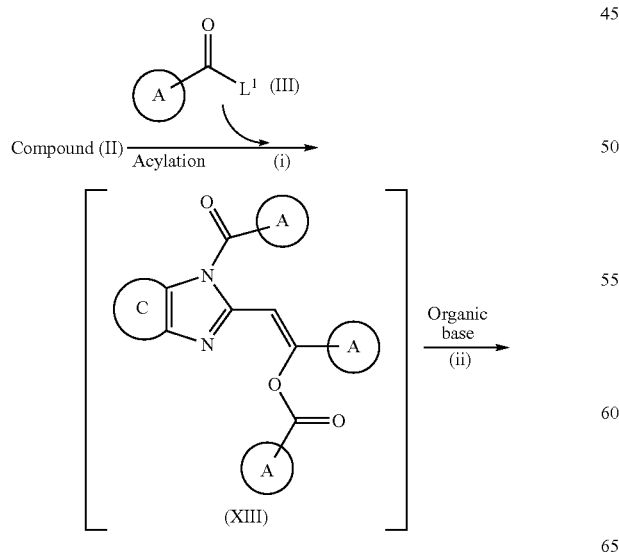

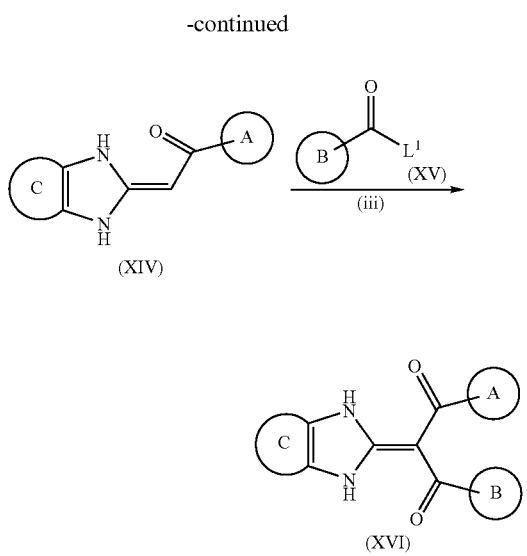

Fourth Production Method (Reduction Reaction)

The reduction reaction is carried out according to well-known methods (COMPREHENSIVE ORGANIC SYNTHESIS 8 REDUCTION (Pergamon Press)(1991)). More preferably, it is carried out by (1) catalytic reduction under hydrogen atmosphere or in the presence of hydrogen donor such as ammonium formate using palladium (Pd), platinum (Pt), nickel (Ni), or the like in a solvent such as methanol, ethanol, chloroform, EtOAc or acetic acid at a room temperature to an elevated temperature, (2) using a metal such as Fe or $SnCl_2$ in the presence of an acid such as acetic acid, hydrochloric acid or the like, or using a reducing agent such as sodium hydrosulfite in an mixed solvent such as water and MeOH or THF at a room temperature to an elevated temperature, or (3) adding a reducing agent such as sodium borohydride, sodium cyanoborohydride or sodium triacetoxyborohydride in a solvent inert to the reaction, such as ethanol, at a temperature of ice-cooling to an elevated temperature.

As a representative example, there may be mentioned a reaction from a nitro compound (XVII) to an amine compound (XVIII) or a reaction from a ketone compound (XIX) to an alcohol compound (XX).

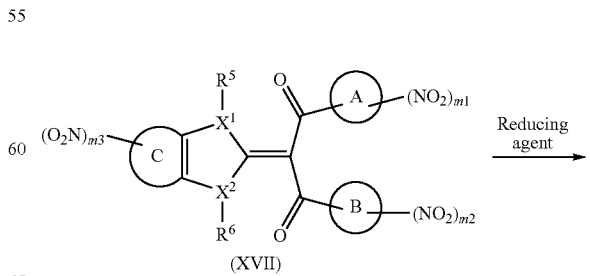

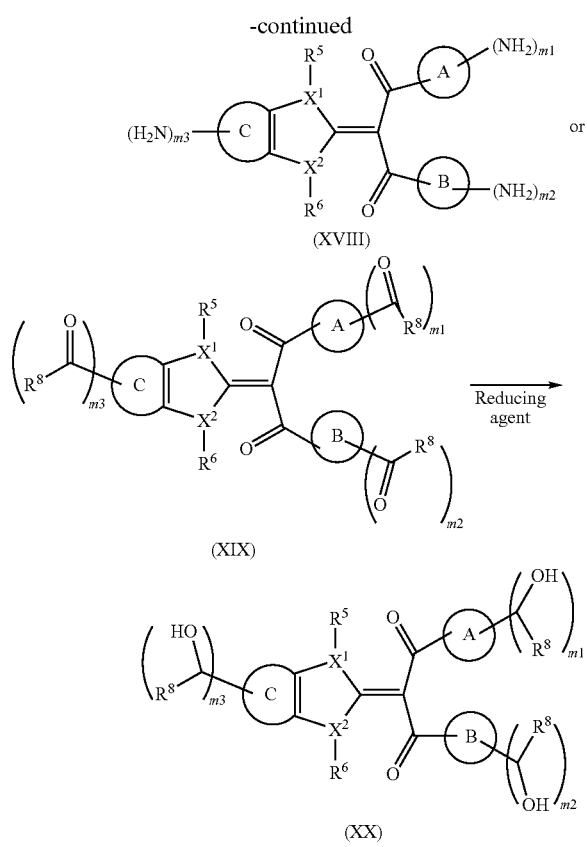

(the symbol $R^8$ in the formulae is a hydrocarbon group which may be substituted or a heterocyclic group which may be substituted, m1 or m2 is the same or different and represents an integer of 0 to 5, m3 represents an integer of 0 to 4, and they satisfies $m1+m2+m3 \geqq 1$; the same shall apply hereinafter)

Fifth Production Method

The reaction is carried out by stirring an amine compound and an equivalent amount of an aldehyde compound in the presence or absence of an acid such as p-toluenesulfonic acid in a solvent inert to the reaction, such as ethanol, benzene, THF or Tol at a room temperature to an elevated temperature to obtain an imine compound, and then subjecting it to reduction reaction in accordance with the above fourth production method, preferably the reaction (1) or (3).

Alternatively, the reaction is carried out by mixing an amine compound and an equivalent amount of an aldehyde compound and adding a reducing agent in accordance with Fourth production method. The reducing agent may be added immediately after the mixing of the amine compound and the aldehyde compound or at an interval of some period of time. A ketone or 1-hydroxymethylbenzotriazole may be used instead of the aldehyde compound. As representative examples, there may be mentioned a reaction from an amine compound (XVIII) and an aldehyde compound (XXI) to an alkylamino compound (XXII) and a reaction from the amine compound (XVIII) to the alkylamino compound (XXII) via an imine compound (XXIII).

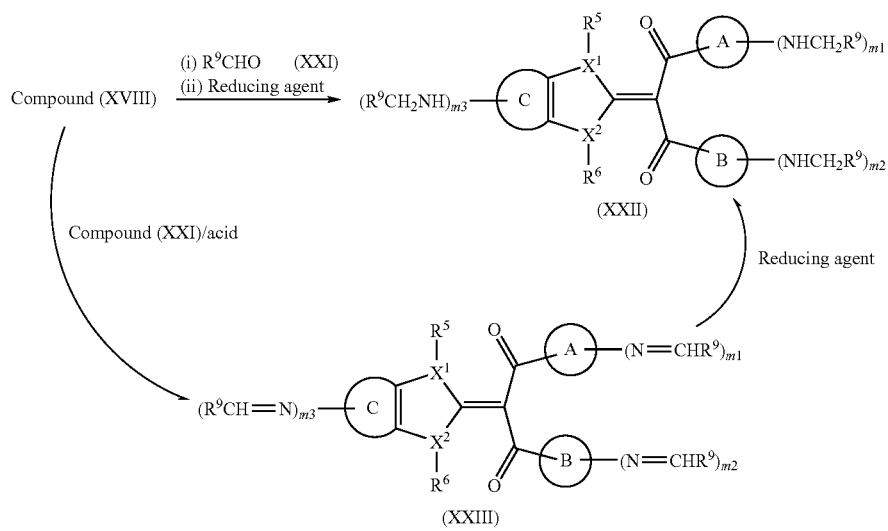

(wherein $R^9$ represents the following meaning. $R^9$: $R^{10}$—$T^1$—$R^{10}$: H; $R^{107}$;

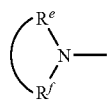

($R^e$, $R^f$: the same or different, hydrogen atom, or a substituent of the above c group, a dotted line: $R^e$ and $R^f$ may be combined to form the above heterocycle (the same shall apply hereinafter); or a $C_{1-15}$ hydrocarbon group which may have 1 to 5 functional groups selected from the group consisting of $C_{1-10}$ alkyl-CONH—, $C_{1-10}$ alkyl, $C_{1-10}$ alkyl-O—, and a carboxy which may be substituted by a substituent of the above b group, $T^1$: $C_{1-10}$ alkyl, $C_{2-10}$ alkenyl, $C_{2-10}$ alkynyl or a single bond, the same shall apply hereinafter)

Sixth Production Method (Amidation or Sulfonamidation Reaction)

The reaction is carried out according to usual methods. For example, it is carried out according to a method using a condensing reagent (dicyclohexylcarbodiimide, 1-ethyl-3-(3'-dimethylaminopropyl)carbodiimide, 1,1'-carbonyldiimidazole, or the like) or a mixed acid anhydride method using ethyl chloroformate, isobutyl chloroformate, or the like.

Moreover, it is possible that a carboxylic acid or a sulfonic acid is converted into a reactive derivative such as an acid halide with a halogenating agent such as thionyl chloride, oxalyl chloride or phosphorus oxychloride and then the derivative is reacted with an amine compound. The reaction is usually suitably carried out in a solvent inert to the reaction, such as THF, DMF, dichloromethane, chloroform, acetonitrile or EtOAc in the presence of, if necessary, an organic base such as TEA or an inorganic base such as potassium carbonate under cooling (preferably −15 to 0° C.) or at room temperature or under heating.

As a representative example, there may be mentioned a reaction from the amine compound (XVIII) and a carboxylic acid (XXIV) or a reactive derivative thereof or a sulfonic acid (XXVI) or a reactive derivative thereof to an amide compound (XXV) or a sulfonamide compound (XXVII).

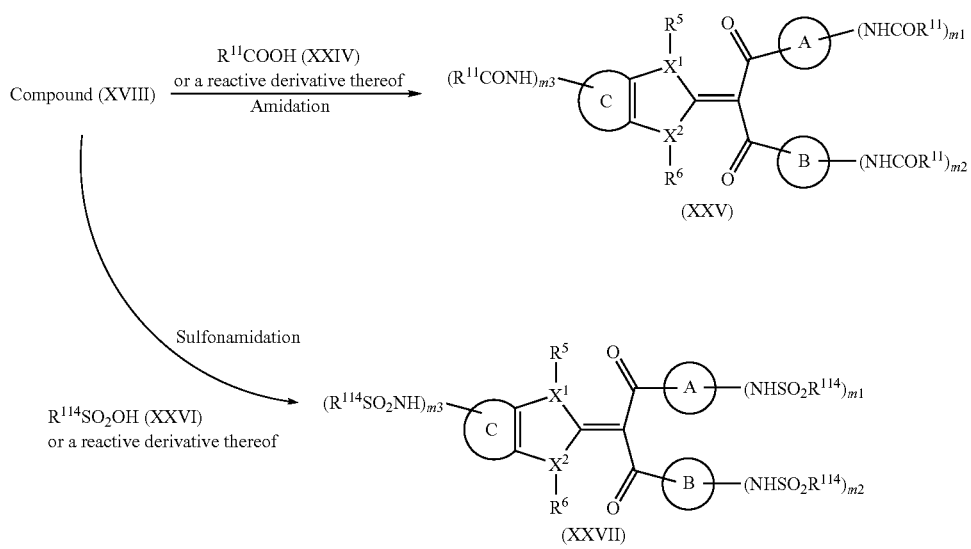

(the symbol in the formulae represents the following meaning. $R^{11}CO$: an acyl which may be substituted by $R^{113}$, the same shall apply hereinafter)

Seventh Production Method

The production method is carried out by reacting a compound having a leaving group with an equivalent amount of an amine compound, a compound having a hydroxy (OH) group or a sulfonamide compound in a solvent inert to the reaction, such as THF, acetone, DMF, acetonitrile, dichloromethane, methanol or DMSO, under cooling or at a room temperature to an elevated temperature, or under refluxing. Optionally, an inorganic base such as potassium carbonate or an organic base such as TEA may be added.

As representative examples, there may be mentioned an amination reaction from an alkyl compound having a leaving group L2 (XXVIII) and an amine compound (XXIX) to an compound of the invention (XXX) or an O-alkylation reaction from an alkyl compound having a leaving group L2 (XXXIV) and a hydroxyl compound (XXXIII) to a compound of the invention (XXXV).

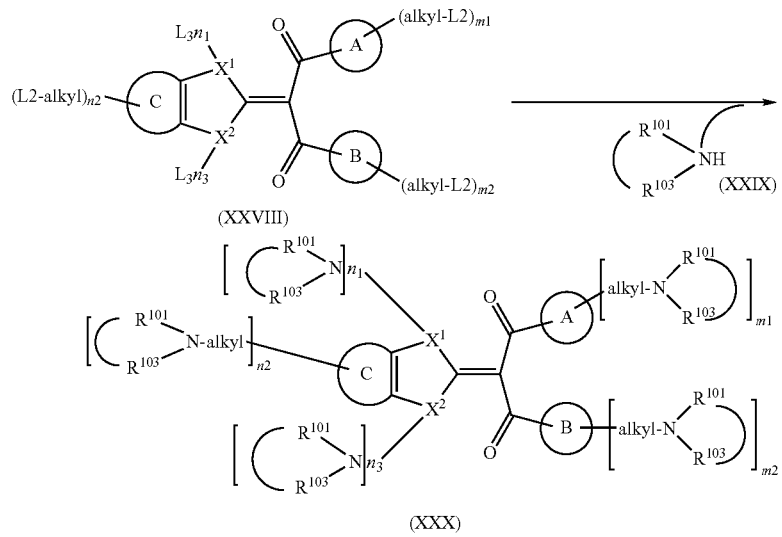

(the symbols in the formulae are as follows. L2: the above L1 or a diazo group (N=N—), L3: chlorine (Cl) or bromine (Br), n1, n3: the same or different, an integer of 0 to 1, n2: an integer of 0 to 4, provided that m1+m2+n1+n2+n≧1 (the same shall apply hereinafter), or

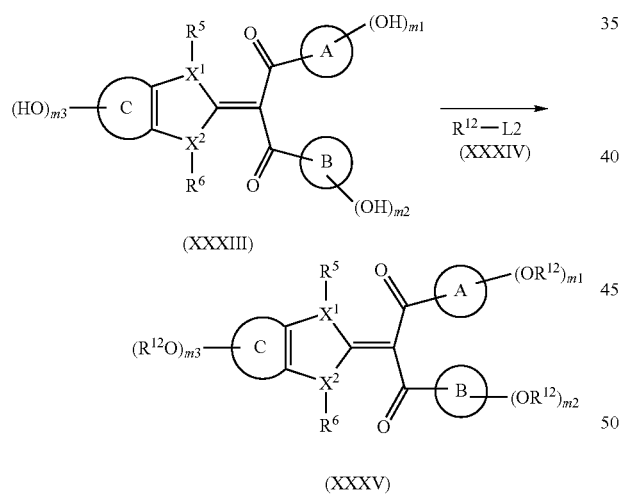

(the symbol $R^{12}$ in the formulae is a substituent of b group, the same shall apply hereinafter)

Eighth Production Method

The present hydrolysis reaction is carried out in the presence of an inorganic base such as potassium carbonate, more preferably an organic base such as morpholine in a solvent inert to the reaction at a room temperature to under heating with refluxing.

As a representative example, there may be mentioned a hydrolysis reaction from a compound (XXXI) to a compound (XXXII).

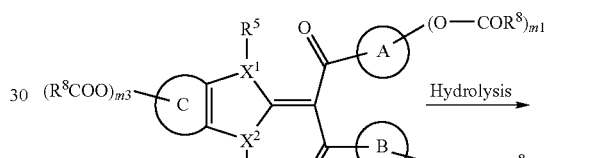

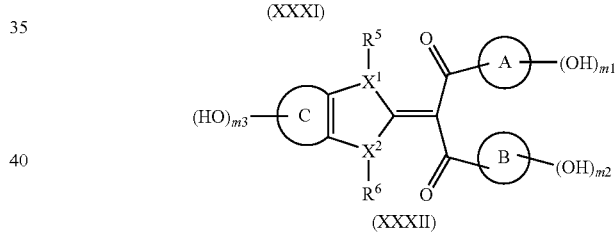

Ninth Production Method

The production method is carried out by reacting an amine compound with an equivalent amount of an isocyanate compound or an isothiocyanate compound in a solvent inert to the reaction such as Tol, acetonitrile, chloroform or DMF at a temperature of 0° C. to under refluxing.

The isocyanate compound is obtained by subjecting a carboxylic acid or a reactive derivative thereof (e.g., an acid chloride), which is a starting material of the isocyanate compound, to well-known rearrangement reaction (ADVANCED ORGANIC CHEMISTRY written by J. March (John Willy & Sons (1992)). The isothiocyanate compound is obtained by subjecting an amine compound, alkyl halide, diazonium salt or isocyanide, which is a starting material of the isocyanate compound, to a well-known reaction (ADVANCED ORGANIC CHEMISTRY written by J. March (John Willy & Sons (1992)).

The isocyanate compound or isothiocyanate compound is obtained by the above reaction, and the compound may be subjected to a urea-forming reaction or thiourea-forming reaction in situ, or the isocyanate compound or isothiocyanate compound may be subjected to a urea-forming reaction or thiourea-forming reaction after once isolated. Alternatively, the production method is carried out by reacting an amine compound with an equivalent amount of a carbodiimide compound instead of the isocyanate compound or isothiocyanate compound in a solvent inert to the reaction at a room temperature to an elevated temperature and then subjecting the product to a deprotection reaction. The carbodiimide compound is synthesized by a well-known reaction (Fieser and Fieser's Reagent for Organic Synthesis, Vol. 8 (Wiley) p. 96). The carbodiimide compound may be protected with an appropriate protective group. The protective group and deprotection reaction are in accordance with the above "Protective Groups in Organic Synthesis (third edition)".

As representative examples, there may be mentioned a reaction from an amine compound (XXXVI) and an isocyanate compound or isothiocyanate compound to a urea compound (XXXVII) or thiourea compound (XXXVIII) or a reaction from the amine compound (XXXVI) and a carbodiimide compound (XXXIX) to a guanidine compound (XXXXI).

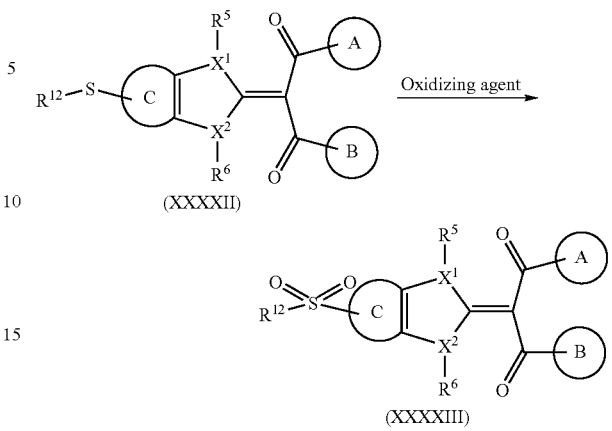

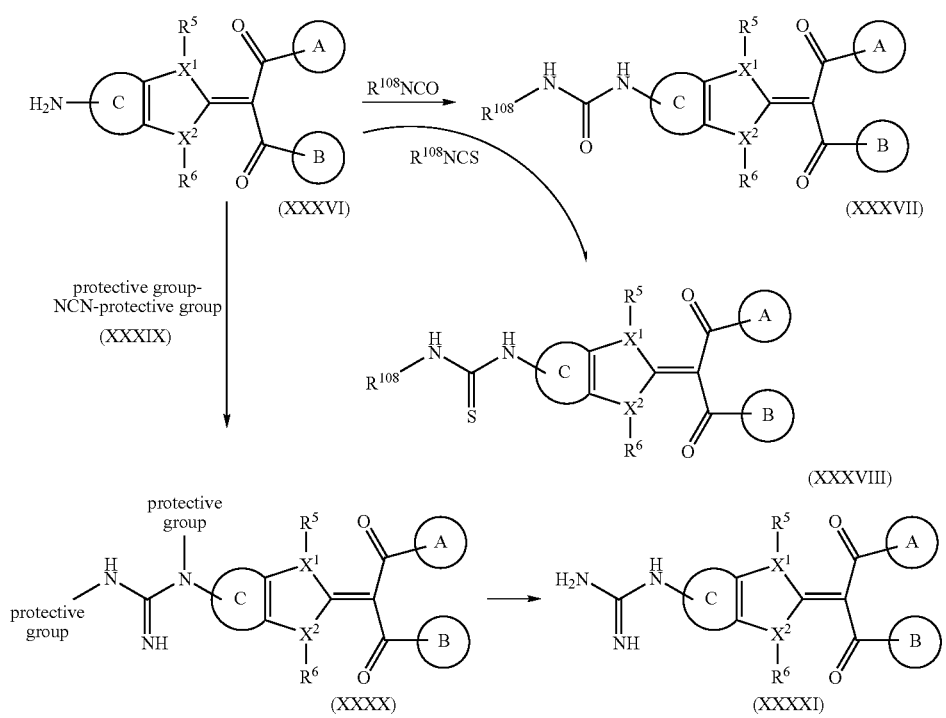

Tenth Production Method

The present oxidation reaction is carried out according to well-known methods (ADVANCED ORGANIC CHEMISTRY written by J. March (John Willy & Sons (1992)). It is preferably carried out in a solvent inert to the reaction such as dichloromethane, chloroform, or the like in the presence of an oxidizing agent such as m-chloroperbenzoic acid (mcpba), hydrogen peroxide or tetrapropylammonium perruthenate (TPAP).

As representative examples, there may be mentioned a reaction from a sulfide compound (XXXXII) and an oxidizing agent to a sulfonyl compound (XXXXIII), a reaction of an alcohol compound to an aldehyde compound, or a reaction from a pyridylmethylamino compound to an N-oxidopyridylmethylideneamino compound.

It is noted that each reaction scheme described in the above production methods show a reaction of a representative compound. Therefore, when the same substituent is present in the compounds of the invention at a position other than the position in the reaction scheme, the compounds included in the scope of the invention can be easily produced by the substituent-modifying reaction using the above reaction scheme.

Moreover, when the starting compounds are novel, they may be obtained by the following production methods.

Production Method 1

The production method is carried out by condensing an aldehyde compound or ketone compound with an equivalent amount of an active methylene compound in the presence of a base or an acid catalyst at a room temperature to an elevated temperature.

Acetic acid is used as a solvent, a secondary amine such as piperidine is preferably employed as the base, and a salt such as ammonium chloride or potassium fluoride or a Lewis acid such as $TiCl_4$ is used as the acid catalyst.

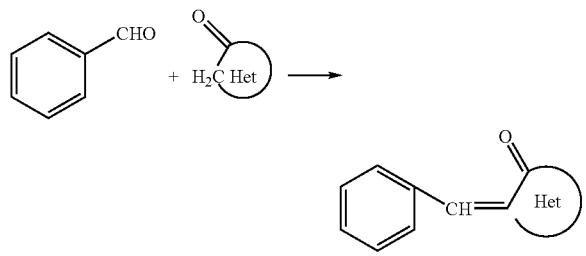

(wherein

is a heterocycle having oxo and active methylene, which may be substituted by $C_{1-10}$ alkyl and/or thioxo)

Production Method 2

The production method is carried out by reacting a nitrobenzene compound having a leaving group $L^1$ with an equivalent amount of ammonia in a solvent inert to the reaction, such as methanol, at a room temperature to an elevated temperature in a sealed tube.

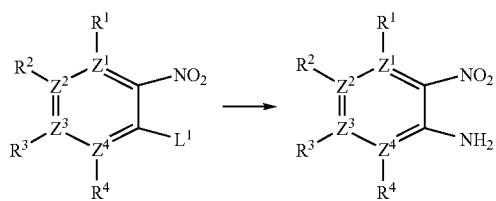

Production Method 3

The production method is effected by reacting an aldehyde compound or ketone compound with an equivalent amount of a phosphorus ylide in a solvent inert to the reaction, such as DMF, at a temperature of 0° C. to an elevated temperature. The phosphorus ylide may be prepared from a corresponding phosphonium salt and a base such as sodium hydride according to well-known methods (ADVANCED ORGANIC CHEMISTRY written by J. March (John Willy & Sons (1992)).

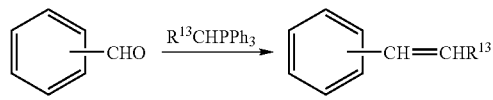

(wherein $R^{13}$ is a heteroaryl or a hydrocarbon group which may be substituted)

Production Method 4

The production method is carried out by reacting a 1,2-phenylenediamine compound with a trialkyl orthoacetate compound in a solvent inert to the reaction, such as ethanol, at a room temperature to under refluxing. As occasion demands, an acid catalyst such as hydrochloric acid may be added, or water may be removed from the reaction system by adding molecular sieves or using the Dean-Stark apparatus.

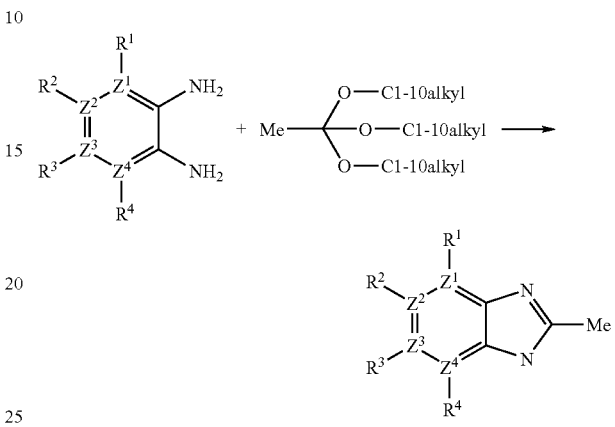

Alternatively, the production method is carried out by cyclization-condensation of an o-aminoacetanilide compound obtainable by carrying out a reduction reaction in accordance with the Fourth production method in the presence or absence of an acid catalyst such as acetic acid or hydrochloric acid. At that time, the resulting o-aminoacetanilide compound may be isolated or may not be isolated.

Production Method 5

The production method is carried out by reacting a halobenzene compound with a phenylborane compound in the presence of a palladium catalyst such as tris(dibenzylideneacetone)dipalladium or the like and a ligand such as tris-t-butylphosphine or the like and a base such as cesium carbonate in a solvent inert to the reaction, such as dioxane, at a room temperature to an elevated temperature (Angew. Chem. Int. Ed., 37, 3388 (1998)). The reaction is preferably carried out under an atmosphere of an inert gas such as nitrogen gas or argon. (substituent of a group)$n_{102}$ (substituent of a group) $n_{102}$

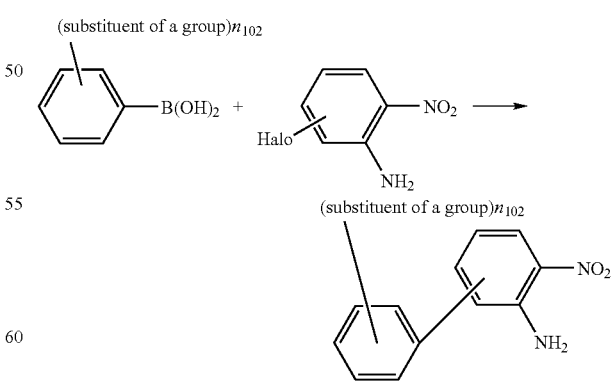

Production Method 6

The production method is carried out by reacting an amine compound, amide compound or imide compound with an equivalent amount of a bromine compound in a solvent inert to the reaction, such as a Halo hydrocarbon solvent such as tetrachloromethane or DCE or an aromatic hydrocarbon solvent such as benzene at a temperature of 0° C. to under refluxing. The bromine compound includes N-bromosuccinimide, bromine, tBuOBr, AcOBr, and the like. Optionally, a radical initiator such azobisisobutyronitrile (AIBN) may be added.

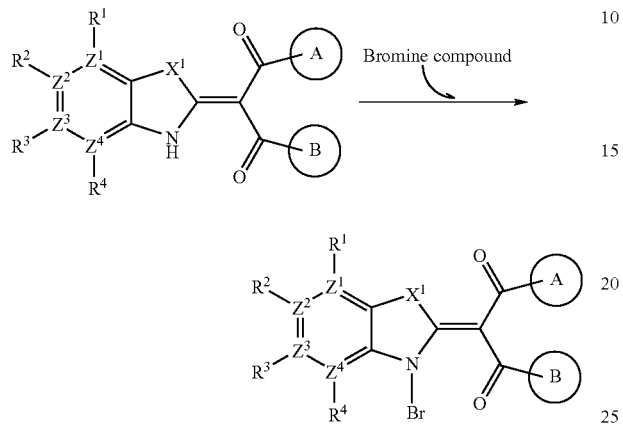

The compounds of the invention are isolated and purified as free compounds, pharmaceutically acceptable salts thereof, hydrates, solvates or polymorphic substances. The pharmaceutically acceptable salts of the compounds of the invention (I) can be also produced by subjecting the compound to a usual salt-forming reaction.

Isolation and purification are carried out by applying general chemical operations such as extraction, fractionating recrystallization, various types of fractionating chromatography and the like.

Each form of isomers can be separated by selecting an appropriate starting compound or making use of physicochemical differences among isomers. For example, optical isomers can be made into stereochemically pure isomers by selecting appropriate starting compounds or a conventional optical resolution method (e.g., a method in which they are converted into diastereomer salts with a general optically active base or acid and then subjected to optical resolution).

In a similar manner to those described in the production methods, the Example compounds described in the following tables are obtained. Also, part of the compounds in the following tables were obtained.

In this connection, abbreviations herein indicate as follows.

Rex: Reference Example; Ex: Example; Str: structural formula; Dat: physicochemical properties; FA: FAB-MS (M+H)$^+$; MS: found value on mass spectrometry; FN: FAB-MS (M−H)$^−$; EI: EI-MS; N1: NMR (DMSO-d$_4$, TMS internal standard) characteristic peaks δ ppm; N2: NMR (CDCl$_3$, TMS internal standard) characteristic peaks δ ppm; Ph: phenyl; Me: methyl; diMe: dimethyl; Et: ethyl; Pr: propyl; iPr: isopropyl; iBu: isobutyl; Pen: pentyl; cPr: cyclopropyl; Ac: acetyl; Cl: chloro; diCl: dichloro; CN: cyano; F: fluoro; diF: difluoro; triF: trifluoro; NO$_2$: nitro; MeO: methoxy; diMeO: dimethoxy; Br: bromo; diBr: dibromo; CF$_3$: trifluoromethyl; AcO: acetoxy; MeOCO: methoxycarbonyl; Boc: tert-butoxycarbonyl; NH$_2$: amino; PhCONH: benzoylamino; EtCONH: ethylcarbonylamino; Et$_2$N: diethylamino; TBS: tert-butyldimethylsilyl; biph: biphenyl; Naph: naphthalene: Thiop: thiophene; Fu: furan; Py: pyridine; IM: imidazole; Pyrazi: pyrazine; Pipe: piperidine; Pyrazo: pyrazole; Pyrim: pyrimidine; Pyrr: pyrrole; Pyrroli: pyrrolidine; Mo: morpholine; Isoquin: isoquinoline; Isoind: isoindoline; Thiaz: thiazole; Tr: triphenylmethyl; TEA: triethylamine; NMO: N-methylmorpholine oxide; TPAP tetrapropylammonium perruthenate; Sa: addition salt; HCl: hydrochloride; Oxal: oxalate; MS4A: molecular sieves 4A.

TABLE 2

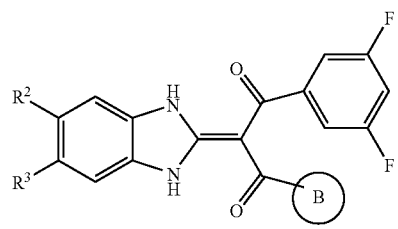

| Compound No. | R$^2$ | R$^3$ | B |
|---|---|---|---|
| 1a | H | Py-3-ylCH$_2$NHCH$_2$ | Ph |
| 2a | H | MeOCOCH$_2$ | Ph |
| 3a | H | Py-3-ylCH$_2$NHCH$_2$ | Ph |
| 4a | H | Me$_2$NCOCH$_2$ | Ph |
| 5a | H | 4-AcNH-PhCH$_2$NH | Ph |
| 6a | H | MeCH(Ph)NH | Ph |
| 7a | Py-3-ylCH$_2$NHCH$_2$ | MeO | Ph |
| 8a | H | Py-3-ylCH$_2$NH | 3-H$_2$N-Ph |
| 9a | H | Py-3-ylCH$_2$NH | Py-3-yl |
| 10a | H | 4-O$_2$N-PhCONH | 3-H$_2$N-Ph |
| 11a | H | Me[MeO(CH$_2$)$_3$]NCH$_2$ | Ph |
| 12a | MeO | Py-3-ylCH$_2$NHCH$_2$ | Ph |

TABLE 3

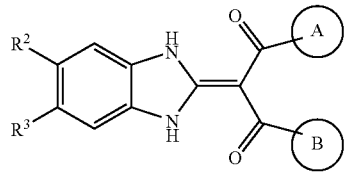

| Compound No. | R$^2$ | R$^3$ | A | B |
|---|---|---|---|---|
| 13a | 1,3-Thiaz-5-ylCH$_2$NH | H | 3,5-diF-Ph | 3-Me-Ph |
| 14a | O$_2$N | Cl | 3,5-diF-Ph | 3-Me-Ph |
| 15a | H | F | Ph | 4-cPrNH-Ph |
| 16a | MeO | MeO | 3-HOOC-Ph | Ph |
| 17a | H | H | 3,5-diF$_3$C-Ph | 3-H$_2$N-Ph |
| 18a | 4-F-PhCONH | H | Ph | Ph |
| 19a | 4-F-PhCONH | H | Ph | 3,5-diF-Ph |
| 20a | H | H | 4-F-Ph | 4-F-Ph |

TABLE 4

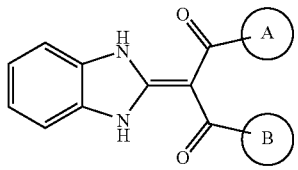

| Compound No. | A | B |
|---|---|---|
| 21a | 4-Cl-Ph | 4-Cl-Ph |
| 22a | 4-CN-Ph | 4-CN-Ph |
| 23a | 4-Me-Ph | 4-Me-Ph |
| 24a | 4-O$_2$N-Ph | 4-O$_2$N-Ph |
| 25a | 4-MeOCO-Ph | 4-MeOCO-Ph |
| 26a | 2-Cl-Ph | 2-Cl-Ph |
| 27a | 3-Cl-Ph | 3-Cl-Ph |
| 28a | 4-Cl—CH$_2$-Ph | 4-Cl—CH$_2$-Ph |
| 29a | 2-F-Ph | 2-F-Ph |
| 30a | 4-MeO-Ph | 4-MeO-Ph |
| 31a | 3-MeO-Ph | 3-MeO-Ph |
| 32a | 3-Br-Ph | 3-Br-Ph |
| 33a | 3-Me-Ph | 3-Me-Ph |
| 34a | 3-Et-Ph | 3-Et-Ph |
| 35a | Ph | 3-F-Ph |
| 36a | 3-H$_2$N-Ph | 3-H$_2$N-Ph |
| 37a | 3-(Py-3-ylCH$_2$CONH)Ph | 3,5-diF-Ph |
| 38a | 4-(Mo-4-ylCH$_2$)Ph | 4-(Mo-4-ylCH$_2$)Ph |
| 39a | 3-OH-Ph | 3-OH-Ph |
| 40a | 3,5-diF-Ph | Py-3-ylCH$_2$NHPh |

TABLE 5

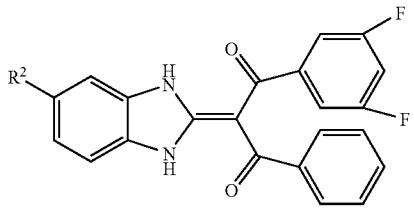

| Compound No. | R$^2$ |
|---|---|
| 41a | Py-3-ylCH$_2$NHCH$_2$ |
| 42a | MeOCOCH$_2$ |
| 43a | Me[MeO(CH$_2$)$_3$]NCH$_2$ |
| 44a | Py-3-ylCH$_2$NHCH$_2$ |
| 45a | Me$_2$NCOCH$_2$ |
| 46a | 4-AcNH-PhCH$_2$NH |
| 47a | MeCH(Ph)NH |
| 48a | 6-CF$_3$-Py-3-ylCH$_2$NH |
| 49a | 4-tBuOCONH-Py-3-ylCH$_2$NH |
| 50a | 2-Cl-Py-3-ylCH$_2$NH |
| 51a | 4-H$_2$N-Py-3-ylCH$_2$NH |
| 52a | 6-Me-Py-2-ylCH$_2$NH |
| 53a | 3-Cl-4-F$_3$C-Py-2-ylCH$_2$NH |
| 54a | 4,6-diMe-Py-2-ylCH$_2$NH |
| 55a | 5-CN-6-MeS-Py-2-ylCH$_2$NH |
| 56a | 3,6-diCl-4-OH-Py-2-ylCH$_2$NH |
| 57a | Py-2-ylCH$_2$NH |
| 58a | Py-4-ylCH$_2$NH |
| 59a | 2,6-diCl-Py-4-ylCH$_2$NH |
| 60a | 3,5-diOH-2-Me-Py-4-ylCH$_2$NH |
| 61a | Py-4-yl-CONH |
| 62a | 3-MeO—CO-PhCONH |
| 63a | 4-(iPrNHCO)PhCH$_2$NH |
| 64a | 1-Me-IM-4-ylCH$_2$NH |
| 65a | Py-2-ylCH$_2$NH |
| 66a | 6-Br-imidazo[1,2-a]Py-3-ylCH$_2$NH |
| 67a | 3-Cl-PhCH$_2$NH |
| 68a | 3-Br-PhCH$_2$NH |

TABLE 5-continued

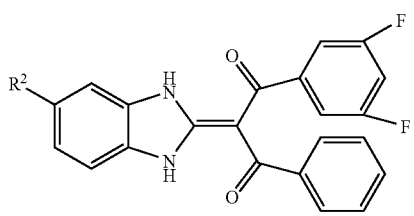

| Compound No. | R$^2$ |
|---|---|
| 69a | 4-Cl-PhCH$_2$NH |
| 70a | Naph-1-yl-CH$_2$NH |
| 71a | 2-Me-PhCH$_2$NH |
| 72a | 3-Me-PhCH$_2$NH |
| 73a | 4-iPr-PhCH$_2$NH |
| 74a | 4-Et-PhCH$_2$NH |
| 75a | 2-MeO-PhCH$_2$NH |
| 76a | 4-MeO-Naph-1-yl-CH$_2$NH |
| 77a | 4-MeO-3,6-diMe-PhCH$_2$NH |
| 78a | 3,5-diBr-6-HO-PhCH$_2$NH |
| 79a | 2-CF$_3$-PhCH$_2$NH |
| 80a | 3-Cl-PhCH$_2$NH |
| 81a | 4-Cl-PhCH$_2$NH |
| 82a | 2-Br-PhCH$_2$NH |
| 83a | 2-F-PhCH$_2$NH |
| 84a | 3-F-PhCH$_2$NH |
| 85a | 4-F-PhCH$_2$NH |
| 86a | 2-HO-PhCH$_2$NH |
| 87a | 3-HO-PhCH$_2$NH |
| 88a | 2-O$_2$N-PhCH$_2$NH |
| 89a | 3,5-diMeO-PhCH$_2$NH |
| 90a | 2,5-diMeO-PhCH$_2$NH |
| 91a | 2,3-diMeO-PhCH$_2$NH |
| 92a | 3,4-diF-PhCH$_2$NH |
| 93a | 2,4-diF-PhCH$_2$NH |
| 94a | Fu-2-ylCH$_2$NH |
| 95a | 5-Me-Fu-2-ylCH$_2$NH |
| 96a | 4-iBu-PhCH$_2$NH |
| 97a | 4-Br-PhCH$_2$NH |
| 98a | 3-MeO—CO-PhCH$_2$NH |
| 99a | 4-CN-PhCH$_2$NH |
| 100a | 3-PhCH$_2$O-PhCH$_2$NH |
| 101a | 2-Cl-4-F-PhCH$_2$NH |
| 102a | 2-Cl-5-HO-PhCH$_2$NH |
| 103a | 3-Cl-4-MeO-PhCH$_2$NH |
| 104a | 3-Cl-6-O$_2$N-PhCH$_2$NH |
| 105a | 4-Cl-5-O$_2$N-PhCH$_2$NH |
| 106a | 2,3-diHO-PhCH$_2$NH |
| 107a | 2,4-diHO-PhCH$_2$NH |
| 108a | 4,5-diHO-PhCH$_2$NH |
| 109a | 3-HO-4-MeO-PhCH$_2$NH |
| 110a | 3-HO-5-O$_2$N-PhCH$_2$NH |
| 111a | 3-HO-4-O$_2$N-PhCH$_2$NH |
| 112a | 2-HO-6-MeO-PhCH$_2$NH |
| 113a | 4-MeO-PhCH$_2$NH |
| 114a | 2-EtO-PhCH$_2$NH |
| 115a | 4-EtO-PhCH$_2$NH |
| 116a | 4-MeO-Naph-1-yl-CH$_2$NH |
| 185a | 5-Me-IM-4-ylCH$_2$NH |
| 186a | IM-2-ylCH$_2$NH |
| 187a | 6-Me-Py-2-ylCH$_2$NH |

TABLE 6

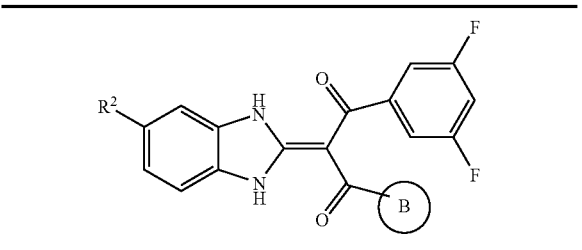

| Compound No. | R² | B |
|---|---|---|
| 117a | H | 1H-IM-4-yl |
| 118a | H | Fu-2-yl |
| 119a | H | 3-PhNHCOPh |
| 120a | H | 3-H₂N-5-F₃C-Ph |
| 121a | O₂N | 3,5-diF-Ph |
| 122a | O₂N | 2-Me-Ph |
| 123a | O₂N | 3-F₃C-O-Ph |
| 124a | O₂N | 3-Cl-Ph |
| 125a | O₂N | 3,4-diMe-Ph |
| 126a | O₂N | 4-MeO-Ph |
| 127a | O₂N | 2-Cl-Ph |
| 128a | O₂N | 2,5-diF-Ph |
| 129a | O₂N | 2-F₃C-Ph |
| 130a | O₂N | 3,5-diMe-Ph |
| 131a | O₂N | 2-F-Ph |
| 132a | O₂N | 3,5-diMeO-Ph |
| 133a | O₂N | 5-Br-Py-3-yl |
| 134a | O₂N | 3-Br-Ph |
| 135a | O₂N | 3-Me-Ph |
| 136a | H₂N | 3-F-Ph |
| 137a | H₂N | 4-Me-Ph |
| 138a | H₂N | 4-F₃C-O-Ph |
| 139a | H₂N | 2-F₃C-O-Ph |
| 140a | H₂N | 4-Cl-Ph |
| 141a | H₂N | 3-Cl-Ph |
| 142a | H₂N | 3,4-diMe-Ph |
| 143a | H₂N | 4-MeO-Ph |
| 144a | H₂N | 2-Cl-Ph |
| 145a | H₂N | 2-F₃C-Ph |
| 146a | H₂N | 2-F-Ph |
| 147a | H₂N | 3,5-diMeO-Ph |
| 148a | H₂N | 4-F₃C-Ph |
| 149a | H₂N | 3-Br-Ph |
| 150a | H | 5-Me-Py-3-yl |
| 151a | H | 5-MeO-Py-3-yl |
| 152a | H | 2-H₂N-Thiaz-4-yl |
| 153a | H | 1-(4-F-PhCH₂)IM-4-yl |
| 154a | H | 2-Me-Thiaz-4-yl |
| 155a | H | 5-Me-Py-3-yl |
| 156a | Py-3-ylCH₂NH | 3-H₂NPh |
| 157a | H | 6-F₃C-Py-3-yl |
| 158a | Py-3-ylCH₂NH | Py-3-yl |
| 159a | H | 1-Me-Pyrrol-3-yl |
| 160a | H | 1,2,3-Thiadiazol-5-yl |
| 161a | 4-NO₂-PhCONH | 3-H₂N-Ph |
| 162a | H | Pyrazine-2-yl |
| 163a | H | 1-Me-benzoIM-5-yl |
| 164a | Py-3-ylCONH | 3-Me-Ph |
| 165a | 3-Cl-PhSO₂NH | 3-Me-Ph |
| 166a | 4-AcNH-PhCH₂NH | 3,5-diF-Ph |
| 167a | 4-AcNH-PhCH₂NH | 2-Me-Ph |
| 168a | 4-AcNH-PhCH₂NH | 4-F₃C-O-Ph |
| 169a | 4-AcNH-PhCH₂NH | 3-F₃C-O-Ph |
| 170a | 4-AcNH-PhCH₂NH | 3-F₃C-Ph |
| 171a | 4-AcNH-PhCH₂NH | 4-Cl-Ph |
| 172a | 4-AcNH-PhCH₂NH | 3,4-diMe-Ph |
| 173a | 4-AcNH-PhCH₂NH | 4-MeO-Ph |
| 174a | 4-AcNH-PhCH₂NH | 3,5-diMeO-Ph |
| 175a | 4-AcNH-PhCH₂NH | 4-F₃C-Ph |
| 176a | 3-Cl-PhCH₂NH | 4-F-Ph |
| 177a | 4-HO-PhCH₂NH | 4-F-Ph |
| 178a | 3-CN-PhCH₂NH | 2-MeO-Ph |
| 179a | 3-Cl-PhCH₂NH | 2-MeO-Ph |
| 180a | 4-HOOC-PhCH₂NH | 2-MeO-Ph |

TABLE 6-continued

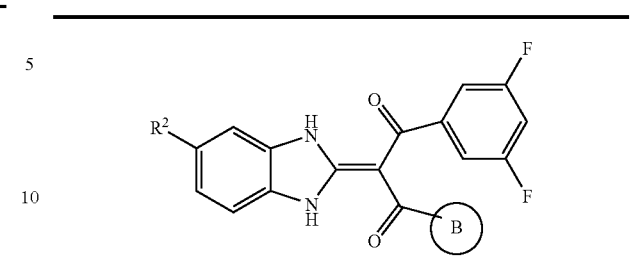

| Compound No. | R² | B |
|---|---|---|
| 181a | 4-HO-PhCH₂NH | 3-Me-Ph |
| 182a | 2-Cl-PhCH₂NH | 3-Me-Ph |
| 183a | 3-Br-PhCH₂NH | Ph |
| 184a | 4-Cl-PhCH₂NH | Ph |

TABLE 7

| Compound No. | R² | B |
|---|---|---|
| 188a | H | 3-{Me[MeO(CH₂)₂]N}Ph |
| 189a | H | 2-H₂N-CH₂-Ph |
| 190a | H | 2-(1-HOOC-EtNH)Ph |
| 191a | H | 3-HOOC-Ph |
| 192a | Pipe-1-yl | Ph |
| 193a | H | 4-H₂NCO-IM-1-yl |
| 194a | PhNHCO-diMe-C | Ph |
| 195a | 3-CN-PhNHCOCH₂ | Ph |
| 196a | Py-4-ylCH₂OCOCH₂ | Ph |
| 197a | H | 3-H₂N-5-F-Ph |
| 198a | 3-F-PhCH₂NHCH₂ | Ph |
| 199a | F | 4-cPr-NH-Ph |
| 200a | Py-4-ylCONH | Ph |
| 201a | 3-MeOCOPhCH₂CO | Ph |
| 202a | 6-F₃C-Py-3-ylCH₂NH | 3,5-diF-Ph |
| 203a | 4-tBuOCONH-Py-3-ylCH₂NH | 3,5-diF-Ph |
| 204a | 2-Cl-Py-3-ylCH₂NH | 3,5-diF-Ph |
| 205a | 4-H₂N-Py-3-ylCH₂NH | 3,5-diF-Ph |
| 206a | 6-Me-Py-2-ylCH₂NH | 3,5-diF-Ph |
| 207a | 3-Cl-4-F₃C-Py-2-ylCH₂NH | 3,5-diF-Ph |
| 208a | 4,6-diMe-Py-2-ylCH₂NH | 3,5-diF-Ph |
| 209a | 5-CN-6-MeS-Py-2-ylCH₂NH | 3,5-diF-Ph |
| 210a | 3,6-diCl-4-OH-Py-2-ylCH₂NH | 3,5-diF-Ph |
| 211a | Py-2-ylCH₂NH | 3,5-diF-Ph |
| 212a | Py-4-ylCH₂NH | 3,5-diF-Ph |
| 213a | 2,6-diCl-Py-4-ylCH₂NH | 3,5-diF-Ph |
| 214a | 3,5-diOH-2-Me-Py-4-ylCH₂NH | 3,5-diF-Ph |

TABLE 8

| Compound No. | Str |
|---|---|
| 215a | (structure) |
| 216a | (structure) |
| 217a | (structure) |
| 218a | (structure) |
| 219a | (structure) |
| 222a | (structure) |

The active ingredient of the invention and the compound of the invention or a pharmaceutically acceptable salt thereof can be employed solely as a pharmaceutical drug but usually, one or two or more of the active ingredients can be formulated by a generally used method using drug carriers, fillers and the like generally used in the art. Its administration may be either oral administration by tablets, pills, capsules, granules, powders, solutions and the like, or parenteral administration by intra-articular, intravenous, intramuscular, and the like injections, suppositories, eye drops, ophthalmic ointments, percutaneous solutions, ointments, percutaneous adhesive preparations, transmucosal solutions, transmucosal adhesive preparations, inhalations and the like.

The solid composition for use in the oral administration according to the present invention is used in the form of tablets, powders, granules and the like. In such a solid composition, one or more active ingredients are mixed with at least one inert diluent such as lactose, mannitol, glucose, hydroxypropylcellulose, microcrystalline cellulose, starch, polyvinyl pyrrolidone, magnesium aluminate metasilicate and/or the like. In accordance with the usual procedures, the composition may contain inert additives other than the diluent, for example, a lubricant such as magnesium stearate, a disintegrating agent such as calcium cellulose glycolate, a stabilizer such as lactose, and a solubilization assisting agent such as glutamic acid or aspartic acid. If necessary, tablets or pills may be coated with a sugar or a film of a gastric or enteric coating substance, such as sucrose, gelatin, hydroxypropyl cellulose or hydroxypropylmethyl cellulose phthalate.

The liquid composition for oral administration includes pharmaceutically acceptable emulsions, solutions, suspensions, syrups, elixirs and the like and contains a generally used inert diluent, e.g., purified water or ethanol. In addition to the inert diluent, this composition may further contain an auxiliary agent such as a solubilizing agent, a moistening agent, a suspending agent or the like, as well as a sweetener, a flavor, an aromatic and a preservative.

The injections for parenteral administration include sterile aqueous or non-aqueous solutions, suspensions and emulsions. Examples of the aqueous solutions or suspensions include distilled water for injection and saline. Examples of the non-aqueous solutions or suspensions include propylene glycol, polyethylene glycol, vegetable oils such as olive oil, alcohols such as ethanol, polysorbate 80 (trade name) and the like. Such a composition may further contain auxiliary agents such as a tonicity agent, a preservative, a moistening agent, an emulsifier, a dispersing agent, a stabilizer (e.g., lactose) and a solubilization assisting agent (e.g., glutamic acid or aspartic acid). These compositions are sterilized, e.g., by filtration through a bacteria-retaining filter, blending of a germicide or irradiation. Alternatively, they may be used by firstly making into sterile solid compositions and then dissolving or suspending them in sterile water or a sterile solvent for injection use prior to their use.

The transmucosal preparations such as transnasal preparations are used in the form of solid, liquid or semi-solid, and can be produced in accordance with hitherto known methods. For example, known pH adjusting agent, preservative, thickener and filler are optionally added and the preparations are formed into solid, liquid or semi-solid. The transnasal preparations are administered by means of a usual sprayer, nasal container, tube, intranasal insert or the like.

In the case of oral administration, suitable daily dose is usually about 0.001 to 100 mg/kg, preferably 0.1 to 30 mg/kg, more preferably 0.1 to 10 mg/kg-body weight, and the dose is divided into 1 or 2 to 4 doses per day. In the case of intravenous administration, suitable daily dose is about 0.0001 to 10 mg/kg-body weight, and the dose is divided into 1 to several doses per day. And, in the case of transmucosal preparations, about 0.001 to 100 mg/kg-body weight is divided into 1 to several doses per day. The dose may be appropriately determined for each case, depending on conditions, age, sex and the like.

EXAMPLES

The following will explain the invention further in detail based on Examples. The compounds of the invention are not limited to the compounds described in the following Examples. In this connection, production methods of starting compounds are shown in Reference Examples.

Reference Example 1

To a boiling suspension of sodium hydride (60% in oil) (360 mg) in anhydrous THF (10 ml) was added dropwise a solution of acetophenone (720 mg) and ethyl 2-methylthiazol-4-carboxylate (1.20 g) in anhydrous THF (10 ml), followed by 10 minutes of heating under refluxing. After the reaction solution was cooled, a mixed solution of acetic acid (1 ml) and water (30 ml) was added thereto, and the resulting mixture was extracted with ethyl acetate. The extracted solution was washed with water and then dried over anhydrous magnesium sulfate. The solvent was evaporated under reduced pressure and the residue was purified by silica gel column chromatography (eluent: hexane:ethyl acetate=4:1 (v/v)) to obtain 1-(2-methylthiazol-4-yl)-3-phenylpropan-1,3-dione (1.3 g, 88%) as yellow crystals. Hereinafter, the compounds of Reference Examples 2 to 10 were obtained similarly.

Reference Example 11

To a solution of the compound (674 mg) obtained in Reference Example 1 in DMF (8 ml) was added potassium carbonate (1.14 g), followed by 1 hour of stirring at room temperature. After carbon disulfide (283 mg) was added to the reaction solution and the resulting mixture was stirred at room temperature for 2 hours, methyl iodide (0.369 ml) was further added, followed by 1.5 hours of stirring at room temperature. Water was added to the reaction solution and the resulting mixture was extracted with ethyl acetate. The extract solution was washed with water and then dried over anhydrous magnesium sulfate. The solvent was evaporated under reduced pressure and the residue was purified by silica gel column chromatography (eluent (v/v): hexane:ethyl acetate=4:1) to obtain 2-(bismethylsulfanylmethylene)-1-(2-methylthiazol-4-yl)-3-phenylpropan-1,3-dione (555 mg, 64%) as a yellow oily substance. Hereinafter, the compounds of Reference Examples 12 to 23 were obtained similarly.

Reference Example 24

A catalytic amount of ammonium chloride was added into 100 ml acetic acid solution containing terephthaldicarboxaldehyde (1.34 g) and 3-methylrhodanine (1.53 g), followed by about 12 hours of heating at 110° C. After cooling upon standing, the formed yellow crystals were collected by filtration, washed with an appropriate amount of ethanol-water (10:1), and dried to obtain 4-(3-methyl-4-oxo-2-thioxothiazolidin-5-ylidenmethyl)benzaldehyde (1.91 g).

Reference Example 25

Into a saturated ammonia-methanol solution (60 ml) was added 4-chloro-3-nitro-N-(pyridin-3-ylmethyl)benzenesulfonamide (2.77 g), followed by about 2 days of heating at 100° C. in a sealed tube. After the reaction, the solvent was evaporated under reduced pressure and the formed yellow crystals were collected by filtration and dried to obtain 4-amino-3-nitro-N-(pyridin-3-ylmethyl)benzenesulfonamide (2.51 g). Hereinafter, the compound of Reference Examples 26 was obtained similarly.

Reference Example 27

A catalytic amount of Raney nickel was added to an ethyl acetate-ethanol (1:1) solution (200 ml) containing the compound (2.49 g) obtained in Reference Example 25, followed by a reaction in the presence of hydrogen gas at ordinary temperature under ordinary pressure. After the reaction, a filtrate obtainable by removing the catalyst by filtration was evaporated under reduced pressure to obtain 3,4-diamino-N-(pyridin-3-ylmethyl)benzenesulfonamide (2.22 g).

Reference Example 28

Into a DMF solution (150 ml) containing 4-amino-3-nitrophenol (4.72 g) were added successively potassium carbonate (12.8 g), tetrabutylammonium iodide (0.56 g) and 3-chloromethylpyridine hydrochloride (5.42 g), followed by about 1.5 hours of heating at 60° C. The reaction solution was concentrated under reduced pressure, ice-water (250 ml) and 1M hydrochloric acid aqueous solution (30 ml) were poured thereto, and the formed crystals were collected by filtration and dried to obtain 2-nitro-4-(pyridin-3-ylmethoxy)aniline (7.39 g). Hereinafter, the compounds of Reference Examples 35 and 60 were obtained similarly.

Reference Example 29

Into an ethyl acetate-ethanol (1:1) solution (300 ml) containing the compound (3.68 g) obtained in Reference Example 28 was added 10% palladium on carbon, followed by a reaction in the presence of hydrogen gas at ordinary temperature under ordinary pressure. After the reaction, a filtrate obtainable by removing the catalyst by filtration was evaporated under reduced pressure to obtain 4-(pyridin-3-ylmethoxy)benzene-1,2-diamine (3.23 g). Hereinafter, the compound of Reference Example 30 was obtained similarly.

Reference Example 31

Triphenylpyridin-3-ylmethylphosphonium chloride (1.95 g) was added into an ice-cooled DMF suspension (40 ml) containing sodium hydride (60% in oil) (0.26 g), followed by 30 minutes of stirring at room temperature. The reaction solution was cooled to 0° C. and 4-chloro-3-nitrobenzaldehyde (1.04 g) was added portionwise thereto, followed by 2 hours of stirring at room temperature. To the residue formed by evaporating the reaction solution under reduced pressure was poured an appropriate amount of purified water, followed by extraction with ethyl acetate. Thereafter, the organic layer was dried over anhydrous magnesium sulfate. The crude product obtained by solvent evaporation was purified by silica gel column chromatography to obtain 3-[2-(4-chloro-3-nitrophenyl)vinyl]pyridine (0.86 g) from the fractions eluted with ethyl acetate-hexane (2:1 (v/v)).

Reference Example 32

To a DMF solution (10 mL) of (2-methyl-1H-benzimidazol-5-yl)methanol (811 mg) were added tert-butyldimethylsilyl chloride (904 mg) and imidazole (680 mg), followed by 2 hours of stirring at room temperature. The reaction solution was concentrated, water was added thereto, the mixture was extracted with chloroform, and the extract was dried over anhydrous magnesium sulfate. The organic layer was concentrated under reduced pressure and the obtained residue was purified by silica gel column chromatography (eluent: chloroform:methanol=10:1 (v/v)) to obtain 5-(tert-butyldimethylsilyloxymethyl)-2-methyl-1H-benzimidazole (1305 mg, 94%).

Reference Example 33

Into an ethanol solution (100 ml) containing the compound (2.2 g) obtained in Reference Example 27 was added triethyl orthoacetate (3.21 g), followed by about 12 hours of heating under refluxing. Concentrated hydrochloric acid (1 ml) was added dropwise and the whole was heated under refluxing for another 2 hours. Then, the reaction solution was evaporated under reduced pressure. The residue was washed with cooled water (100 ml) containing saturated sodium hydrogen carbonate aqueous solution (10 ml), collected by filtration and dried to obtain 2-methyl-1H-benzimidazol-5-sulfonic acid (pyridin-3-ylmethyl)amide (1.94 g). Hereinafter, the compounds of Reference Examples 34 and 36 were obtained similarly.

Reference Example 37

(1) Benzoyl chloride (32.5 ml) was added dropwise to a mixture of 2-methyl-5-nitrobenzimidazole (12.5 g) and TEA (38.8 ml) in Diglyme (63 ml) at room temperature. The reaction mixture was stirred at 100° C. for 1 hour. Water was added to the reaction mixture cooled to room temperature and the whole was stirred for 45 minutes. The reaction mixture was extracted with chloroform, the organic layer was washed with water and dried over anhydrous sodium sulfate, and then the solvent was evaporated under reduced pressure. The obtained crude crystals were recrystallized from chloroform-n-hexane to obtain 2-(1-benzoyl-1H-5-nitrobenzimidazol-2-yl)-1-phenylvinyl benzoate (29.7 g, 86%).

(2) The compound obtained in (1) (29.7 g) and morpholine (15.8 g) were dissolved in methanol (90 ml), followed by 30 minutes of heating under refluxing. After the reaction mixture was cooled to room temperature, water was added thereto and the whole was stirred for 2 hours. The formed precipitate was collected by filtration, washed with cold water, and then dried to obtain 2-(1,3-dihydro-2H-5-nitrobenzimidazol-2-ylidene)-1-phenylethan-1-one (16.7 g, 84%). Hereinafter, the compounds of Reference Examples 38 to 54 and Reference Examples 61 to 64 were obtained similarly.

Reference Example 55

Into a 1,4-dioxane solution (250 ml) containing 2-amino-4-chlorothiazol-5-carbaldehyde (10.83 g) was added 4-(dimethylamino)pyridine (1 g). Then, a 1,4-dioxane solution (100 ml) containing di-tert-butyl dicarbonate (29 g) was gradually added dropwise under heating at 60° C., and then the whole was continued to stir for about 30 minutes. After the reaction solution was cooled upon standing, the solvent was evaporated under reduced pressure and an appropriate amount of 5% potassium hydrogen sulfate aqueous solution was poured to the thus obtained residue, followed by extraction with ethyl acetate. After the organic layer was washed with water and dried over anhydrous magnesium sulfate, the crude product formed by solvent evaporation was purified by silica gel column chromatography to obtain tert-butyl (4-chloro-5-formylthiazol-2-yl)-carbamate (10.73 g) as pale brown crystals from the fractions eluted with ethyl acetate-toluene (2:3 (v/v)).

Reference Example 56

Under an argon stream, a dioxane solution (10 ml) of tris-t-butylphosphine (240 mg) was added to a mixture of p-methoxyphenyl boric acid (4.364 g), tris(dibenzylideneacetone)dipalladium (452 mg), cesium carbonate (10.561 g), 5-chloro-2-nitroaniline (4505 mg) and dioxane (50 ml), followed by 2 hours and 10 minutes of heating at 85° C. After cooling to room temperature on standing, diethyl ether (500 ml) and chloroform (500 ml) were added thereto. After insoluble matter was removed by filtration, the filtrate was concentrated to obtain an aimed compound, 5-(4'-methoxyphenyl)-2-nitroaniline (6.5 g).

Reference Example 57

A catalytic amount of concentrated sulfuric acid was added dropwise to an acetic anhydride (55 ml) suspension of 5-(4'-methoxyphenyl)-2-nitroaniline (2.02 g), followed by 3 hours and 20 minutes stirring at 40° C. After cooling to room temperature, diethyl ether (200 ml) was added thereto and the precipitated powder was collected by filtration to obtain N-(4'-methoxy-4-nitrobiphenyl-3-yl)acetamide (596 mg).

Reference Example 58

A mixture of N-(4'-methoxy-4-nitrobiphenyl-3-yl)acetamide (500 mg), acetic acid (6 ml) and iron powder (308 mg) was stirred at 100° C. for 50 minutes, and then cooled to room temperature, and insoluble matter was removed by filtration using celite. A saturated sodium carbonate aqueous solution was added to the filtrate to render the liquid about pH 7, followed by extraction with chloroform. The organic layer was dried over anhydrous magnesium sulfate and then concentrated under reduced pressure to obtain 5-(4'-methoxyphenyl)-2-methylbenzimidazole (320 mg).

Reference Example 59

To a dimethylformamide (20 ml) solution of 2-methylbenzimidazol-5-carboxylic acid (1.00 g) were added hydroxybenzotriazole (844 mg), 1-ethyl-3-(3'-dimethylaminopropyl)carbodiimide hydrochloride (1.21 g) and 4-methoxyphenylmethylamine (1.33 g) at room temperature, and the reaction solution was stirred at room temperature for 18 hours. The reaction solution was concentrated under reduced pressure and the obtained residue was diluted with chloroform (20 ml). The organic layer was washed with saturated sodium hydrogen carbonate aqueous solution, water and saturated sodium chloride aqueous solution, and dried over anhydrous sodium sulfate. The residue obtained by solvent evaporation under reduced pressure was subjected to silica gel column chromatography and eluted with chloroform-methanol (30:1 (v/v)) to obtain (4-methoxyphenylmethyl)amide of 2-methyl-1H-benzimidazol-5-carboxylic acid (1.27 g, 99%).

Example 1

5-Chloro-2-methylbenzimidazole (833 mg) was dissolved in Diglyme (4 ml), and TEA (2.43 ml) was added thereto. Benzoyl chloride (2.0 ml) was further added thereto, followed by 15 minutes of stirring at about 100° C. Water (0.1 ml) was added dropwise to the reaction solution and the whole was heated under stirring at 175° C. for 10 minutes. After the reaction solution was cooled with air, water (15 ml) was added and the mixture was stirred, then the supernatant was decanted. Methanol (5 ml) was added to the residue and the precipitated crystals were collected by filtration, washed with cold methanol, and dried to obtain 2-(5-chloro-1,3-dihydro-2H-benzimidazol-2-yliden)-1,3-diphenylpropan-1,3-dione (706 mg, 38%) as pale yellow powdery crystals. Hereinafter, the compounds of Examples 2 to 25, 119 and 126 were obtained similarly.

Example 26

In a similar manner to Reference Example 37, 2-(1-benzoyl-1H-benzimidazol-2-yl)-1-phenylvinyl benzoate (26.8 g, 86%) was obtained in Step (1) and 2-(1,3-dihydro-2H-benzimidazol-2-ylidene)-1-phenylethan-1-one (11.9 g, 84%) in Step (2).

(3) To a mixture of 3,5-difluorobenzoyl chloride (1.67 g) and pyridine (8.5 ml) was added portionwise the compound (1.01 g) obtained in the above (2), followed by 3 hours of stirring at room temperature. Water was added to the reaction mixture, followed by extraction with chloroform. The obtained organic layer was washed with water, saturated ammonium chloride aqueous solution and saturated brine, and dried over anhydrous sodium sulfate, and then the solvent was evaporated under reduced pressure. The obtained residue was subjected to silica gel column chromatography to obtain 2-[1-(3,5-difluorobenzoyl)-1H-benzimidazol-2-yl]-1-phenylvinyl 3,5-difluorobenzoate (1.45 g, 65%) as yellowish white powdery crystals.

(4) The compound (931 mg) obtained in (3) and 3,5-difluorobenzoic acid (570 mg) were dissolved in Diglyme (2.5 ml), followed by 20 minutes of stirring at 175° C. Water was added to the reaction mixture cooled to room temperature, the mixture was extracted with chloroform, the organic layer was washed with water and dried over anhydrous sodium sulfate, and then the solvent was evaporated under reduced pressure. The obtained residue was subjected to silica gel column chromatography to obtain yellow powdery crystals from the fractions eluted with chloroform-n-hexane. The crystals were recrystallized from methanol to obtain 1-(3,5-difluorophenyl)-2-(1,3-dihydro-2H-benzimidazol-2-ylidene)-3-phenylpropan-1,3-dione (603 mg, 89%). Hereinafter, the compounds of Examples 27 to 39, 117, 118, 120 to 125, 127 to 166, 425, 431 and 446 were obtained similarly.

Example 40

A mixture of the compound (317 mg) obtained in Example 35, platinum (IV) oxide (30 mg) and ethyl acetate (30 ml) was stirred at room temperature for 23 hours under hydrogen atmosphere. After a black powder was removed by filtration, the filtrate was concentrated and the obtained residue was treated with 4M hydrogen chloride-ethyl acetate solution to obtain 1-(3-aminophenyl)-3-(3,5-difluorophenyl)-2-(1,3-dihydro-2H-benzimidazol-2-ylidene)propane-1,3-dione hydrochloride (245 mg, 76%) as a green powder. Hereinafter, the compounds of Examples 41 to 43, 167 to 203, 411, 412 and 432 were obtained similarly.

Example 44

The compound (200 mg) obtained in Example 43 was dissolved in pyridine (2 ml), and propionyl chloride (58 mg) was added dropwise thereto under ice cooling. The reaction temperature was raised to room temperature and the whole was stirred for 1 hour. Water was added to the reaction mixture, followed by extraction with chloroform. The obtained organic layer was washed with water and saturated brine and dried over anhydrous sodium sulfate, and then the solvent was evaporated under reduced pressure. The obtained residue was subjected to silica gel column chromatography to obtain 3'-[2-(1,3-dihydro-2H-benzimidazol-2-ylidene)-3-oxo-3-phenylpropanoyl]propananilide (204 mg, 88%) as a yellow foamed powder from the fractions eluted with chloroform-methanol. Hereinafter, the compounds of Examples 45 to 78, 204 to 237, 416 to 420, 430, 433, 440 to 442 and 449 were obtained similarly.

Example 79

The compound (162 mg) obtained in Example 39 was dissolved in DMF (10 ml), and 4-(2-aminoethyl)pyridine (348 mg), potassium carbonate (591 mg) and potassium iodide (473 mg) were added thereto, followed by 7 hours stirring at room temperature. Ethyl acetate and water were added to the reaction mixture and the organic layer was separated. The obtained organic layer was washed with water and saturated brine and dried over anhydrous sodium sulfate, and then the solution was evaporated under reduced pressure. The obtained residue was subjected to silica gel column chromatography and the fractions eluted with chloroform were dissolved into ethyl acetate, then ethanolic hydrochloric acid was added thereto. The formed crystals were filtered to obtain 2-(1,3-dihydro-2H-benzimidazol-2-ylidene)-1-phenyl-3-(3-([(2-pyridin-4-ylethyl)amino]methyl)phenyl)propane-1,3-dione hydrochloride (417 mg, 51%) as a pale pink powder. Hereinafter, the compounds of Examples 80, 81 and 450 were obtained similarly.

Example 82

The compound (343 mg) obtained in Example 30 was dissolved in ethanol (8 ml), and morpholine (0.4 ml) was added thereto, followed by 2 hours of heating under refluxing. The reaction solution was cooled and then evaporated under reduced pressure. Chloroform and water were added to the obtained residue and the organic layer was separated. The obtained organic layer was washed with water and saturated brine and dried over anhydrous sodium sulfate, and then the solution was evaporated under reduced pressure. The obtained residue was subjected to silica gel column chromatography to obtain 2-(1,3-dihydro-2H-benzimidazol-2-ylidene)-1-(3-hydroxyphenyl)-3-phenylpropane-1,3-dione (125 mg, 41%) as a yellow powder from the fractions eluted with chloroform.

Example 83

The compound (450 mg) obtained in Example 40 was dissolved in benzene (30 ml), and 4-formylimidazole (121 mg) and a catalytic amount of p-toluenesulfonic acid were added thereto, followed by stirring at room temperature for 3 hours, at 50° C. for 2.5 hours and under heating with refluxing for 3.5 hours. The residue after solvent evaporation was dissolved in methanol (25 ml), and sodium borohydride (44 mg) was added under ice cooling, followed by 1 hour and 40 minutes of stirring. Water, chloroform and isopropanol were added to the reaction solution and the organic layer was separated. The residue obtained by concentrating the obtained organic layer was subjected to silica gel column chromatography to obtain 1-(3,5-difluorophenyl)-2-(1,3-dihydro-2H-benzimidazol-2-ylidene)-3-(3-[(1H-imidazol-4-ylmethyl)amino]phenylpropane-1,3-dione from the fractions eluted with chloroform-methanol. This compound was converted into a hydrochloride salt using 4M hydrogen chloride-ethyl acetate solution to obtain 1-(3,5-difluorophenyl)-2-(1,3-dihydro-2H-benzimidazol-2-ylidene)-3-{3-[(1H-imidazol-4-ylmethyl)amino]phenyl}propane-1,3-dione hydrochloride (159 mg, 27%) as a pale blue powder. Hereinafter, the compounds of Examples 395 to 396 were obtained similarly.

Example 84

To a methylene chloride (3 mL) solution of the compound (180 mg) obtained in Example 43 was added pyridin-3-aldehyde (60 mg) and acetic acid (153 mg), and sodium triacetoxyborohydride (215 mg) was further added thereto under ice cooling, followed by 15 hours of stirring at room temperature. A saturated sodium hydrogen carbonate aqueous solution was added to the reaction mixture and the mixture was extracted with methylene chloride. After washing with water and saturated brine, the extract was dried over anhydrous magnesium sulfate. The organic layer was concentrated under reduced pressure and the obtained residue was purified by silica gel column chromatography (eluent: chloroform:methanol=30:1 (v/v)). The purified product was dissolved into chloroform (3 mL) and subjected to salt formation with 4M-HCl-ethyl acetate solution to obtain 2-(1,3-dihydro-2H-benzimidazol-2-ylidene)-1-phenyl-3-{3-(pyridin-3-ylmethylamino)phenyl}propane-1,3-dione hydrochloride (186 mg, 76%). Hereinafter, the compounds of Examples 85 to 100, 238 to 393, 410, 413 to 415, 421 to 424, 426, 428, 429, 435 to 437, 439 and 443 to 445 were obtained similarly.

Example 101

The compound (512 mg) obtained in Reference Example 11 was dissolved in ethanol (6 ml), and 1,2-phenylenediamine (237 mg) was added thereto, followed by 13 hours of heating under refluxing. The reaction solution was cooled and the formed crystals were collected by filtration and washed with methanol to obtain 2-(1,3-dihydro-2H-benzimidazol-2-ylidene)-1-(2-methylthiazol-4-yl)-3-phenylpropane-1,3-dione (171 mg, 32%) as a yellow powder. Hereinafter, the compounds of Examples 102 to 111, 397 and 398 were obtained similarly.

Example 112

(1) Using the compound obtained in Reference Example 19, 1-(5-benzyloxypyridin-3-yl)-3-(3,5-difluorophenyl)-2-(1,3-dihydro-2H-benzimidazol-2-ylidene)propane-1,3-dione was obtained in a similar manner to Example 101.

(2) The compound (121 mg) obtained in (1) was dissolved in ethanol (6 ml), and 10% palladium on carbon (160 mg) was added thereto, followed by 21 hours of vigorous stirring under hydrogen atmosphere. The catalyst was removed by filtration, the filtrate was concentrated under reduced pressure, and the residue was purified by silica gel column chromatography (eluent: chloroform:methanol=10:1 (v/v)). The eluate was recrystallized from chloroform-methanol-hexane to obtain 1-(3,5-difluorophenyl)-2-(1,3-dihydro-2H-benzimidazol-2-ylidene)-3-(5-hydroxypyridin-3-yl)propane-1,3-dione (61 mg, 62%) as yellow crystals.

Example 113

The compound (150 mg) obtained in Example 20 was dissolved in dichloromethane (4 ml) under argon atmosphere, and 1.0M boron tribromide-methylene chloride solution (1.25 ml) was added dropwise thereto under ice cooling. After 1 hour of stirring at 0° C., the reaction temperature was raised to room temperature and the whole was further stirred for another 4 hours. Methanol (0.5 ml) was added to the reaction mixture under ice cooling, followed by 40 minutes of stirring. Then, chloroform and water were added thereto, and the organic layer was separated. The resulting organic layer was washed with water and saturated brine and dried over anhydrous sodium sulfate, and then the solution was evaporated under reduced pressure. The obtained residue was subjected to silica gel column chromatography to obtain 2-(5-hydroxy-1,3-dihydro-2H-benzimidazol-2-ylidene)-1,3-bis(3-methylphenyl)propane-1,3-dione (39 mg, 27%) as an orange powder from the fractions eluted with chloroform.

Example 114

Benzoyl chloride (1.68 g) was added to a mixture of 1,2-dimethylbenzimidazole (0.5 g) and TEA (1.21 g) in Diglyme (5 ml) at room temperature. The reaction mixture was stirred at 120° C. for 1 hour and successively at 150° C. for 6 hours. Water was added to the reaction mixture, followed by extraction with ethyl acetate. The organic layer was washed with water and dried over anhydrous magnesium sulfate, and then the solvent was evaporated under reduced pressure. The obtained residue was subjected to silica gel column chromatography to obtain crude crystals from the fractions eluted with chloroform. The crystals were recrystallized from ethyl acetate to obtain 2-(2-methyl-1H-benzimidazol-2-yl)-1,3-diphenylpropane-1,3-dione (0.81 g). Hereinafter, the compound of Example 115 was obtained similarly.

Example 116

(1) The compound (1.01 g) obtained in Example 3 and N-bromosuccinimide (609 mg) were dissolved in tetrachloromethane (14 ml), and azobisisobutyronitrile (47 mg) was added thereto, followed by 1 hour of heating under refluxing. After the reaction solution was cooled, the precipitated crystals were collected and dried to obtain 2-(1-bromo-5-methyl-1,3-dihydro-2H-benzimidazol-2-ylidene)-1,3-diphenylpropane-1,3-dione (1.22 g, 99%) as cream-colored powdery crystals.

(2) The compound obtained in (1) (400 mg), potassium carbonate (153 mg) and diethylamine (0.115 ml) were dissolved in DMF (4 ml), followed by 4.5 hours of stirring at room temperature. The reaction mixture was poured into water and extracted with chloroform. The resulting organic layer was washed with water and saturated brine and dried over anhydrous sodium sulfate, and then the solution was evaporated under reduced pressure. The obtained residue was subjected to silica gel column chromatography to obtain a yellow oily substance from the fractions eluted with chloroform. To a solution of this substance dissolved in chloroform (1 ml) was added dropwise 4M-hydrogen chloride-ethyl acetate solution under ice cooling, followed by 30 minutes of stirring at room temperature. The precipitated crystals were collected by filtration, washed with chloroform, and dried to obtain 2-(1diethylamino-5-methyl-1,3-dihydro-2H-benzimidazol-2-ylidene)-1,3-diphenylpropane-1,3-dione hydrochloride (203 mg, 48%) as a pale yellow powder.

Example 394

To a THF solution (5 ml) of 3-{2-[5-(4-acetylaminobenzylamino)-1,3-dihydro-2H-benzimidazol-2-ylidene]-3-(3,5- difluorophenyl)-3-oxopropionyl}phenyl acetate (123 mg) was added 1M sodium hydroxide aqueous solution (0.5 ml), followed by 24 hours of stirring. A saturated ammonium chloride aqueous solution was added thereto, followed by extraction with ethyl acetate and drying over anhydrous magnesium sulfate. The organic layer was concentrated under reduced pressure and the obtained residue was purified by silica gel column chromatography (eluent: chloroform:methanol=20:1 (v/v)) to obtain N-[4-({2-[1-(3,5-difluorobenzoyl)-2-(3-hydroxyphenyl)-2-oxoethylidene]-2,3-dihydro-1H-benzimidazol-5-ylamino}methyl)phenyl]acetamide (98 mg, 86%). Hereinafter, the compound of Example 438 was obtained similarly.

Example 399

An ethanol solution (10 ml) containing the compound (0.23 g) obtained in Example 127 was cooled to −15° C. and 90% sodium borohydride (30 mg) was added thereto, followed by 1 hour of stirring at the same temperature. Appropriate amounts of purified water and saturated brine were poured into the reaction solution, followed by extraction with ethyl acetate. The organic layer was dried and concentrated and the obtained residue was purified by silica gel column chromatography to obtain 1-(3,5-difluorophenyl)-2-[5-(1-hydroxyethyl)-1,3-dihydro-2H-benzimidazol-2-ylidene]-3-phenylpropane-1,3-dione (90 mg) from the fractions eluted with chloroform-methanol (50:1 (v/v)). Hereinafter, the compound of Example 400 was obtained similarly.

Example 401

Into an acetic acid solution (40 ml) containing the compound (0.77 g) obtained in Example 132 was added 10% palladium on carbon (80 mg), followed by stirring under hydrogen gas atmosphere at ordinary temperature under ordinary pressure. After removal of the catalyst by filtration, the solvent was evaporated under reduced pressure, followed by extraction with ethyl acetate. The ethyl acetate layer was washed with appropriate amounts of sodium hydrogen carbonate aqueous solution and saturated brine successively and dried over anhydrous magnesium sulfate, and the solvent was evaporated under reduced pressure to obtain 1-(3,5-difluorophenyl)-2-(5-hydroxy-1,3-dihydro-2H-benzimidazol-2-ylidene)-3-phenylpropane-1,3-dione (0.58 g).

Example 402

Into an acetonitrile solution (4 ml) containing the compound (100 mg) obtained in Example 401 and (3-chloromethyl)pyridine hydrochloride (50 mg) were added potassium carbonate (83 mg) and a catalytic amount of sodium iodide successively, followed by 3.5 hours of heating at 80° C. After solvent evaporation, an appropriate amount of purified water was poured, followed by extraction with ethyl acetate. After drying over anhydrous magnesium sulfate and concentration, the resulting residue was purified by silica gel column chromatography to obtain yellow foam (43 mg) from the fractions eluted with chloroform-methanol (200:1 (v/v)). This substance was dissolved into acetone (2 ml), and oxalic acid (16 mg) was added thereto, followed by stirring. The resulting crystals were collected by filtration to obtain 1-(3,5-difluorophenyl)-2-[5-(pyridin-3-ylmethoxy)-1,3-dihydro-2H-benzimidazol-2-ylidene]-3-phenylpropane-1,3-dione oxalate (35 mg).

Example 403

Into a dichloromethane solution (5 ml) containing the compound (0.13 g) obtained in Example 136 was added 80% mcpba (0.14 g), followed by 2 hours of stirring at room temperature. The reaction solution was washed with sodium hydrogen sulfite aqueous solution and sodium hydrogen carbonate aqueous solution successively, and the organic layer was dried over anhydrous magnesium sulfate. The solvent was evaporated under reduced pressure and the resulting residue was recrystallized from ethyl acetate-hexane (1:1 (v/v)) to obtain 1-(3,5-difluorophenyl)-3-phenyl-2-(5-phenylmethanesulfonyl-1,3-dihydro-2H-benzimidazol-2-ylidene)propane-1,3-dione (94 mg).

Example 404

A chloroform solution (3 ml) containing the compound (145 mg) obtained in Example 239 was cooled with ice and 80% mcpba (80 mg) was added thereto, followed by 1 hour of stirring at room temperature. The reaction solution was washed with sodium hydrogen sulfite aqueous solution and sodium hydrogen carbonate aqueous solution successively, and dried over anhydrous magnesium sulfate, and the solvent was evaporated under reduced pressure. Then, the resulting residue was purified by silica gel column chromatography to obtain 1-(3,5-difluorophenyl)-3-phenyl-2-{5-[(1-oxidopyridin-3-ylmethyl)amino]-1,3-dihydro-2H-benzimidazol-2-ylidene}propane-1,3-dione (92 mg) from the fractions eluted with chloroform-methanol (100:1 (v/v)).

Example 405

Into a THF/water=1:1 solution (4 ml) of the compound (62 mg) obtained in Example 131 was added acetic acid (2 ml), followed by 4 hours of stirring at room temperature. Thereto was added a saturated sodium hydrogen carbonate aqueous solution, followed by extraction with chloroform and drying over anhydrous magnesium sulfate. The organic layer was concentrated under reduced pressure and the obtained residue was purified by silica gel column chromatography (eluent: chloroform:methanol=20:1 (v/v)) to obtain 1-(3,5-difluorophenyl)-2-(5-hydroxymethyl-1,3-dihydro-2H-benzimidazol-2-ylidene)-3-phenylpropane-1,3-dione (43 mg, 89%).

Example 406

Into an ethanol solution (6 ml) containing the compound (0.30 g) obtained in Example 393 was added platinum oxide (0.03 g), followed by 8.5 hours of stirring at room temperature under hydrogen atmosphere. After solid matter in the reaction solution was removed by filtration and the filtrate was evaporated under reduced pressure, the resulting residue was purified by silica gel column chromatography (eluent: chloroform:methanol=100:3 (v/v)) to obtain 2-{5-[(1H-benzimidazol-5-ylmethyl)amino]-1,3-dihydrobenzimidazol-2-ylidene}-1-(3,5-difluorophenyl)-3-phenylpropane-1,3-dione (24 mg, 12%).

Example 407

Into an acetonitrile solution (5 ml) containing the compound (160 mg) obtained in Example 196 was added phenyl isothiocyanate (60 mg), followed by 5 hours of stirring at room temperature. The formed crystals were collected by filtration, washed with a small amount of diethyl ether, and dried to obtain 1-{2-[1-(3,5-difluorobenzoyl)-2-oxo-2-phenylethylidene]-2,3-dihydro-1H-benzimidazol-5-yl}-3-phenylthiourea (0.19 g).

Example 408

To an acetonitrile solution (10 ml) of nicotinoyl chloride hydrochloride (356 mg) were added sodium azide (325 mg) and triethylamine (0.836 ml), followed by 1.5 hours of stirring under ice cooling. Thereto was added water, followed by extraction with diethyl ether. After drying with anhydrous magnesium sulfate, the organic layer was concentrated under reduced pressure and toluene (10 ml) was added to the obtained residue, followed by 1 hour of heating under refluxing. After cooling to room temperature, an acetonitrile solution (5 ml) of the compound (255 mg) obtained in Example 196 was added and the whole was stirred for 18 hours at room temperature. The reaction solution was concentrated under reduced pressure and the obtained residue was purified by silica gel column chromatography (eluent: chloroform:methanol=10:1 (v/v)) and recrystallized (chloroform:methanol:hexane) to obtain 1-(2-[1-(3,5-difluorobenzoyl)-2-oxo-2-phenylethylidene]-2,3-dihydro-1H-benzimidazol-5-yl)-3-pyridin-3-ylurea (108 mg, 42%).

Example 409

Into a dichloromethane solution (5 ml) of the compound (174 mg) obtained in Example 405 were added NMO (100 mg) and MS4A, followed by 10 minutes of stirring at room temperature. TPAP (8 mg) was further added thereto, followed by 30 minutes of stirring at room temperature. The reaction solution was purified by silica gel column chromatography (eluent: chloroform:methanol=40:1 (v/v)) to obtain 2-[1-(3,5-difluorobenzoyl)-2-oxo-2-phenylethylidene]-2,3-dihydro-1H-benzimidazol-5-carbaldehyde (76 mg, 44%).

Example 427

To a solution of N-{2-[1-benzoyl-2-(3,5-difluorophenyl)-2-oxoethylidene]-2,3-dihydro-1H-benzimidazol-5-yl}-4-methylbenzosulfonamide (376 mg), dichloromethane (40 ml) and methanol (10 ml) was added 2M trimethylsilyldiazomethane hexane solution (1.0 ml), and the reaction solution was stirred at room temperature for 15 hours. The solvent was evaporated under reduced pressure and the obtained residue was subjected to silica gel column chromatography and eluted with chloroform to obtain N-(2-[1-benzoyl-2-(3,5-difluorophenyl)-2-oxoethylidene]-2,3-dihydro-1H-benzimidazol-5-yl)-N,4-dimethylbenzosulfonamide (310 mg). The obtained crude crystals were recrystallized from ethyl acetate-hexane to obtain crystals (181 mg, 47%).

Example 434

To a solution of 2-(5-amino-1,3-dihydro-2H-benzimidazol-2-ylidene)-1-(3,5-difluorophenyl)-3-phenylpropane-1,3-dione (400 mg) and ethanol (10 ml) was added hydroxymethylbenzotriazole (168 mg) at room temperature, and the reaction solution was stirred at room temperature for 20 hours. The reaction solution was filtered and the resulting solid matter was dissolved in THF (10 ml). Thereto was added sodium borohydride (78 mg) at room temperature and the reaction mixture was stirred at room temperature for 3 hours.

The reaction solution was diluted with ethyl acetate (10 ml) and the organic layer was washed with saturated sodium hydrogen carbonate aqueous solution, water and saturated sodium chloride aqueous solution. The organic layer was dried over anhydrous sodium sulfate and the solvent was evaporated under reduced pressure. The obtained residue was subjected to silica gel column chromatography and eluted with chloroform-methanol (100:1 (v/v)) to obtain 1-(3,5-difluorophenyl)-2-[5-methylamino-1,3-dihydro-2H-benzimidazol-2-ylidene]-3-phenylpropane-1,3-dione (163 mg, 48%).

Example 447

Into a dichloromethane solution containing 2-[5-(4-aminobenzylamino)-1,3-dihydro-2H-benzimidazol-2-ylidene]-1-(3,5-difluorophenyl)-3-(3-methylphenyl)propane-1,3-dione (0.28 g) and 2-chloro-1-methylpyridinium iodide (0.17 g) were added N,N-diisopropylethylamine (0.23 ml) and N,N'-(di-tert-butoxycarbonyl)thiourea (0.18 g) successively, followed by about 2 days of stirring at room temperature. The reaction solution was washed with an appropriate amount of purified water and then the organic layer was dried over anhydrous magnesium sulfate. The solvent was evaporated and the obtained residue was subjected to silica gel column chromatography to obtain N,N'-(di-tert-butoxycarbonyl)-N''-[4-({2-[1-(3,5-difluorobenzoyl)-2-oxo-2-(3-methylphenyl)eth-(z)-ylidene]-2,3-dihydro-1H-benzimidazol-5-ylamino}methyl)phenyl]guanidine (0.31 g) from the fractions eluted with ethyl acetate-hexane (1:2 (v/v)).

Example 448

Into an ethyl acetate solution (3 ml) containing the compound (0.3 g) obtained in Example 447 was added dropwise 4M hydrogen chloride-ethyl acetate solution (3 ml), followed by about 2.5 hours of stirring at room temperature. The resulting white crystals were collected by filtration to obtain N-[4-({2-[1-(3,5-difluorobenzoyl)-2-oxo-2-(3-methylphenyl)eth-(z)-ylidene]-2,3-dihydro-1H-benzimidazol-5-ylamino}methyl)phenyl]guanidine hydrochloride (0.21 g).

The following tables show compounds obtained in the above Reference Examples and Examples and physicochemical properties thereof.

TABLE 9

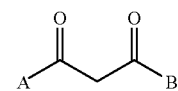

| Rex | A | B | DAT |
|-----|---|---|-----|
| 1 | Ph | 2-Me-1,3-Thiaz-4-yl | FA:246 |
| 2 | Ph | 3-Mo-1-yl(CH$_2$)$_2$O | FA:354 |
| 3 | Ph | 3-Me$_2$N-Ph | FA:268 |
| 4 | Ph | Me(PhCH$_2$)NCH$_2$ | FA:358 |
| 5 | Py-3-yl | 3,5-diF-Ph | FA:262 |
| 6 | Ph | 3,5-diF-Ph | FA:261 |
| 7 | 5-PhCH$_2$O-Py-3-yl | 3,5-diF-Ph | FA:368 |
| 8 | 5-Me-Py-3-yl | 3,5-diF-Ph | FA:276 |
| 9 | 1-Me-benzoIM-5-yl | 3,5-diF-Ph | FA:315 |
| 10 | 6-Me-Py-3-yl | 3,5-diF-Ph | FA:276 |

TABLE 10

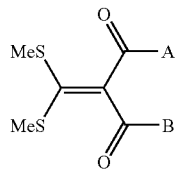

| Rex | A | B | DAT (FA:) |
|---|---|---|---|
| 11 | Ph | 2-Me-1,3-Thiaz-4-yl | 350 |
| 12 | Ph | Py-4-yl | 330 |
| 13 | Ph | Py-3-yl | 330 |
| 14 | Ph | 3-Mo-1-yl(CH$_2$)$_2$O | 458 |
| 15 | Ph | 3-Me$_2$N-Ph | 371 |
| 16 | Ph | Me(PhCH$_2$)NCH$_2$ | 462 |
| 17 | Py-3-yl | 3,5-diF-Ph | 366 |
| 18 | Ph | 3,5-diF-Ph | 261 |
| 19 | 5-PhCH$_2$O-Py-3-yl | 3,5-diF-Ph | 368 |
| 20 | 5-Me-Py-3-yl | 3,5-diF-Ph | 380 |
| 21 | 1-Me-benzoIM-5-yl | 3,5-diF-Ph | 419 |
| 22 | 6-Me-Py-3-yl | 3,5-diF-Ph | 380 |

TABLE 11

| Rex | Str | DAT |
|---|---|---|
| 23 | | FA:251 |
| 24 | | EI:263 |
| 55 | 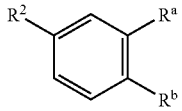 | FA:263 |

TABLE 12

| Rex | R$^2$ | R$^a$ | R$^b$ | DAT |
|---|---|---|---|---|
| 25 | Py-3-ylCH$_2$NHSO$_2$ | NO$_2$ | NH$_2$ | FA:309 |
| 26 | Py-3-ylCH=CH | NO$_2$ | NH$_2$ | FA:242 |
| 27 | Py-3-ylCH$_2$NHSO$_2$ | NH$_2$ | NH$_2$ | FA:279 |
| 28 | Py-3-ylCH$_2$O | NO$_2$ | NH$_2$ | FA:246 |
| 29 | Py-3-ylCH$_2$O | NH$_2$ | NH$_2$ | FA:216 |
| 30 | Py-3-yl(CH$_2$)$_2$ | NH$_2$ | NH$_2$ | FA:214 |
| 31 | Py-3-ylCH=CH | NO$_2$ | Cl | FN:261 |

TABLE 12-continued

| Rex | R$^2$ | R$^a$ | R$^b$ | DAT |
|---|---|---|---|---|
| 56 | 4-MeO-Ph | NO$_2$ | NH$_2$ | FN:243 |
| 57 | 4-MeO-Ph | NO$_2$ | NHAc | FN:285 |

TABLE 13

| Rex | R$^2$ | DAT |
|---|---|---|
| 32 | TBS-OCH$_2$ | FA:277 |
| 33 | Py-3-ylCH$_2$NHSO$_2$ | FA:303 |
| 34 | Py-3-ylCH$_2$O | FA:240 |
| 35 | 4-O$_2$N-PhCH$_2$O | FA:284 |
| 36 | Py-3-yl(CH$_2$)$_2$ | FA:238 |
| 58 | 4-MeO-Ph | FA:239 |
| 59 | 4-MeO-Ph(Me)NCO | FA:296 |
| 60 | PhCH$_2$O-CO | FA:267 |

TABLE 14

| Rex | R$^2$ | R$^3$ | A | DAT(FA:) |
|---|---|---|---|---|
| 37 | O$_2$N | H | Ph | 282 |
| 38 | O$_2$N | H | 4-MeO-Ph | 312 |
| 39 | O$_2$N | H | 2-MeO-Ph | 312 |
| 40 | O$_2$N | H | 2-Cl-Ph | 316 |
| 41 | O$_2$N | H | 2,3-diMeOPh | 342 |
| 42 | O$_2$N | H | Thiop-2-yl | 286 |
| 43 | O$_2$N | H | 3,5-diF-Ph | 318 |
| 44 | O$_2$N | Cl | 3,5-diF-Ph | 352 |
| 45 | H | H | 3,5-diF-Ph | 273 |
| 46 | Ac | H | Ph | 279 |
| 47 | PhCH$_2$O | H | Ph | 343 |
| 48 | PhCH$_2$S | H | Ph | 359 |
| 49 | HOCH$_2$ | H | Ph | 267 |
| 50 | TBS-OCH$_2$ | H | Ph | 381 |
| 51 | Py-3-ylCH$_2$NHSO$_2$ | H | Ph | 407 |
| 52 | Py-3-ylCH$_2$O | H | 3,5-diF-Ph | 380 |
| 53 | 4-O$_2$N-PhCH$_2$O | H | 3,5-diF-Ph | 424 |
| 54 | Py-3-yl(CH$_2$)$_2$ | H | 3,5-diF-Ph | 378 |
| 61 | 4-MeO-Ph | H | 3-Me-Ph | 357 |
| 62 | O$_2$N | H | 3-Me-Ph | 296 |
| 63 | 4-MeO-Ph(Me)NCO | H | 3,5-diF-Ph | 436 |
| 64 | PhCH$_2$O-CO | H | 3,5-diF-Ph | 407 |

TABLE 15

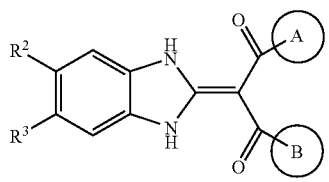

| EX | R² | R³ | A | B | Sa | DAT |
|---|---|---|---|---|---|---|
| 1 | Cl | H | Ph | Ph | — | FA:375 |
| 2 | O₂N | H | Ph | Ph | — | FA:386 |
| 3 | Me | H | Ph | Ph | — | FA:355 |
| 4 | H | H | 3-F-Ph | 3-F-Ph | — | FA:377, N1:7.30-7.33(2H,m), 7.74-7.76(2H,m), 13.15 (2H,s) |
| 5 | H | H | 3,4-diCl-Ph | 3,4-diCl-Ph | — | FA:479 |
| 6 | H | H | Fu-2-yl | Fu-2-yl | — | FA:321 |
| 7 | H | H | Thiop-2-yl | Thiop-2-yl | — | FA:353 |
| 8 | H | H | 2-MeO-Ph | 2-MeO-Ph | — | FA:401 |
| 9 | H | H | 3-O₂N-Ph | 3-O₂N-Ph | — | FA:431, N1:7.80-7.82(2H,m), 8.00-8.01(2H,m), 13.28(2H,s) |
| 10 | Me | Me | Ph | Ph | — | FA:369 |
| 11 | H | H | 3-F₃C-Ph | 3-F₃C-Ph | — | FA:477 |
| 12 | H | H | 3-MeOCO-Ph | 3-MeOCO-Ph | — | FA:457 |
| 13 | H | H | 3-Cl-CH₂-Ph | 3-Cl-CH₂-Ph | — | FA:437, N1:4.59(4H,s), 7.73-7.76(2H,m), 13.13(2H,s) |
| 14 | F | H | Ph | Ph | — | FA:359 |
| 15 | H | H | 3-CN-Ph | 3-CN-Ph | — | FA:391 |
| 16 | H | H | 3-(PhCO)Ph | 3-(PhCO)Ph | — | FA:549 |
| 17 | H | H | 3-AcO-Ph | 3-AcO-Ph | — | FA:457 |
| 18 | H | H | 4-iPr-Ph | 4-iPr-Ph | — | N1:1.03(d,6H,J=9), 2.68(m,1H), 13.11(m,2H) |
| 19 | F | H | 3-Me-Ph | 3-Me-Ph | — | FA:387, N1:2.11(6H,s), 6.17-7.18(9H,m), 7.50-7.73(2H,m), 13.14-13.19(2H,m) |
| 20 | MeO | H | 3-Me-Ph | 3-Me-Ph | — | FA:399 |
| 21 | H | H | 3,5-diF-Ph | 3,5-diF-Ph | — | FA:413 |
| 173 | H₂N | Cl | 3,5-diF-Ph | 3-Me-Ph | — | FA:440 |
| 429 | 4-AcNH-PhCH₂NH | Cl | 3,5-diF-Ph | 3-Me-Ph | — | FA:587 |

TABLE 16

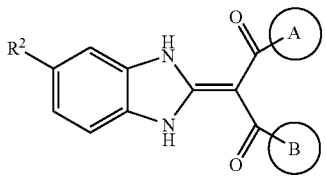

| EX | R² | A | B | Sa | DAT |
|---|---|---|---|---|---|
| 22 | PhCOCH₂OCO | Ph | Ph | — | FA:503 |
| 23 | PhCO | Ph | Ph | — | FA:445 |
| 26 | H | Ph | 3,5-diF-Ph | — | FA:377, N1:7.30-7.34(4H,m), 7.74-7.76(2H,m), 13.15(2H,s) |
| 27 | H | 3-Me-Ph | Ph | — | FA:355, N1:2.10(3H,s), 7.72-7.74(2H,m), 13.11(2H,s) |
| 28 | H | 3-O₂N-Ph | Ph | — | FA:386, N1:7.74-7.79(3H,m), 7.93-7.98(2H,m), 13.20(2H, s) |
| 29 | H | Ph | 3,5-diMe-Ph | — | FA:369, N1:2.07(6H,s), 6.68(1H,s), 13.11(2H,s) |
| 30 | H | Ph | 3-AcO-Ph | — | FA:399 |
| 31 | H | Ph | 3-Br-Ph | — | FA:419, N1:6.99-7.03(1H,m), 7.73-7.75(2H,m), 13.12(2H,s) |
| 32 | H | Ph | 2,6-diF-Ph | — | FA:377 |

TABLE 17

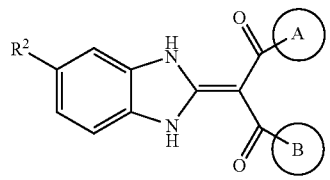

| EX | R² | A | B | Sa | DAT |
|---|---|---|---|---|---|
| 33 | H | Ph | 3-(MeOCO)Ph | — | FA:399 |
| 34 | MeOCO | Ph | Ph | — | FA:399 |
| 35 | H | 3,4-diF-Ph | 3-O₂N-Ph | — | FA:422, N2:6.46-6.56(1H,m), 6.83-6.93(2H,m), 7.30-7.60(5H,m), 7.72-7.87(1H,m), 7.98-8.22(2H,m), 12.79(2H,s) |
| 36 | H | Ph | 3,5-diCl-Ph | — | FA:342, N1:7.28-7.33(5H,m), 7.74-7.77(2H,m), 13.15(2H,s) |
| 37 | O₂N | 3,5-diF-Ph | Ph | — | FA:422 |
| 38 | H | 3,5-diF-Ph | Thiop-2-yl | — | FA:383 |
| 39 | H | 3-(Cl-CH₂)Ph | Ph | — | FA:389 |
| 40 | H | 3-H₂N-Ph | 3,5-diF-Ph | HCl | FA:392, N1:6.90-7.24(9H,m), 7.71-7.79(2H,m), 13.10(2H,s) |
| 41 | H | 3-H₂N-4-Me-Ph | 3,5-diF-Ph | HCl | FA:406 |
| 42 | H₂N | Ph | Ph | — | FA:356 |
| 43 | H | 3-H₂N-Ph | Ph | — | FA:356 |
| 44 | H | Ph | 3-(EtCONH)Ph | — | FA:412 |
| 45 | H | 3-(MeCONH)Ph | 3-(MeCONH)Ph | — | FA:455 |
| 46 | PhCONH | Ph | Ph | — | FA:460 |
| 47 | H | Ph | 3-{Ph(CH₂)₄CONH}Ph | — | FA:516 |
| 48 | H | 3(Py-4-ylCH₂CONH)Ph | 3,5-diF-Ph | HCl | FA:511 |
| 49 | H | 3,5-diF-Ph | 3-(Et₂NCH₂CONH)Ph | HCl | FA:505 |
| 50 | EtCONH | Ph | Ph | — | FA:412 |
| 51 | PhCH₂CONH | Ph | Ph | — | FA:474 |
| 52 | H | 3,5-diF-Ph | 3-{Et₂N(CH₂)₂CONH}Ph | HCl | FA:519 |
| 79 | H | Ph | 3-{Py-4-yl(CH₂)₂NHCH₂}Ph | HCl | FA:475 |
| 80 | H | 4-ClCH₂-Ph | 4-(Mo-4-ylCH₂)Ph | — | FA:488 |
| 81 | H | 3-{Et₂N(CH₂)₂}Ph | 3-{Et₂N(CH₂)₂}Ph | — | FA:511 |
| 82 | H | Ph | 3-HO-Ph | — | FA:357, N1:6.45-6.48(1H,m), 9.22(1H,s), 13.04(2H,s) |
| 83 | H | IM-4-ylCH₂NH-Ph | 3,5-diF-Ph | HCl | FA:472, N1:4.28(2H,s), 6.43-7.02(7H,m), 7.25-.80(5H,m), 9.06(1H,s), 13.09(2H,s), 14.3-14.8(2H,m) |

TABLE 18

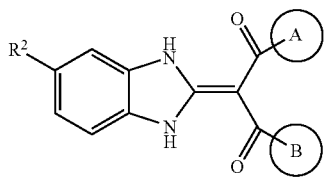

| EX | R² | A | B | Sa | DAT |
|---|---|---|---|---|---|
| 84 | H | Ph | Py-3-ylCH₂NHPh | HCl | FA:447 |
| 85 | H | Ph | 3-(4-AcNHPhCH₂NH)Ph | — | FA:503 |
| 86 | H | 3-(PrNH)Ph | 3,5-diF-Ph | HCl | FA:434, N1:0.93(3H,t), 1.45-1.65(2H,m), 3.01(2H,t), 6.90-7.37(9H,m), 7.70-7.80(2H,m), 13.13(2H,s) |
| 87 | Py-3-ylCH₂NH | Ph | Ph | — | FA:447, N1:4.32(m,2H), 6.40-6.89(3H,m), 6.99-7.43(12H,m), 7.78-8.64(3H,m), 12.79(2H,m) |
| 88 | H | 3,5-diF-Ph | 3-(Ph(CH₂)₃NH)Ph | HCl | FA:510 |
| 89 | 4-(AcNH)PhCH₂NH | Ph | Ph | — | FA:503 |
| 90 | H | 3,5-diF-Ph | 3-(MeO(CH₂)₂NH)Ph | HCl | FA:450, N1:3.13-3.25(2H,m), 3.30(3H,s), 3.42-3.50(2H,m), 6.65-7.05(7H,m), 7.25-7.37(2H,m), 7.66-7.78(2H,m), 13.02-13.18(2H,m) |
| 117 | H | 3,4,5,-triF-Ph | 3-O₂N-Ph | — | FA:440 |

TABLE 18-continued

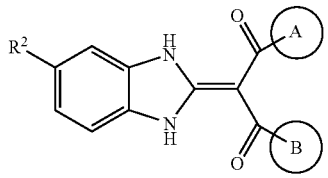

| EX | R² | A | B | Sa | DAT |
|---|---|---|---|---|---|
| 118 | H | 3,5-diF-Ph | Naph-2-yl | — | FA:427 |
| 119 | H | Benzo[b]Thiop-2-yl | Benzo[b]Thiop-2-yl | — | FA:453 |
| 120 | H | 3,5-diF-Ph | 4-Cl-3-NO₂-Ph | — | FA:456 |
| 121 | H | 3,5-diF-Ph | 3-O₂N-2-Me-Ph | — | FA:436 |
| 122 | H | 3,5-diF-Ph | Benzo[b]Thiop-2-yl | — | FA:433 |
| 123 | H | 3,5-diF-Ph | 4-CN-Ph | — | FA:402 |
| 124 | H | 3,5-diF-Ph | 3-O₂N-4-MeO-Ph | — | FA:452 |
| 125 | H | 3,5-diF-Ph | 5-O₂N-Fu-2-yl | — | FA:412 |
| 126 | PhCO-OCH₂ | Ph | Ph | — | FA:475 |
| 127 | Ac | 3,5-diF-Ph | Ph | — | FA:419 |
| 128 | 3-O₂N-PhCH₂NH | 3,5-diF-Ph | Ph | — | FA:527 |
| 129 | O₂N | 3,5-diF-Ph | 3-Me-Ph | — | FA:436 |
| 130 | 3-O₂N-PhCONH | 3,5-diF-Ph | Ph | — | FA:541 |
| 131 | TBS-OCH₂ | 3,5-diF-Ph | Ph | — | FA:521 |
| 132 | PhCH₂O | 3,5-diF-Ph | Ph | — | FA:483 |
| 133 | O₂N | 3,5-diF-Ph | 3-O₂N-Ph | — | FA:467 |
| 134 | O₂N | 3,5-diF-Ph | 3-F-Ph | — | FA:440 |
| 135 | O₂N | 3,5-diF-Ph | 3-O₂N-4-Me-Ph | — | FA:481 |
| 136 | PhCH₂S | 3,5-diF-Ph | Ph | — | FA:498 |
| 137 | Py-3-ylCH₂NHSO₂ | 3,5-diF-Ph | Ph | — | FA:547 |
| 138 | O₂N | 3,5-diF-Ph | 4-Me-Ph | — | FA:436 |

TABLE 19

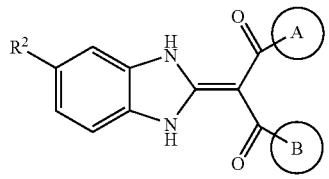

| EX | R² | A | B | Sa | DAT |
|---|---|---|---|---|---|
| 139 | O₂N | 3,5-diF-Ph | 4-F₃C-O-Ph | — | FA:506 |
| 140 | O₂N | 3,5-diF-Ph | 3-F₃C-Ph | — | FA:490 |
| 141 | O₂N | 3,5-diF-Ph | 2-F₃C-O-Ph | — | FA:505 |
| 142 | O₂N | 3,5-diF-Ph | 4-Cl-Ph | — | FA:456 |
| 143 | O₂N | 3,5-diF-Ph | 4-F-Ph | — | FA:440 |
| 144 | O₂N | 3,5-diF-Ph | 2,3-diMe-Ph | — | FA:450 |
| 145 | O₂N | 3,5-diF-Ph | 3-MeO-Ph | — | FA:452 |
| 146 | Py-3-ylCH₂O | 3,5-diF-Ph | 2,3-diMe-Ph | — | FA:512 |
| 147 | Py-3-ylCH₂O | 3,5-diF-Ph | 3-Me-Ph | — | FA:498 |
| 148 | O₂N | 3,5-diF-Ph | 2-MeO-Ph | — | FA:452 |
| 149 | O₂N | 3,5-diF-Ph | 6-Cl-Py-3-yl | — | FA:457 |
| 150 | O₂N | 3,5-diF-Ph | 3-CN-Ph | — | FA:447 |
| 151 | O₂N | 3,5-diF-Ph | Naph-1-yl | — | FA:472 |
| 152 | O₂N | 3,5-diF-Ph | 4-CN-Ph | — | FA:447 |
| 153 | O₂N | 3,5-diF-Ph | 3,4-diF-Ph | — | FA:458 |
| 154 | O₂N | 3,5-diF-Ph | 4-F₃C-Ph | — | FA:490 |
| 155 | O₂N | 3,5-diF-Ph | 3-AcO-Ph | — | FA:480 |
| 156 | O₂N | 3,5-diF-Ph | Thiop-2-yl | — | FA:428 |
| 157 | O₂N | 3,5-diF-Ph | 2,3-diMeO-Ph | — | FA:482 |
| 158 | O₂N | 3-Me-Ph | 3-Me-Ph | — | FA:414 |
| 160 | O₂N | 3,5-diF-Ph | 3-AcO-2-Me-Ph | — | FA:494 |
| 161 | 4-O₂N-PhCH₂NH | 3,5-diF-Ph | 3-Me-Ph | — | FA:541 |
| 162 | O₂N | 4-F-Ph | 3-Me-Ph | — | FA:418 |
| 163 | O₂N | 2-MeO-Ph | 3-Me-Ph | — | FA:430 |
| 164 | O₂N | 2,3-diMe-Ph | 3-Me-Ph | — | FA:428 |
| 165 | Py-3-yl(CH₂)₂ | 3,5-diF-Ph | 3-Me-Ph | — | FA:496 |
| 166 | 4-O₂N-PhCH₂O | 3,5-diF-Ph | 3-Me-Ph | — | FA:541 |
| 167 | H | 3,4,5,-triF-Ph | 3-H₂N-Ph | HCl | FA:410 |
| 168 | H | 3,5-diF-Ph | 3-H₂N-2-Me-Ph | HCl | FA:406 |
| 169 | H | 3,5-diF-Ph | 3-H₂N-4-Cl-Ph | — | FA:426 |

TABLE 19-continued

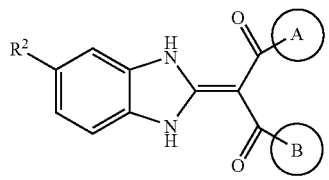

| EX | R² | A | B | Sa | DAT |
|---|---|---|---|---|---|
| 170 | H | 3,5-diF-Ph | 3-H₂N-4-MeO-Ph | — | FA:422 |
| 171 | H | 3,5-diF-Ph | 5-H₂N-Fu-2-yl | — | FA:382 |

TABLE 20

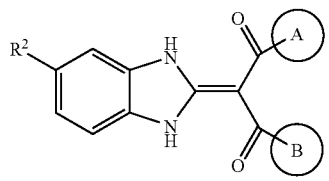

| EX | R² | A | B | Sa | DAT |
|---|---|---|---|---|---|
| 159 | 4-O₂N-PhCH₂NH | 3,5-diF-Ph | 2,3-diMe-Ph | | FA:555 |
| 172 | 3-H₂N-PhCONH | 3,5-diF-Ph | Ph | — | FA:511 |
| 174 | 3-H₂N-PhCH₂NH | 3,5-diF-Ph | Ph | — | FA:497 |
| 175 | H₂N | 3,5-diF-Ph | 3,5-diF-Ph | — | FA:428 |
| 176 | H₂N | 3,5-diF-Ph | 3-H₂N-4-Me-Ph | — | FA:421 |
| 177 | H₂N | 3,5-diF-Ph | 3-H₂N-Ph | — | FA:407 |
| 178 | H₂N | 3,5-diF-Ph | 2-Me-Ph | — | FA:406 |
| 179 | H₂N | 3,5-diF-Ph | 3-F₃C-O-Ph | — | FA:476 |
| 180 | H₂N | 3,5-diF-Ph | 3-F₃C-Ph | — | FA:460 |
| 181 | H₂N | 3,5-diF-Ph | 4-F-Ph | — | FA:410 |
| 182 | H₂N | 3,5-diF-Ph | 2,3-diMe-Ph | — | FA:420 |
| 183 | H₂N | 3,5-diF-Ph | 3-MeO-Ph | — | FA:422 |
| 184 | H₂N | 3,5-diF-Ph | 2-MeO-Ph | — | FA:422 |
| 185 | H₂N | 3,5-diF-Ph | 2,5-diF-Ph | — | FA:428 |
| 186 | H₂N | 3,5-diF-Ph | 6-CN-Py-3-yl | — | FA:427 |
| 187 | H₂N | 3,5-diF-Ph | 3,5-diMe-Ph | — | FA:420 |
| 188 | H₂N | 3,5-diF-Ph | 3-CN-Ph | — | FA:417 |
| 189 | H₂N | 3,5-diF-Ph | 4-CN-Ph | — | FA:417 |
| 190 | H₂N | 3,5-diF-Ph | Naph-1-yl | — | FA:442 |
| 191 | H₂N | 3,5-diF-Ph | 3,4-diF-Ph | — | FA:428 |
| 192 | H₂N | 3,5-diF-Ph | 5-Br-Py-3-yl | — | FA:501 |
| 193 | H₂N | 3,5-diF-Ph | 3-AcO-Ph | — | FA:450 |
| 194 | H₂N | 3,5-diF-Ph | 2,3-diMeO-Ph | — | FA:452 |
| 195 | H₂N | 3,5-diF-Ph | Thiop-2-yl | — | FA:398 |
| 196 | H₂N | 3,5-diF-Ph | Ph | — | FA:392 |
| 197 | H₂N | 3,5-diF-Ph | 3-Me-Ph | — | FA:406 |
| 198 | H₂N | 3,5-diF-Ph | 3-AcO-2-Me-Ph | — | FA:464 |
| 199 | 4-H₃N-PhCH₂NH | 3,5-diF-Ph | 3-Me-Ph | — | FA:511 |
| 200 | 4-H₂N-PhCH₂O | 3,5-diF-Ph | 3-Me-Ph | — | FA:542 |
| 201 | H₂N | 4-F-Ph | 3-Me-Ph | — | FA:388 |
| 202 | H₂N | 2-MeO-Ph | 3-Me-Ph | — | FA:400 |
| 203 | H₂N | 2,3-diMe-Ph | 3-Me-Ph | — | FA:398 |
| 204 | PhCONH | 3,5-diF-Ph | Ph | — | FA:496 |
| 205 | 4-(Et₂NCO)PhCH₂N | 3,5-diF-Ph | Ph | — | FA:581 |
| 206 | Py-2-ylCH₂CONH | 3,5-diF-Ph | Ph | — | FA:511 |
| 207 | (4-MeO-Ph)(CH₂)₂CONH | 3,5-diF-Ph | Ph | — | FA:554 |
| 208 | 3-F-PhCONH | 3,5-diF-Ph | Ph | — | FA:514 |
| 209 | 4-MeO-PhCH₂CONH | 3,5-diF-Ph | Ph | — | EA:540 |
| 210 | 4-Me₂N-PhCONH | 3,5-diF-Ph | Ph | — | FA:539 |

TABLE 21

| EX | R² | B | Sa | DAT |
|---|---|---|---|---|
| 211 | 4-Ac-PhCONH | Ph | — | FA:538 |
| 212 | 2-Me-PhCONH | Ph | — | FA:510, N1:2.42(3H, s), 6.90-7.00(3H, m), 7.11-7.21(3H, m), 7.29-7.34(4H, m), 7.38-7.40 (1H, m), 7.49(1H, d, J=7.8Hz), 7.56(1H, dd, J=8.8, 1.5Hz), 7.67(1H, d, J=8.8Hz), 8.37(1H, s), 10.45(1H, s), 13.10(1H, s), 13.14(1H, s) |
| 213 | 4-AcNH-PhCONH | Ph | — | FA:553 |
| 214 | Py-3-yl-CONH | Ph | — | FA:497 |
| 215 | 3-Cl-PhCONH | Ph | — | FA:530 |
| 216 | MeOCO(CH₂)₂CONH | Ph | — | FA:506 |
| 217 | 4-MeOCO-PhCONH | Ph | — | FA:554 |
| 218 | 4-Me-PhCH₂CONH | Ph | — | FA:524 |
| 219 | BenzoIM-5-ylCONH | Ph | — | FA:536 |
| 220 | Thiop-2-ylCOCONH | Ph | — | FA:530 |
| 221 | 3-AcNH-PhCH₂NH | Ph | — | FA:488 |
| 222 | 3-(cPrNHCO)PhCH₂NH | Ph | — | FA:565 |
| 223 | 4-(4-F-PhNHNHCO)PhCH₂NH | Ph | — | FA:634 |
| 224 | 4-H₂NCO-PhCH₂NH | Ph | — | FA:525 |
| 225 | 4-(iPrNHCO)PhCH₂NH | 4-F-Ph | — | FA:585 |
| 226 | Pyra-2-ylCONH | 3-Me-Ph | — | FA:512 |
| 227 | Py-3-ylCONH | 4-F-Ph | — | FA:515 |
| 228 | cPrNHCO | 2-MeO-Ph | — | FA:595 |
| 229 | H₂NCO | 2-MeO-Ph | — | FA:555 |
| 230 | PhO-CONH | Ph | — | FA:512 |
| 231 | MeSO₂NH | Ph | — | FA:470 |
| 232 | 4-AcNH-PhSO₂NH | Ph | — | FA:589 |
| 233 | 4-F-PhSO₂NH | 3-Me-Ph | — | FA:566 |
| 234 | 4-MeO-PhSO₂NH | 4-F-Ph | — | FA:600 |
| 235 | 3-F₃C-PhSO₂NH | 2-MeO-Ph | — | FA:551 |
| 236 | 3,5-diMe-isoxazol-4-yl-SO₂NH | 2-MeO-Ph | — | FA:587 |
| 237 | 1,2,3,4-tetrahydroisoquinolin-7-yl-SO₂NH | Ph | — | FA:587 |
| 238 | 6-F₃C-Py-3-ylCH₂NH | Ph | HCl | FA:550 |
| 239 | Py-3-ylCH₂NH | Ph | — | FA:483 |
| 240 | Me(Py-3-ylCH₂)N | Ph | — | FA:497 |
| 241 | 4-AcNH-PhCH₂NH | Ph | — | FA:539, N1:2.02(3H, s), 4.22 (2H, m), 6.34(1H, m), 6.65-7.53(15H, m), 9.88(1H, s), 12.81(2H, m) |
| 242 | 3-methyl-5-(4-aminomethylbenzylidene)-2-thioxo-tetrahydrothiophen-3-one derivative | Ph | — | FA:639 |

TABLE 21-continued

| EX | R² | B | Sa | DAT |
|---|---|---|---|---|
| 243 | (2-(3-pyridylamino-propyl)phthalimide group) | Ph | HCl | FA:669 |

TABLE 22

| EX | R² | B | Sa | DAT |
|---|---|---|---|---|
| 244 | 1-Me-5-F₃C-Pyrazo-3-ylThiop-2-ylCH₂NH | Ph | HCl | FA:636, N1:3.99(3H, s), 4.58(2H, s), 6.82-6.95(5H, m), 7.09-7.20(4H, m), 7.23 (1H, d, J=2.5Hz), 7.27-7.29 (2H, m), 7.40(1H, d, J=3.4Hz), 7.51(1H, d, J=8.7Hz), 12.89(1H, s), 12.95(1H, s) |
| 245 | Py-4-ylCH₂NH | Ph | — | FA:483, N1:4.34(2H, d, J=5.8Hz), 6.55(1H, t, J=5.8Hz), 6.68 (1H, dd, J=8.8, 2.5Hz), 6.82-6.94(4H, m), 7.09-7.18(3H, m), 7.29 (2H, d, J=8.3Hz), 7.38 (2H, d, J=5.8Hz), 7.45 (1H, d, J=8.8Hz), 8.51 (2H, d, J=5.8Hz), 12.77(1H, s), 12.88(1H, s) |
| 246 | (4-Me₂N-PhCH₂)₂N | Ph | — | FA:658 |
| 247 | 4-HOOC-PhCH₂NH | Ph | — | FA:526 |
| 248 | 3-HO-5-HOCH₂-2-Me-Py-4ylCH₂NH | Ph | — | FA:543 |
| 249 | 6-Cl-imidazo[1,2-a]Py-3-ylCH₂NH | Ph | — | FA:556 |
| 250 | IM-3-ylCH₂NH | Ph | 2HCl | FA:472 |
| 251 | 4-AcNH-PhCH₂NH | 3-Me-Ph | — | FA:553, N1:2.02(3H, m), 2.14(3H, s), 4.21(2H, d), 6.80-7.15(10H, m), 7.25-7.55(5H, m), 9.85-9.90(1H, m), 12.76-12.90(2H, m) |
| 252 | Thiaz-2-ylCH₂NH | Ph | — | FA:489 |
| 253 | PhCOCH₂NH | Ph | — | FA:510 |
| 254 | 1-Oxido-Py-4-ylCH₂NH | Ph | — | FA:499 |
| 255 | 5-(4-Cl-Ph)Fu-2-ylCH₂NH | Ph | HCl | FA:582 |
| 256 | Thiaz-5-ylCH₂NH | Ph | 2HCl | FA:489, N1:4.77(2H, s), 6.88-6.98(3H, m), 7.11-7.21(4H, m), 7.33(2H, d, J=7Hz), 7.55(1H, br), 7.66(1H, t, J=9Hz), 7.82(1H, d, J=4Hz), 9.15(1H, d, J=9Hz), 13.10(2H, br) |
| 257 | 5,6-diCl-Py-3-yl-CH₂NH | Ph | — | FA:551 |
| 258 | Pyrazi-3-ylCH₂NH | Ph | — | FA:484 |
| 259 | 5-Br-Py-3-ylCH₂NH | Ph | — | FA:561 |
| 260 | Pyrim-5-ylCH₂NH | Ph | — | FA:484 N1:4.35(2H, m), 6.47-9.12(15H, m), 12.84(2H, m) |
| 261 | 6-Me-Py-3-ylCH₂NH | Ph | — | FA:497 |

TABLE 22-continued

| EX | R² | B | Sa | DAT |
|---|---|---|---|---|
| 262 | 2-Me-Py-3-ylCH₂NH | Ph | — | FA:497 |
| 263 | 3-F₃C-PhCH₂NH | Ph | — | FA:550 |
| 264 | 2-OH-PhCH₂NH | Ph | — | FA:498 |
| 265 | 1-Me-IM-2-ylCH₂NH | Ph | — | FA:486 |
| 266 | 3-HOOC-PhCH₂NH | Ph | — | FA:526 |
| 267 | 3-MeO-PhCH₂NH | Ph | — | FA:512 |
| 268 | 4-O₂N-PhCH₂NH | Ph | — | FA:527 |
| 269 | Py-3-ylCH₂NHCH₂ | Ph | — | FA:497 |
| 270 | 4-F-PhCH₂NH | Ph | — | FA:500 |
| 271 | 6-AcNH-Py-3-ylCH₂NH | Ph | — | FA:540 |
| 272 | 4-HO-PhCH₂NH | Ph | — | FA:498 |
| 273 | PhCH₂NH | Ph | — | FA:482 |
| 276 | 4-AcNH-PhNHCH₂ | Ph | — | FA:539 |
| 277 | Py-3-ylNHCH₂ | Ph | — | FA:483 |
| 278 | 4-AcNH-PhCH₂NH | 3-F-Ph | — | FA:557 |
| 279 | (Py-3-yl)(CH₂)₂NHCH₂ | Ph | — | FA:511 |
| 280 | 4-Br-Thiop-2-ylCH₂NH | Ph | — | FA:567 |
| 281 | Py-3-ylCH₂NH | 3-F-Ph | — | FA:501 |
| 282 | 2-H₂N-Py-3-ylCH₂NH | Ph | HCl | FA:498 |
| 283 | 4-HO-Ph—CH(CO₂Me)—NH-Et | Ph | HCl | FA:584 |
| 284 | 4-CN-PhCH₂NH | Ph | — | FA:507 |
| 285 | 4-MeOCO-PhCH₂NH | Ph | — | FA:540 |
| 274 | 4-AcNH-PhCH₂NH | 3-H₂N-4-Me-Ph | — | FA:568, N1:1.89(3H, s), 2.02(3H, s), 4.21(2H, m), 4.77(2H, s), 6.25-6.95(9H, m), 7.25-7.55 (5H, m), 9.88(1H, s), 12.68(1H, s), 12.77(1H, s) |
| 275 | 4-AcNH-PhCH₂NH | 3-H₂N-Ph | — | FA:554, N1:2.02(3H, s), 4.21(2H, m), 5.00(2H, s), 6.45-7.00(10H, m), 7.28-7.56(5H, m), 9.88(1H, s), 12.70(1H, s), 12.79(1H, s) |
| 286 | 4-AcNH-PhCH₂NH | 4-Me-Ph | — | FA:553 |

TABLE 23

| EX | R² | B | Sa | DAT |
|---|---|---|---|---|
| 287 | 4-AcNH-PhCH₂NH | 2-F₃C-O-Ph | — | FA:622 |
| 288 | 4-AcNH-PhCH₂NH | 3-Cl-Ph | — | FA:573 N1:2.02(3H, s), 4.22(2H, d, J=4.9Hz), 6.36(1H, t, J=5.8Hz), 6.70(1H, dd, J=8.8, 2.0Hz), 6.88-6.92(3H, m), 6.98(1H, tt, J=8.3, 2.4Hz), 7.12-7.16(1H, m), 7.20-7.26(3H, m), 7.32(2H, d, J=8.7Hz), 7.44(1H, d, J=8.8Hz), 7.53(2H, d, J=8.3Hz), 9.88(1H, s), 12.81(1H, s), 12.90(1H, s) |
| 289 | 4-AcNH-PhCH₂NH | 4-F-Ph | — | FA:557 N1:2.01(3H, s), 4.21(2H, m), 6.34(1H, s), 6.65-7.53(14H, m), 9.87(1H, s), 12.80(2H, m) |

TABLE 23-continued

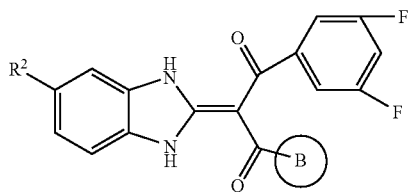

| EX | R² | B | Sa | DAT |
|---|---|---|---|---|
| 290 | 4-AcNH-PhCH₂NH | 2,3-diMe-Ph | — | FA:567, N1:2.01(3H, s), 2.02(3H, s), 2.10(3H, s), 4.21(2H, s), 6.35(1H, br), 6.67-6.73(3H, m), 6.77-6.94(5H, m), 7.31(2H, d, J=9Hz), 7.43 (1H, d, J=9Hz), 7.52(2H, d, J=9Hz), 9.88(1H, s), 12.85 (1H, s), 12.94(1H, s) |
| 291 | 4-AcNH-PhCH₂NH | 3-MeO-Ph | — | FA:569 N1:2.02(3H, s), 3.66(3H, s), 4.22(2H, d, J=5.3Hz), 6.35(1H, t, J=5.6Hz), 6.67(1H, dd, J=8.8, 2.5Hz), 6.71(1H, dd, J=8.3, 2.5Hz), 6.79(1H, s), 6.86-6.87(4H, m), 6.92-6.97(1H, m), 7.02(1H, t, J=7.8Hz), 7.31(2H, d, J=8.3Hz), 7.42(1H, d, J=8.8Hz), 7.53(2H, d, J=8.3Hz), 9.89(1H, s), 12.78(1H, s), 12.87(1H, s) |
| 292 | 4-HO-3-O₂N-PhNHCH₂ | Ph | — | FA:543 |
| 293 | 4-AcNH-PhCH₂NH | 2-MeO-Ph | — | FA:569, N1:2.02(3H, s), 3.63(3H, S), 4.22(2H, d, J=5.3Hz), 6.34(1H, t, J=5.9Hz), 6.58 (1H, d, J=8.3Hz), 6.61-6.71 (2H, m), 6.75-6.78(2H, m), 6.87-6.92(2H, m), 7.00-7.07(2H, m), 7.31 (2H, d, J=8.3Hz), 7.42(1H, d, J=8.8Hz), 7.53(2H, d, J=8.8Hz), 9.88(1H, s), 12.84(1H, s), 12.94(1H, s) |
| 294 | 4-AcNH-PhCH₂NH | 3,5-diMe-Ph | — | FA:567 |
| 295 | 4-AcNH-PhCH₂NH | 3-CN-Ph | — | FA:564 |
| 296 | 4-AcNH-PhCH₂NH | 2-F-Ph | — | FA:557, N2:2.19(3H, s), 4.35(2H, s), 6.46-7.87(15H, m), 9.93(1H, s), 12.65(2H, m) |
| 297 | 4-AcNH-PhCH₂NH | 4-CN-Ph | — | FA:564, N1:2.01(3H, s), 4.21(2H, s), 6.37(1H, s), 6.67-7.87(14H, m), 9.88(1H, s), 12.86(2H, m) |
| 298 | 4-AcNH-PhCH₂NH | Naph-1-yl | — | FA:589, N1:2.02(3H, s), 4.23(2H, s), 6.38(1H, br), 6.47-6.58(3H, m), 6.71(1H, dd, J=2Hz, 9Hz), 6.91(1H, s), 7.17-7.26(2H, m), 7.32(2H, d, J=9Hz), 7.42-7.54(5H, m), 7.64(1H, d, J=8Hz), 7.75(1H, d, J=8Hz), 8.14(1H, d, J=8Hz), 9.89(1H, s), 12.90(1H, s), 12.99(1H, s) |
| 299 | 4-AcNH-PhCH₂NH | 3,4-diF-Ph | — | FA:575 |
| 300 | 3-CN-PhCH₂NH | 4-F-Ph | — | FA:525 |
| 301 | 4-AcNH-PhCH₂NH | 2-Cl-Ph | — | FA:573, N1:2.02(3H, s), 4.22(2H, d, J=5.3Hz), 6.38(1H, t, J=5.9Hz), 6.70(1H, dd, J=8.8, 2.0Hz), 6.83-6.96(4H, m), 7.05-7.17(4H, m), 7.31(2H, d, J=8.3Hz), 7.44(1H, d, J=8.3Hz), 7.53(2H, d, J=8.8Hz), 9.88(1H, s), 12.87(1H, s), 12.97(1H, s) |
| 302 | 4-AcNH-PhCH₂NH | 2,5-diF-Ph | — | FA:575, N1:2.02(3H, s), 4.22(2H, m), 6.30-6.75(2H, m), 6.82-7.10(7H, m), 7.27-7.57(5H, m), 9.88(1H, s), 12.80-13.05(2H, m) |
| 303 | 4-AcNH-PhCH₂NH | 2-F₃C-Ph | — | FA:607, N1:2.02(3H, s), 4.22(2H, m), 6.38(1H, m), 6.60-6.95(5H, m), 7.22-7.56(9H, m), 9.88(1H, s), 12.85-13.00(2H, m) |
| 304 | 4-AcNH-PhCH₂NH | 6-Cl-Py-3-yl | — | FA:574 |
| 305 | 4-AcNH-PhCH₂NH | 5-Br-Py-3-yl | — | FA:618 |
| 306 | 4-AcNH-PhCH₂NH | 3-Br-Ph | — | FA:616 |
| 307 | 4-AcNH-PhCH₂NH | 3-AcO-Ph | — | FA:597 |
| 308 | 4-HO-3-MeO-PhCH₂NH | 3,5-diMeO-Ph | — | FA:588 |
| 309 | 4-HOOC-PhCH₂NH | 4-F-Ph | — | FA:544 |
| 310 | 4-AcNH-PhCH₂NH | Thiop-2-yl | — | FA:545 |
| 311 | 4-AcNH-PhCH₂NH | 2,3-diMeO-Ph | — | FA:599:N1:2.02(3H, s), 3.65(3H, S), 3.66(3H, s), 4.21(2H, d, J=5.8Hz), 6.35(1H, t, J=5.9Hz), 6.59-6.61(1H, m), 6.71(1H, dd, J=2.8, 8.8Hz), 6.74-6.79(4H, m), 6.85-6.91(2H, m), 7.32(2H, d, J=8.3Hz), 7.43(1H, d, J=8.8Hz), 7.53(2H, d, J=8.8Hz), 9.88(1H, s), 12.84(1H, s), 12.93(1H, s) |

TABLE 24

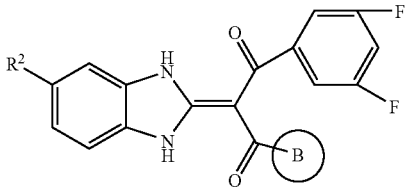

| EX | R² | B | Sa | DAT |
|---|---|---|---|---|
| 312 | 4-[Mo-4-yl(CH₂)₂O]PhCH₂NH | 4-F-Ph | — | FA:629 |
| 313 | 4-HO-PhCH₂NH | 2-MeO-Ph | — | FA:528 |
| 314 | 3-EtO-4-MeO-PhCH₂NH | 3-Me-Ph | — | FA:570 |
| 315 | 4-(Me₂N(CH₂)₃O)PhCH₂NH | 3-Me-Ph | — | FA:597 |
| 316 | 1,3-benzoThiaz-6-ylCH₂NH | 3-Me-Ph | — | FA:553 |
| 317 | 4-[Mo-4-yl(CH₂)₂O]PhCH₂NH | 2-MeO-Ph | — | FA:641 |
| 318 | 3-HOOC-PhCH₂NH | 2-MeO-Ph | — | FA:556 |
| 319 | 3-CN-PhCH₂NH | 3-Me-Ph | — | FA:521 |
| 320 | 1-PhCH₂-Pipe-4-ylCH₂NH | Ph | HCl | FA:579 |
| 321 | PhCH₂NH | Ph | — | FA:482 |
| 322 | Naph-2-yl-CH₂NH | Ph | — | FA:532 |
| 323 | 4-Me-PhCH₂NH | Ph | — | FA:496 |
| 324 | 3-MeO-PhCH₂NH | Ph | — | FA:512 |
| 325 | 2-CN-PhCH₂NH | Ph | — | FA:507 |
| 326 | 3-F₃C-PhCH₂NH | Ph | — | FA:550 |
| 327 | 3-Br-PhCH₂NH | Ph | — | FA:560 |
| 328 | 4-HO-PhCH₂NH | Ph | — | FA:498 |
| 329 | 4-O₂N-PhCH₂NH | Ph | — | FA:527 |
| 330 | 4-MeS-PhCH₂NH | Ph | — | FA:528 |
| 331 | 2-MeO-Naph-1-yl-CH₂NH | Ph | — | FA:562 |

TABLE 25

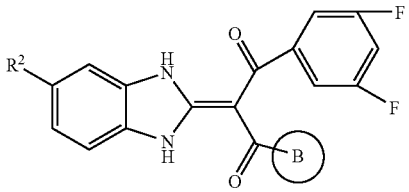

| EX | R² | B | Sa | DAT |
|---|---|---|---|---|
| 332 | 5,6,7,8,-tetrahydro-Naph-2-yl-CH₂NH | Ph | — | FA:536 |
| 333 | 2,3-dihydro-benzo[b]Fu-5-ylCH₂NH | Ph | — | FA:524 |
| 334 | ![benzodioxole-CH₂NH] | Ph | — | FA:526 |

TABLE 25-continued

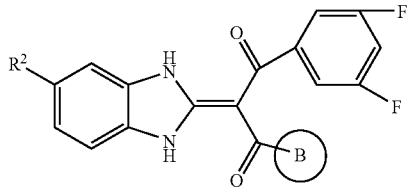

| EX | R² | B | Sa | DAT |
|---|---|---|---|---|
| 335 | ![benzodioxine-CH₂NH] | Ph | — | FA:540 |
| 336 | 3,4-diMeO-PhCH₂NH | Ph | — | FA:542 |
| 337 | 2,5-diF-PhCH₂NH | Ph | — | FA:518 |
| 338 | 3,5-diF₃C-PhCH₂NH | Ph | — | FA:618 |
| 339 | 5-Et-Fu-2-ylCH₂NH | Ph | — | FA:500 |
| 340 | Thiop-3-ylCH₂NH | Ph | — | FA:488 |
| 341 | 1-MeO-CO(CH₂)₂-Pyrr-2-ylCH₂NH | Ph | — | FA:557 |
| 342 | Pen-NH | Ph | — | FA:462 |
| 343 | PhCH₂O(CH₂)₂NH | Ph | — | FA:526 |
| 344 | Ph(CH₂)₃NH | Ph | — | FA:510 |
| 345 | Me(Py-3-yl)CHNH | Ph | — | FA:497 |
| 346 | 4-Pen-PhCH₂NH | Ph | — | FA:552 |
| 347 | biPh-4-ylCH₂NH | Ph | — | FA:558 |
| 348 | 4-F₃C-PhCH₂NH | Ph | — | FA:550 |
| 349 | 2-Cl-PhCH₂NH | Ph | — | FA:516 |
| 350 | 4-MeO-CO-PhCH₂NH | Ph | — | FA:540 |
| 351 | 3-CN-PhCH₂NH | Ph | — | FA:507 |
| 352 | 4-Me₂N-PhCH₂NH | Ph | — | FA:525 |
| 353 | 4-Pyrroli-1-yl-PhCH₂NH | Ph | — | FA:551 |
| 354 | 4-PrO-PhCH₂NH | Ph | — | FA:540 |
| 355 | 4-HOCOCH₂O-PhCH₂NH | Ph | — | FA:556 |
| 356 | 4-PhO-PhCH₂NH | Ph | — | FA:574 |
| 357 | 3-(3-F₃C-PhO)PhCH₂NH | Ph | — | FA:642 |
| 358 | 4-PhCH₂O-PhCH₂NH | Ph | — | FA:588 |
| 359 | 4-biPhO-PhCH₂NH | Ph | — | FA:650 |
| 360 | 2-(4-Cl-PhS)-PhCH₂NH | Ph | — | FA:624 |
| 361 | 6-MeO-Naph-2-ylCH₂NH | Ph | — | FA:562 |
| 362 | 1-HO-Naph-2-ylCH₂NH | Ph | — | FA:548 |
| 363 | 9H-Fluoren-2-ylCH₂NH | Ph | — | FA:570 |
| 364 | 2-Cl-5-F-PhCH₂NH | Ph | — | FA:534 |
| 365 | 3,5-diHO-PhCH₂NH | Ph | — | FA:514 |
| 366 | 2-HO-3-MeO-PhCH₂NH | Ph | — | FA:528 |
| 367 | 2-HO-4-Me₂N-PhCH₂NH | Ph | — | FA:569 |
| 368 | 2-HO-5-O₂N-PhCH₂NH | Ph | — | FA:543 |
| 369 | 4-HO-3-O₂N-PhCH₂NH | Ph | — | FA:543 |
| 370 | 4-HO-3-MeO-PhCH₂NH | Ph | — | FA:528 |
| 371 | 2,4-diMeO-PhCH₂NH | Ph | — | FA:542 |
| 372 | 3-MeO-2-O₂N-PhCH₂NH | Ph | — | FA:557 |
| 373 | 4-(Mo-1-yl)-2-O₂N-PhCH₂NH | Ph | — | FA:612 |

TABLE 26

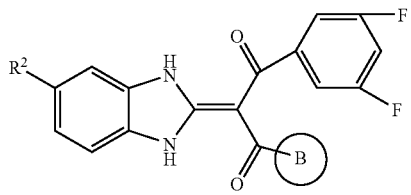

| EX | R² | B | Sa | DAT |
|---|---|---|---|---|
| 374 | 3,5-diCl-6-HO-PhCH₂NH | Ph | — | FA:566 |
| 375 | 3,4-diMeO-2-O₂N-PhCH₂NH | Ph | — | FA:587 |
| 376 | 4-MeO-5,6-diMe-PhCH₂NH | Ph | — | FA:540 |

TABLE 26-continued

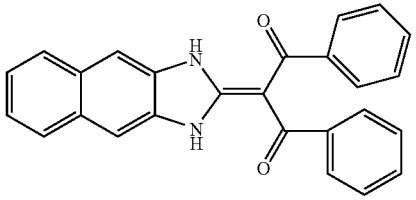

| EX | R² | B | Sa | DAT |
|---|---|---|---|---|
| 377 | 3-HO-4,5-diMeO-PhCH₂NH | Ph | — | FA:558 |
| 378 | 1-PhSO₂-Pyrr-2-ylCH₂NH | Ph | — | FA:611 |
| 379 | 5-AcOCH₂-Fu-2-ylCH₂NH | Ph | — | FA:544 |
| 380 | 5-Me-Thiop-2-ylCH₂NH | Ph | — | FA:502 |
| 381 | 5-Thiop-2-ylThiop-2-ylCH₂NH | Ph | — | FA:570 |
| 382 | 4-Br-Thiop-2-ylCH₂NH | Ph | — | FA:566 |
| 383 | 2-Ph-IM-4-ylCH₂NH | Ph | — | FA:548 |
| 384 | 2-H₂N-Py-3-ylCH₂NH | Ph | — | FA:498 |
| 385 | Indol-3-ylCH₂NH | Ph | — | FA:521 |
| 386 | 1-(4-Me-PhSO₂)indol-3-ylCH₂NH | Ph | — | FA:675 |
| 387 | 3-Me-benzo[b]Thiop-2-ylCH₂NH | Ph | — | FA:552 |
| 388 | quinolin-3-ylCH₂NH | Ph | — | FA:533 |
| 389 | 5-PhCH₂O-1H-pyrrolo[2,3-c]Py-3-ylCH₂NH | Ph | — | FA:628 |
| 390 | PrNH | Ph | — | FA:434 |
| 391 | cHex-CH₂NH | Ph | — | FA:488 |
| 392 | PhCH₂NH | Ph | — | FA:496 |
| 393 | 1-Tr-BenzoIM-5-ylCH₂NH | Ph | — | FA:550 |
| 394 | 4-AcNH-PhCH₂NH | 3-OH-Ph | — | FA:555 |
| 395 | Me(Py-3-yl)C=N | Ph | — | FA:495 |
| 396 | Me(Py-3-yl)CH₂NH | Ph | HCl | FA:497 |
| 397 | H | 6-Me-Py-3-yl | — | FA:392 |
| 398 | H | 1-Me-benzoIM-5-yl | — | FA:431 |
| 399 | Me(HO)CH₂ | Ph | — | FA:421 |
| 400 | 1-Oxido-Py-3-ylCH₂NH | Ph | — | FA:499 |
| 401 | HO | Ph | — | FA:393 |

TABLE 27

| Ex | Str | DAT |
|---|---|---|
| 110 | | FA: 391 |
| 111 | | FA: 394 |

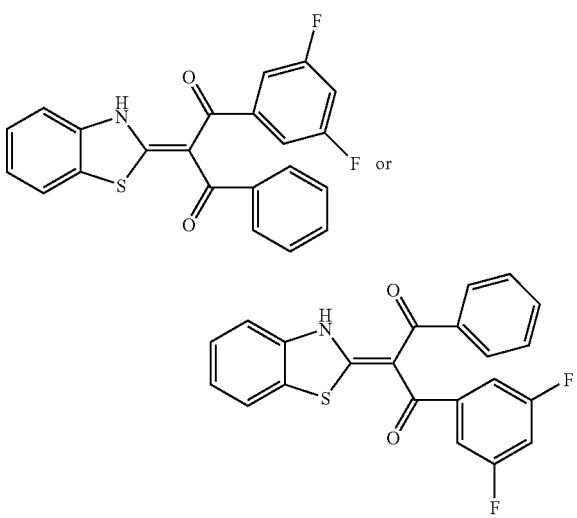

TABLE 27-continued

| Ex | Str | DAT |
|---|---|---|
| 450 | 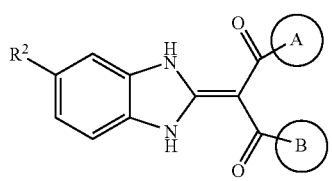 | FA:542, FN:540 |

TABLE 28

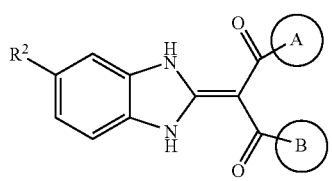

| EX | R² | A | B | Sa | DAT |
|---|---|---|---|---|---|
| 402 | Py-3-ylCH₂O | 3,5-diF-Ph | Ph | Oxal | FA:483 |
| 403 | PhCH₂SO₂ | 3,5-diF-Ph | Ph | — | FA:530 |
| 404 | 1-Oxido-Py-3-ylCH=N | 3,5-diF-Ph | Ph | — | FA:497 |
| 405 | HOCH₂ | 3,5-diF-Ph | Ph | — | FA:407 |
| 406 | BenzoIM-5-ylCH₂NH | 3,5-diF-Ph | Ph | — | FA:522 |
| 407 | PhNHCSNH | 3,5-diF-Ph | Ph | — | FA:527 |
| 408 | Py-3-ylNHCONH | 3,5-diF-Ph | Ph | — | FA:512 |
| 409 | HCO | 3,5-diF-Ph | Ph | — | FA:405 |
| 410 | 4-AcNHPhCH₂NH | 3-Me-Ph | 3-Me-Ph | — | FA:531 |
| 411 | H₂N | 3-Me-Ph | 3-Me-Ph | — | FA:384 |
| 412 | 4-H₂N-PhCH₂NH | 3,5-diF-Ph | 2,3-diMe-Ph | — | FA:523 |
| 413 | 4-iPrNHOC-PhCH₂NH | 3,5-diF-Ph | 3-Me-Ph | — | FA:581 |
| 414 | 4-HOOC-PhCH₂NH | 3,5-diF-Ph | 3-Me-Ph | — | FA:540 |
| 415 | 4-[Pyrroli-1-yl(CH₂)₂O]-PhCH₂NH | 3,5-diF-Ph | 3-Me-Ph | — | FA:609 |
| 416 | PhO-CONH | 3,5-diF-Ph | Ph | — | FA:512 |
| 417 | 4-MeOCH₂CONH-PhCH₂(MeOCH₂CO)N | 3,5-diF-Ph | 2,3-diMe-Ph | — | FA:669 |
| 418 | 4-cBuCONH-PhCH₂NH | 3,5-diF-Ph | 2,3-diMe-Ph | — | FA:607 |
| 419 | 4-Et₂N(CH₂)₂CONH-PhCH₂NH | 3,5-diF-Ph | 2,3-diMe-Ph | Oxal | FA:652 |
| 420 | 4-MeNHCH₂CONH-PhCH₂NH | 3,5-diF-Ph | 2,3-diMe-Ph | Oxal | FA:596 |
| 422 | 1,3-Thiaz-5-ylCH₂NH | 3,5-diF-Ph | 3-Me-Ph | Oxal | FA:503 |
| 423 | 2-H₂N-1,3-Thiaz-5-ylCH₂NH | 3,5-diF-Ph | 3-Me-Ph | — | FA:518 |
| 424 | 2-AcNH-1,3-Thiaz-5-ylCH₂NH | 3,5-diF-Ph | 3-Me-Ph | — | FA:560 |
| 425 | 4-MeO-Ph | 3,5-diF-Ph | 3-Me-Ph | — | FA:497 |
| 426 | 1-PhCH₂-Pipe-4-ylCH₂NH | 3,5-diF-Ph | Ph | HCl | FA:579 |
| 427 | 4-Me-PhSO₂(Me)N | 3,5-diF-Ph | Ph | — | FA:560 |
| 428 | 1,3-Thiaz-5-ylCH₂NH | 3,5-diF-Ph | 2,3-diMe-Ph | Oxal | FA:517 |
| 430 | 4-MeO-PhNHCO | 3,5-diF-Ph | Ph | — | FA:526 |
| 431 | PhCH₂O-CO | 3,5-diF-Ph | Ph | — | FA:511 |
| 432 | HOOC | 3,5-diF-Ph | Ph | — | FA:421 |
| 433 | 4-F-PhCO(Me)N | 3,5-diF-Ph | Ph | — | FA:528 |
| 434 | MeNH | 3,5-diF-Ph | Ph | — | FA:406 |
| 435 | 2-tBuO-CONH-4-Cl-1,3-Thiaz-5-ylCH₂NH | 3,5-diF-Ph | 3-Me-Ph | — | FA:652 |
| 436 | 2-tBuO-CONH-4-Cl-1,3-Thiaz-5-ylCH=N | 3,5-diF-Ph | 3-Me-Ph | — | FA:650 |
| 437 | 4-AcNH-PhCH₂NH | 3,5-diF-Ph | 3-AcO-2-Me-Ph | — | FA:611 |

TABLE 29

| EX | R² | A | B | Sa | DAT |
|---|---|---|---|---|---|
| 421 | 1,3-Thiaz-5-ylCH₂NH | 3,5-diF-Ph | 2-MeO-Ph | Oxal | FA:519, N1:3.64(3H, s), 4.54 (2H, s), 6.59(1H, d, J = 8Hz), 6.68-6.72(2H, m), 6.77(2H, dd, J=2Hz, 8Hz), 6.90(1H, tt, J=2Hz, 9Hz), 6.91(1H, d, J=2Hz), 7.01-7.07(2H, m), 7.45(1H, d, J=9Hz), 7.89(1H, s), 8.96(1H, s), 12.90(1H, s), 12.96(1H, s) |
| 438 | 4-AcNH-PhCH₂NH | 3,5-diF-Ph | 3-HO-2-Me-Ph | — | FA:569 |
| 439 | 4-Ac(Me)N-PhCH₂NH | 3,5-diF-Ph | 3-Me-Ph | — | FA:567 |
| 440 | 4-F₃CCONH-PhCH₂NH | 3,5-diF-Ph | 3-Me-Ph | — | FA:607 |
| 441 | 4-MeSO₂NH-PhCH₂NH | 3,5-diF-Ph | 3-Me-Ph | — | FA:589 |
| 442 | 4-AcNH-PhCH₂O | 3,5-diF-Ph | 3-Me-Ph | — | FA:554, N1:2.05(3H, s), 2.51(3H, s), 5.06(2H, s), 6.86-7.07(7H, m), 7.14 (1H, d, J=7Hz), 7.39 (1H, s), 7.41(2H, d, J=9Hz), 7.61 (2H, d, J=9Hz), 7.64 (1H, s), 9.98(1H, s), 13.06 (2H, s) |
| 443 | 4-AcNH-PhCH₂NH | 4-F-Ph | 3-Me-Ph | — | FA:535 |
| 444 | 4-AcNH-PhCH₂NH | 2-MeO-Ph | 3-Me-Ph | — | FA:547 |
| 445 | 4-AcNH-PhCH₂NH | 2,3-diMe-Ph | 3-Me-Ph | — | FA:545 |
| 446 | 4-MeO-Ph(Me)NCO | 3,5-diF-Ph | Ph | — | FA:540 |
| 447 | 4-[BocHNC(NBoc)NH]-PhCH₂NH | 3,5-diF-Ph | 3-Me-Ph | — | FA:753 |
| 448 | 4-[H₂NC(NH)NH]-PhCH₂NH | 3,5-diF-Ph | 3-Me-Ph | HCl | FA:553 |
| 449 | 4-MeSO₂NH-PhCH₂(MeSO₂)N | 3,5-diP-Ph | 3-Me-Ph | — | FA:667 |

TABLE 30

| Ex | R¹-Z¹ | R²-Z² | DAT |
|---|---|---|---|
| 24 | CH | N | FA:342, N1:7.04-7.38(11H, m), 8.00(1H, m), 8.34(1H, m), 13.13-13.19(2H, m) |
| 25 | N | CH | FA:342, N1:7.04-7.34(10H, m), 7.66(1H, m), 8.41(1H, m), 8.91(1H, m), 13.21(m, 2H) |

TABLE 31

| Ex | R² | R⁶ | Sa | DAT |
|---|---|---|---|---|
| 114 | H | Me | — | FA:355 |
| 115 | H | PhCH₂ | — | FA:429 |
| 116 | Me | Et₂N | HCl | FA:426 |

TABLE 32

| Ex | R¹⁶ | DAT |
|----|-----|-----|
| 53 | Ac | FA:455 |
| 54 | PhCO | FA:579 |
| 55 | 2-F₃C-PhCO | FA:715 |
| 56 | (N-benzyl-2-oxo-propyl)-4-methylbenzenesulfonamide structure | FA:973 |
| 57 | 2-Me-PhCO | FA:607 |
| 58 | PhCH₂CO | FA:607 |
| 59 | 2-PyCO | FA:581 |
| 60 | MeOCH₂CO | FA:515 |
| 61 | 4-F-PhCO | FA:615 |
| 62 | iPrCO | FA:511 |
| 63 | 3-Cl-PhCO | FA:647 |
| 64 | 3-MeO-PhCO | FA:639 |
| 65 | EtOCOCO | FA:571 |

TABLE 32-continued

| Ex | R¹⁶ | DAT |
|----|-----|-----|
| 66 | 4-CN-PhCO | FA:629 |
| 67 | iPrSO₂ | FA:583 |
| 68 | 4-F-PhSO₂ | FA:687 |
| 69 | 2-F₃C-PhSO₂ | FA:787 |
| 70 | MeSO₂ | FA:527 |
| 71 | BuSO₂ | FA:611 |
| 72 | Me₂NSO₂ | FA:585 |
| 73 | PhCH₂SO₂ | FA:679 |
| 74 | PhSO₂ | FA:651 |
| 75 | 3-Me-PhSO₂ | FA:679 |
| 76 | 2,4-di-F-PhSO₂ | FA:723 |
| 77 | 4-MeO-PhSO₂ | FA:711 |
| 78 | 3-O₂N-PhSO₂ | FA:741 |
| 91 | cHex-CH₂ | FA:563 |
| 92 | PhCH₂ | FA:551 |
| 93 | 2-(EtO)PhCH₂ | FA:639 |
| 94 | 3-BrPhCH₂ | FA:709 |
| 95 | 3-MePhCH₂ | FA:579 |
| 96 | 3-NO₂PhCH₂ | FA:641 |
| 97 | 4-(MeOCO)PhCH₂ | FA:667 |
| 98 | 2,4-diF-PhCH₂ | FA:623 |
| 99 | 3-PyCH₂ | FA:553 |
| 100 | 4-IM-CH₂ | FA:530 |

TABLE 33

| EX | R¹ | R² | A | B | Sa | DAT |
|----|----|----|---|---|-----|-----|
| 101 | H | H | 2-Me-1,3-Thiaz-4-yl | Ph | — | FA:362, N1: 2.30(3H, s), 7.64(1H, s), 13.04(2H, s) |
| 102 | H | MeO | Ph | Ph | — | FA:371 |
| 103 | H | H | 4-Py | Ph | — | FA:342 |
| 104 | Me | H | Ph | Ph | — | FA:355 |
| 105 | H | H | 3-Py | Ph | — | FA:342, N1: 8.24(1H, dd, J= 1.5, 4.4), 8.42(1H, d, J= 1.5), 13.18(2H, s) |
| 106 | H | H | Ph | 3-{Mo-4-yl(CH₂)₂O}Ph | — | FA:470 |
| 107 | H | H | Ph | 3-Me₂NPh | — | FA:384 |
| 108 | H | H | Ph | 3-{Me(PhCH₂)NCH₂}Ph | HCl | FA:474 |
| 109 | H | H | 3,5-diF-Ph | Py-3-yl | HCl | FA:378, N1: 7.79-7.81(2H, m), 8.74(1H, d, J=1.5), 13.28(2H, s) |
| 112 | H | H | 5-HO-Py-3-yl | 3,5-diF-Ph | — | FA:394 |
| 113 | H | OH | 3-MePh | 3-MePh | — | FA:383 |

INDUSTRIAL APPLICABILITY

Since the compounds of the invention have sex hormone-decreasing effect based on GnRH receptor antagonism, they are useful for treating sex hormone-dependent diseases, for example, prostate cancer, breast cancer, endometriosis, uterine leiomyoma, and the like (Proc. Natl. Acad. Sci. USA, 87, 7100-7104 (1990)).

In the following, in vitro GnRH receptor antagonistic effect of the pharmaceutical drugs and compounds of the invention was evaluated by inhibition of binding of $^{125}$I-D-Trp$^6$-LHRH to human GnRH receptor.

1. Test of In Vitro GnRH Receptor Antagonism (1) Preparation of Human GnRH Receptor-Expressing CHO (Chinese Hamster Ovary) Cells Expression of human GnRH was carried out in a similar manner to a common method for protein expression (Chapter 9 In: Current Protocols In Molecular Biology: ed. by F. M. Ausubel et al., Greene Publishing Associates and Wiley-Interscience, 9.0.1-9.9.6 (1987), S. S. Kaker et al., Biol. Biophys. Res. Commun. 189, 289-295 (1992), R. Grosse et al., Mol. Endocrinol. 11, 1305-1318 (1997)). CHO cells were cultured (medium: AMEM, 10% FCS, containing an antibiotic-antimycotic agent) with an expression vector which has human GnRH receptor gene (SEQ ID No.: 1) and a transfection reagent FuGENE6 (manufactured by Boehringer-Mannheim) for 24 hours for transfection, whereby the CHO cells stably expressing human GnRH receptor (SEQ ID No.: 2, S. S. Kaker et al., Biol. Biophys. Res. Commun, 189, 289-295 (1992)) were obtained. The expression of the aimed receptor was confirmed by PCR method.

(2) Preparation of CHO Cell Membrane Fraction Containing Human GnRH Receptor

The CHO cells expressing the human GnRH receptor ($3\times10^8$ cells), prepared in the above (1), were suspended in phosphate buffered saline (PBS) and centrifuged for 3 minutes at 100×G. The pellet suspended in 100 ml of a homogenate buffer (10 mM NaHCO$_3$, 5 mM EDTA (ethylenediaminetetraacetic acid), pH 7.5) was homogenized using a Polytron homogenizer. After the resulting homogenate was centrifuged for 15 minutes at 400×G, the supernatant was centrifuged for 1 hour at 10,000×G. The membrane fraction obtained as a pellet was suspended in 60 ml of storage buffer (25 mM Tris-HCl, 1 mM EDTA, 10 µg/ml a protease inhibitor (Pefabloc SC (manufactured by Merck)), 1 µg/ml pepstatin A, 20 µg/ml leupeptin, 0.03% sodium azide, pH 7.5), and stored at −80° C. until use.

(3) Measurement of $^{125}$I-D-Trp$^6$-LHRH Binding Inhibition

The membrane fractions of CHO cells expressing the human GnRH receptor which were prepared in the above (2) were diluted with assay buffer (HBSS (Hanks balanced salt solution), 20 mM HEPES, 0.1% BSA (bovine serum albumin), 100 µg/ml bacitracin, pH 7.4) so as to be 20 µg/tube, and were dispensed into tubes in an amount of 148 µl. Incubation (at 4° C. for 3 hours) was initiated by adding a test compound having a different concentration dissolved in DMSO (2 µl) and 0.1 nM $^{125}$I-D-Trp$^6$-LHRH (50 µl) (SEQ ID No.: 3). DMSO (2 µl) was added instead of the test compound for measuring a total binding and 100 µM LHRH (2 µl) (SEQ ID No.: 4) for non-specific binding. Incubation was terminated and bound and free ligands were separated by rapid filtration through a Whatman glass filter (GF/B) treated with 0.5% polyethyleneimine. The filters were washed three times with 1 ml of assay buffer and the radioactivity on the filter was measured using a γ-counter. Binding inhibition (%) (PMB) of each test compound at various concentrations were determined according to the following equation: PMB=(SB−NSB)/(TB−NSB)×100 (wherein TB: total binding radioactivity, SB: radioactivity when a test compound was added, NSB: non-specific binding radioactivity). PMB at each concentration of each test compound was plotted and the concentration of the test compound at which PMB equals 50% (IC$_{50}$ value) was determined. As a result of the test, it was confirmed that the compound No. 178a in Table 6 and the compounds of Examples 40, 43, 79, 83, 87, 132, 146, 147, 169, 209, 224, 239, 241, 245, 251, 256, 258, 290, 293, 400, 402, 421, 422 and 423 have IC$_{50}$ values of $10^{-10}$M to $10^{-9}$M. In particular, the compounds of the invention having a dihydrobenzimidazol-2-ylidene-substituted propane-1,3-dione skeleton have GnRH receptor binding inhibitory activities equal to that of Cetrorelix, a peptide antagonist, which is commercialized at present.

2. Test of In Vivo GnRH Receptor Antagonism

In vivo GnRH antagonistic effect of each compound was evaluated by inhibitory effect on the increase of serum testosterone induced by GnRH administration in rats.

GnRH (30 ng/rat; Peptide Institute, LH-RH (human)) (SEQ ID No.: 4) was administered intramuscularly to Wistar male rats (9 wk old; Japan SLC). Each test compound was dissolved or suspended in a 6.7% DMSO, 6.7% PEG400, 6.7% Tween 80 aqueous solution and was administered orally (30 mg/kg) 3 hours before the GnRH administration. Blood specimens were obtained 1 hour after the GnRH administration, and the serum concentration of testosterone was measured by a specific radioimmunoassay (IATRON Labs.).

The inhibitory activity (%) (IA) of the test compound was determined according to the following equation: IA=(Tc−Ts)/(Tc−Tn)×100; wherein Tn: the serum testosterone concentration of rats to which GnRH was not administered, Tc: the serum testosterone concentration of rats to which the solvent was administered instead of the test compound, Ts: the serum testosterone concentration of rats to which the test compound was administered (when the concentration is decreased to Tn, IA becomes 100%). As a result of the test, the compound No. 63a in Table 5, the compound No. 167a, 169a and 173a, and the compounds of Examples 40, 212, 241, 244, 245, 251, 256, 260, 274, 275, 288, 289, 290, 291, 293, 296, 297, 298, 301, 302, 303, 311 and 421 showed inhibitory activities larger than 50%.

From the test 1 and 2 in the above, it has been proved that the compounds of the invention have a sex hormone-decreasing effect based on a strong GnRH receptor antagonism, and hence are useful for treating sex hormone-dependent diseases, for example, prostate cancer, breast cancer, endometriosis, uterine leiomyoma, and the like (C. Huggins & C. V. Hodges, Cancer Res. 1, 293-297 (1941), L. Bokser et al., Proc. Natl. Acad. Sci. USA, 87, 7100-7104 (1990)).

The invention claimed is:

1. A propane-1,3-dione compound represented by the general formula (I):

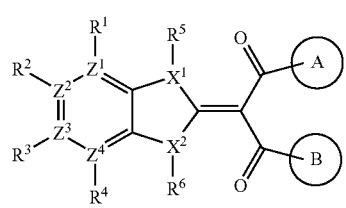

(I)

($R^1$, $R^2$, $R^3$ and $R^4$: the same or different, H, $NO_2$, CN, Halo, a hydrocarbon group which may be substituted, a heterocycle which may be substituted, a hydroxy which may be substituted, a carboxy which may be substituted, an acyl-O— which may be substituted, an acyl which may be substituted, a substituent —S(O)$n_{101}$— ($n_{101}$: an integer of 0 to 2, the same shall apply hereinafter), H—S(O)$n_{101}$—, a carbamoyl which may be substituted, a sulfamoyl which may be substituted, or an amino which may be substituted, and two adjacent groups selected from the group of $R^1$, $R^2$, $R^3$ and $R^4$ may be combined to form an aryl or a cycloalkenyl; $R^5$ and $R^6$: the same or different, H, Halo, a hydrocarbon group which may be substituted or an amino which may be substituted; $X^1$ and $X^2$: the same or different, N, S or O atom; A and B: the same or different, an aryl which may be substituted or a heterocycle which may be substituted; $Z^1$, $Z^2$, $Z^3$ and $Z^4$: C or N; provided that 1) when $X^1$ and $X^2$ each is S or O, one or both of the corresponding $R^5$ and $R^6$ are absent; 2) when one to four of $Z^1$, $Z^2$, $Z^3$ and/or $Z^4$ are N, the corresponding $R^1$, $R^2$, $R^3$ and/or $R^4$ are absent; and 3) that if one of A and B is phenyl, the other is not 4-nitrophenyl)

or a pharmaceutically acceptable salt thereof, provided that the compounds 1 to 39 shown in the following table are excluded, wherein the symbol Ph means phenyl, Me means methyl, Et means ethyl, and tBu means tert-butyl,

TABLE 1

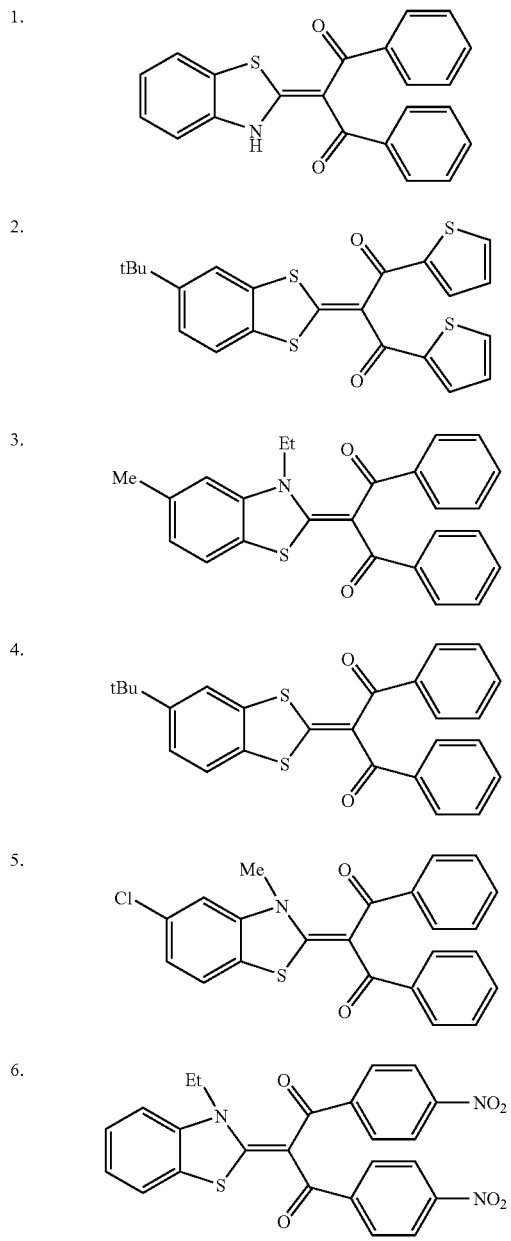

TABLE 1-continued

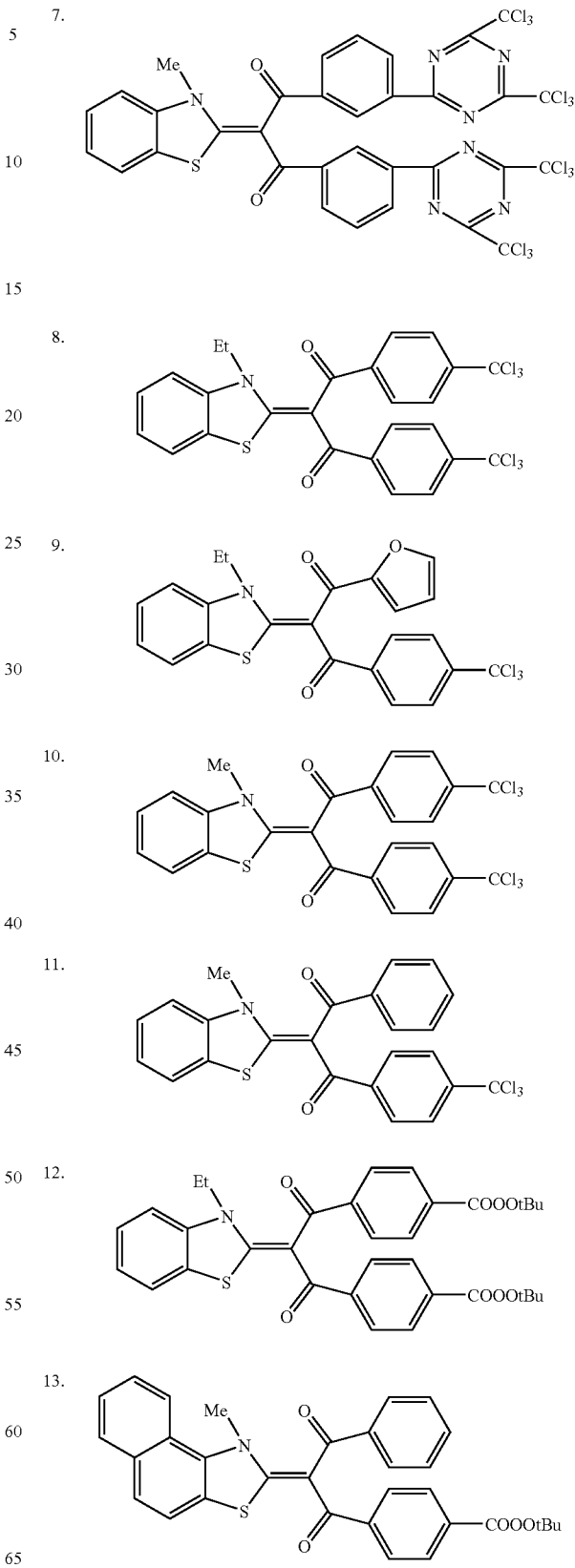

TABLE 1-continued
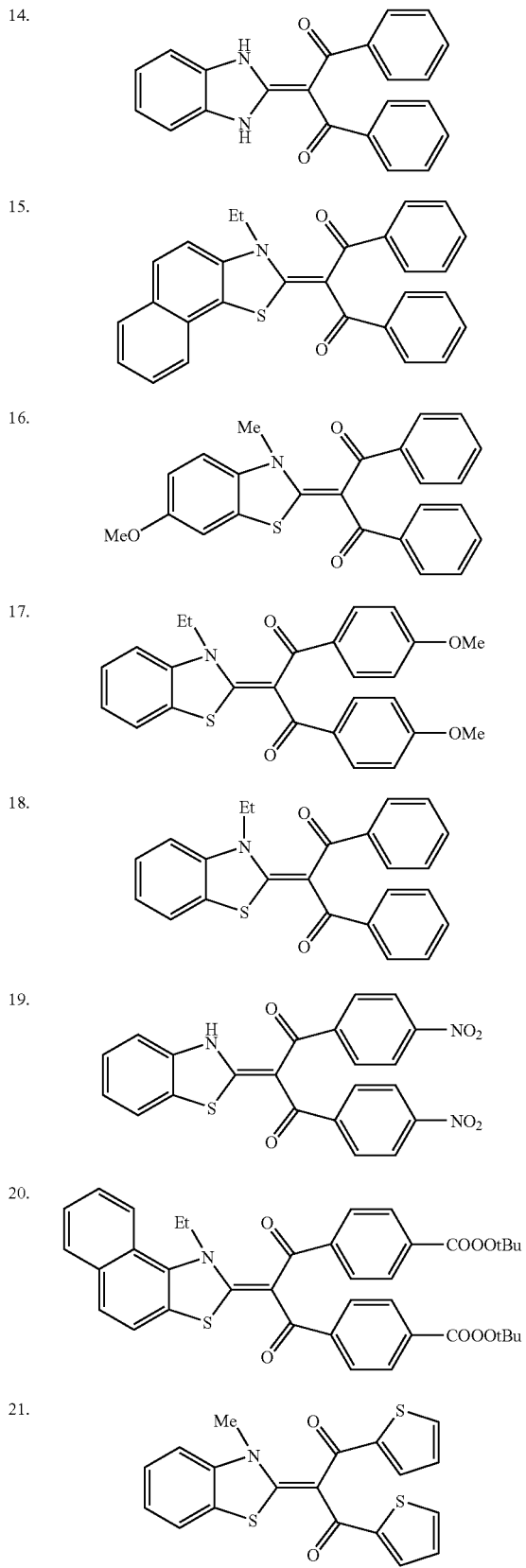
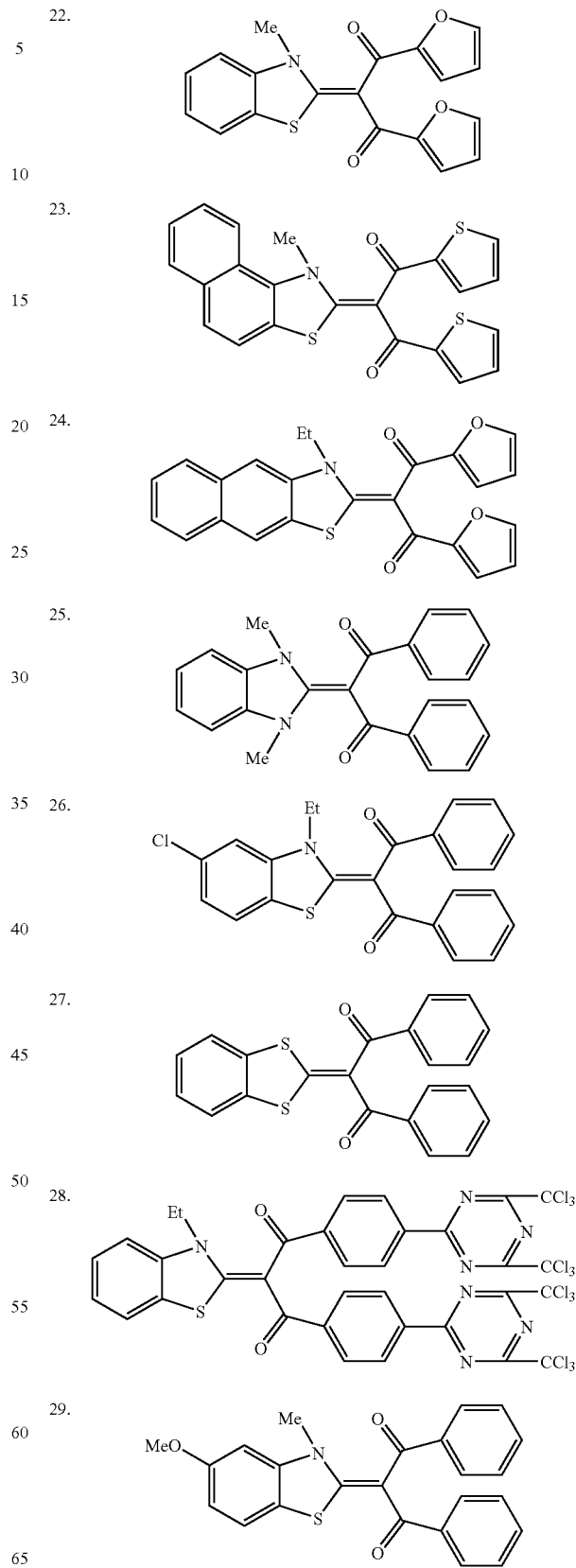

TABLE 1-continued
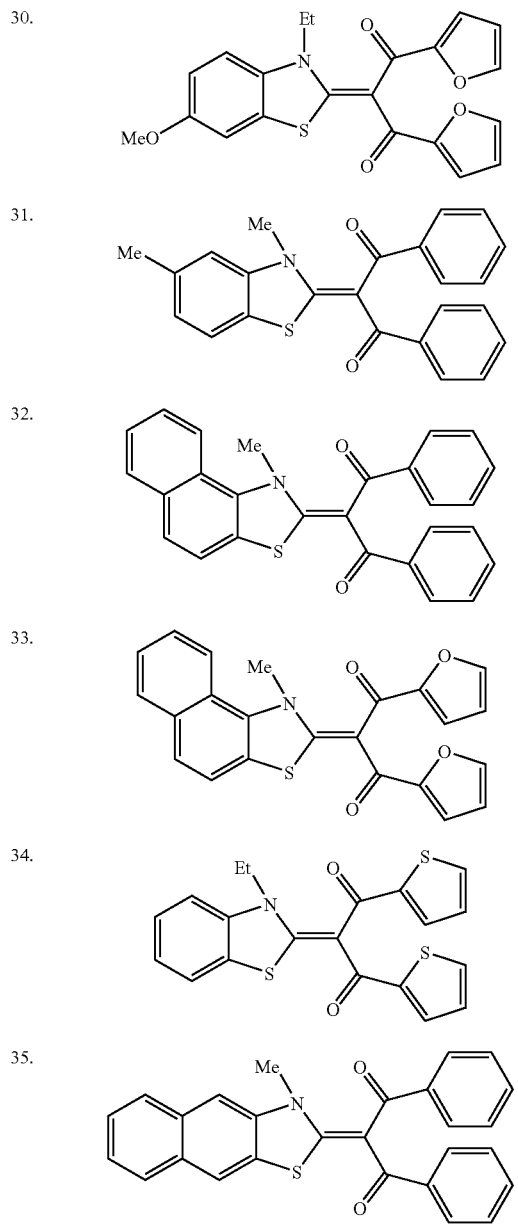
TABLE 1-continued
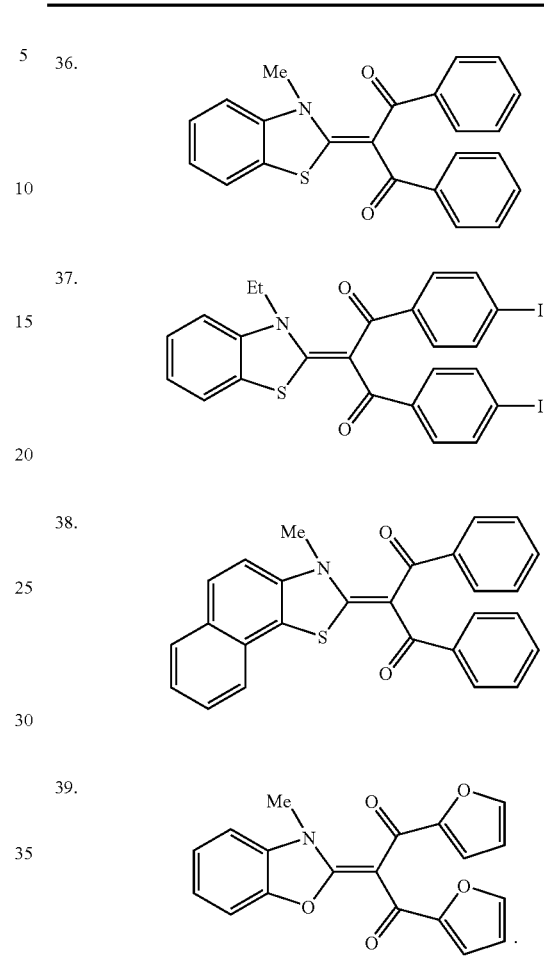
2. The propane-1,3-dione compound or a pharmaceutically acceptable salt thereof according to claim 1, wherein at least any one of $X^1$ and $X^2$ is N.
3. The propane-1,3-dione compound or a pharmaceutically acceptable salt thereof according to claim 1 or 2, wherein $X^1$ and $X^2$ are N at the same time.
* * * * *